United States Patent
Kim et al.

(10) Patent No.: US 12,296,019 B2
(45) Date of Patent: May 13, 2025

(54) COMPOUND FOR PREPARATION OF ANTIBODY-PAYLOAD CONJUGATE AND USE THEREOF

(71) Applicants: AbTis Co., Ltd., Gyeonggi-do (KR); RESEARCH & BUSINESS FOUNDATION SUNGKYUNKWAN UNIVERSITY, Gyeonggi-do (KR)

(72) Inventors: Ju Hwan Kim, Gyeonggi-do (KR); Tae Jin Lee, Gyeonggi-do (KR); Sang Jeon Chung, Gyeonggi-do (KR); Young Geun Lee, Gyeonggi-do (KR); Jin Woo Seo, Gyeonggi-do (KR)

(73) Assignees: ABTIS CO., LTD., Gyeonggi-do (KR); RESEARCH & BUSINESS FOUNDATION SUNGKYUNKWAN UNIVERSITY, Gyeonggi-do (KR)

( * ) Notice: Subject to any disclaimer, the term of this patent is extended or adjusted under 35 U.S.C. 154(b) by 664 days.

(21) Appl. No.: 17/424,528

(22) PCT Filed: Jan. 23, 2020

(86) PCT No.: PCT/KR2020/001145
§ 371 (c)(1),
(2) Date: Jul. 21, 2021

(87) PCT Pub. No.: WO2020/153774
PCT Pub. Date: Jul. 30, 2020

(65) Prior Publication Data
US 2022/0072147 A1    Mar. 10, 2022

(30) Foreign Application Priority Data
Jan. 23, 2019   (KR) .................. 10-2019-0008943

(51) Int. Cl.
*A61K 47/68* (2017.01)
*A61K 31/537* (2006.01)
(Continued)

(52) U.S. Cl.
CPC ............ *A61K 47/65* (2017.08); *A61K 31/537* (2013.01); *A61K 47/545* (2017.08);
(Continued)

(58) Field of Classification Search
None
See application file for complete search history.

(56) References Cited

U.S. PATENT DOCUMENTS

| | | |
|---|---|---|
| 10,335,420 B2 | 7/2019 | Reisfeld et al. |
| 10,533,058 B2 | 1/2020 | Flygare et al. |

(Continued)

FOREIGN PATENT DOCUMENTS

| | | |
|---|---|---|
| CN | 103179952 A | 6/2013 |
| CN | 104185477 A | 12/2014 |

(Continued)

OTHER PUBLICATIONS

International Search Report of PCT Application No. PCT/KR2020/001145, May 18, 2020.
(Continued)

*Primary Examiner* — Karl J Puttlitz
(74) *Attorney, Agent, or Firm* — Harness, Dickey & Pierce, P.L.C.

(57) ABSTRACT

The present application relates to a novel linker for use in bioconjugation, comprising two or more electrophilic carbon atoms of a carbonyl group, and a click chemistry functional group and, more specifically, to a linker through which a compound, a peptide, and/or a protein can be
(Continued)

directly and/or indirectly linked by a substitution reaction to a desired target molecule, that is, a target molecule.

12 Claims, 41 Drawing Sheets

Specification includes a Sequence Listing.

(51) Int. Cl.
*A61K 47/54* (2017.01)
*A61K 47/65* (2017.01)

(52) U.S. Cl.
CPC .... *A61K 47/68033* (2023.08); *A61K 47/6849* (2017.08); *A61K 47/6889* (2017.08)

(56) References Cited

U.S. PATENT DOCUMENTS

| | | | |
|---|---|---|---|
| 2013/0129753 | A1 | 5/2013 | Doroski et al. |
| 2014/0363454 | A1 | 12/2014 | Jackson et al. |
| 2015/0023989 | A1 | 1/2015 | Lerchen et al. |
| 2017/0021033 | A1 | 1/2017 | Geierstanger et al. |
| 2017/0362266 | A1 | 12/2017 | Ott et al. |
| 2018/0333504 | A1 | 11/2018 | Han et al. |
| 2023/0158167 | A1* | 5/2023 | Chung ............... A61K 47/6803 |

FOREIGN PATENT DOCUMENTS

| | | |
|---|---|---|
| CN | 104254342 A | 12/2014 |
| CN | 106659800 A | 5/2017 |
| CN | 107614514 A | 1/2018 |
| EP | 3 299 383 A1 | 3/2018 |
| KR | 10-2014-0017486 A | 2/2014 |
| KR | 10-2014-0077207 A | 6/2014 |
| KR | 10-2014-0114826 A | 9/2014 |
| KR | 10-2016-0110379 A | 9/2016 |
| KR | 10-2016-0125515 A | 10/2016 |
| KR | 10-2018-0002734 A | 1/2018 |
| KR | 10-2019-0020034 A | 2/2019 |
| WO | WO-2014-197871 A2 | 12/2014 |
| WO | WO-2016/186206 A1 | 11/2016 |
| WO | WO-2018-061509 A1 | 4/2018 |
| WO | WO-2018-112108 A1 | 6/2018 |
| WO | WO-2018-199337 A1 | 11/2018 |
| WO | WO-2018/213077 A1 | 11/2018 |
| WO | WO-2020/184944 A1 | 9/2020 |

OTHER PUBLICATIONS

Written Opinion of PCT Application No. PCT/KR2020/001145, May 18, 2020.
Office Action of KR Application No. 10-2020-0009162, Jun. 21, 2021.
Office Action of the CN Patent Application No. 202080023611.1 issued on Jan. 20, 2024.
Notice of Allowance from corresponding Korean Patent Application No. 10-2022-0016118, dated Oct. 27, 2023.
Japanese Office Action in Application No. 2021-543283 dated Oct. 31, 2022.
European Search Report from corresponding European Patent Application No. 20745652.6, dated Jan. 5, 2023.
Angewandte Chemie International Edition, vol. 58, No. 27, Apr. 17, 2019(Apr. 17, 2019), pp. 9068-9072.
Li, P., et al.; "Base-Mediated Intramolecular Decarboxylative Synthesis of Alkylamines from Alkanoyloxycarbamates", JOC The Journal of Organic Chemstry, 2018, 83, 8233-8240.
Office Action from corresponding European Patent Application No. 20745652.6, dated Dec. 19, 2024.

* cited by examiner

FIG. 27

IC$_{50}$ of ADC

|  | Kadcyla | 1.5 Generation ADC |
|---|---|---|
| NCI-N87 | 52.8 ng/mL | 82.1 ng/mL |
| BT474 | 12.3 ng/mL | 29.6 ng/mL |
| MDA-MB-468 | ND | ND |

COMPOUND FOR PREPARATION OF ANTIBODY-PAYLOAD CONJUGATE AND USE THEREOF

CROSS-REFERENCE TO RELATED APPLICATIONS

This application is a national phase application of PCT Application No. PCT/KR2020/001145, filed on 23 Jan. 2020, which claims the benefit of and priority to Korean Application No. 10-2019-0008943, filed 23 Jan. 2019. The entire disclosures of the applications identified in this paragraph are incorporated herein by references.

TECHNICAL FIELD

The present invention relates to the field of bioconjugation. The present invention relates to a linker for preparation of a site-specific bound antibody-payload conjugate, an antibody-payload conjugate prepared using the same, and a method for preparing the antibody-payload conjugate. More specifically, the present invention relates to a linker, in which the linker includes a carbonyl group carbon having two or more different partial positive charges and functional groups at both ends, and can link a compound, a peptide, and/or a protein by a substitution reaction to a biological (target) molecule.

BACKGROUND

Bioconjugation is a process of linking at least two or more molecules, and in this case, bioconjugation refers to a process in which at least one or more molecules are bioactive molecules. The bioactive molecule may be sometimes referred to as a "target molecule" or a "molecule of interest", and may be, for example, a protein (or a peptide), a glycan, a nucleic acid (or an oligonucleotide), a lipid, a hormone or a natural drug (or a fragment thereof, or combinations thereof), and the like. Such a linker that links two or more molecules can be widely used for detection, diagnosis, a biomarker, and the like by binding a target-specific protein such as an antibody to a fluorescent material or the like.

Currently, for a linker used for detection, diagnosis, treatment, and the like as bioconjugation, for example, polyethylene glycol (PEG) is widely used commercially because PEG is highly water-soluble, non-toxic, non-antigenic and does not aggregate. Recently, as there has been increasing interest in a therapeutic that treats a specific disease by linking a cytotoxic drug (anticancer drug) to an antibody, studies on a linker capable of binding the cytotoxic drug to a target molecule such as an antibody have also been actively conducted. For a linker capable of linking these two or more molecules, in vivo blood stability, compatibility, solubility, target specificity, and the like all need to be considered.

Meanwhile, linkers currently being studied in the field of antibody-payload conjugates have problems in that the biological activity of the antibody is reduced by its length and size. for example, there are problems such as a decrease in half-life by blocking FcRn receptor binding, and difficulties in producing a homogenous antibody-drug conjugate due to difficulty in site-specific binding. Therefore, there is an urgent need for the development of a linker having excellent blood stability in vivo, compatibility, solubility, and site specificity while maintaining the activity of a target molecule.

To solve these problems, the present inventors of the present invention invented a linker, capable of linking a payload to a target molecule without affecting the biological activity of the target molecule, that includes a carbonyl group having two or more different partial positive charges (δ+), and a leaving group and/or a click compound at both ends. The linker may increase reactivity by increasing not only site-specificity, but also water solubility for the target molecule through length adjustment. Since such a linker does not have strict reaction conditions and has a high conjugation yield for a molecule including a target molecule as bioconjugation, it is intended to provide a more stable and economically highly effective linker.

SUMMARY

Technical Problem

The present application is subjected to provide a linker, having a novel trans structure, including two or more electrophilic carbons of carbonyl groups and one or more click chemical moieties, and a method for preparing the same.

The present application is subjected to provide a linker, having a novel cis structure, including two or more electrophilic carbons of carbonyl groups and one or more click chemical moieties, and a method for preparing the same.

Technical Solution

To solve the above-described problems of the present application, the present specification provides a linker that assists in transport and binding reactions in order to directly and/or indirectly link a payload to a target molecule.

In an aspect, the present application provides a compound represented by the following Formula 2:

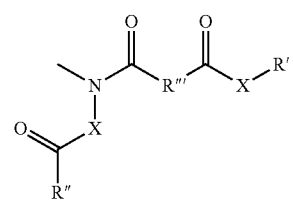

[Formula 2]

in formula 2, R' is ester group activating moiety, R" is any one of acetylene, transcyclooctene, cyclooctyne, diarylcyclooctyne, methyl ester phosphine, norbornene, methylcyclopropene, azetine and cyanide, R''' is substituted or unsubstituted $C_{1-20}$ alkylene, substituted or unsubstituted $C_{2-20}$ alkenylene, substituted or unsubstituted $C_{1-10}$ alkynylene, substituted or unsubstituted $C_{1-10}$ polymethylene, substituted or unsubstituted $C_{5-12}$ aryl, substituted or unsubstituted $C_{5-14}$ aryl alkylene, substituted or unsubstituted $C_{8-16}$ aryl alkenylene, substituted or unsubstituted $C_{3-10}$ cycloalkylene, substituted or unsubstituted $C_{3-10}$ heterocycloalkylene, or substituted or unsubstituted $C_{5-12}$ heteroaryl, and the heteroalkylene, heterocycloalkylene, or heteroaryl includes at least one or more selected from a group of N, O, and S, the substitution is substituted with a non-hydrogen substituent, the non-hydrogen substituent is any one or more selected from a group consisting of —Ra, —O—, =O, —ORa, —SRa, —S—, —N(Ra)$_2$, =NRa, —C(Rb)$_3$, —N=C=O, —NCS, —NO, —NO$_2$, =N—OH, =N$_2$, —N$_3$, —NHC (=O)Ra, —C(=O)Ra, —C(=O)NRaRa, —S(=O)₂O—, —S(=O)₂OH, —S(=O)₂Ra, —OS(=O)₂ORa, —S(=O)₂NRa, —S(=O)Ra, —C(=O)Ra, alkylene-C(=O)Ra, —C(=S)Ra, —C(=O)ORa, alkylene-C(=O)ORa, —C(=O)O—, alkylene-C(=O)O—, —C(=S)ORa, —C(=O)SRa, —C(=S)SRa, —C(=O)NRaRa, alkylene-C(=O)NRaRa, —C(=S)NRaRa, —C(—NRa)NRaRa, and Rb, Ra is H, C₁₋₆ alkyl, C₅₋₁₂ aryl, C₇₋₁₂ arylalkyl or heterocycle, Rb is F, Cl, Br, or I, X is O, N or S. In addition, the present application provides a compound in which R″ is selected from a group consisting of norbornene, transcyclooctene, cyclooctyne and methylcyclopropene. Furthermore, the present application provides a compound in which R″ is norbornene.

Furthermore, the present application provides a compound in which R‴ is selected from a group of substituted or unsubstituted C₁₋₁₀ alkylene, substituted or unsubstituted C₁₋₁₀ hetero alkylene, and a C₁₋₁₀ polymethylene, the heteroalkylene includes at least one or more selected from a group consisting of N, O and S, the substitution is substituted with a non-hydrogen substituent, the non-hydrogen substituent is any one or more selected from a group consisting of —O—, =O, —ORa, —SRa, —S—, —N(Ra)₂, =NRa, —N=C=O, —NCS, —NO, —NO₂, =N—OH, =N₂, —N₃, —NHC(=O)Ra, —C(=O)Ra, —C(=O)NRaRa —S(=O)₂O—, —S(=O)₂OH, —S(=O)₂Ra, —OS(=O)₂ORa, —S(=O)₂NRa, —S(=O)Ra, —C(=O)Ra, alkylene-C(=O)Ra, —C(=S)Ra, —C(=O)ORa, alkylene-C(=O)ORa, —C(=O)O—, alkylene-C(=O)O—, —C(=S)ORa, —C(=O)SRa, —C(=S)SRa, —C(=O)NRaRa, alkylene-C(=O)NRaRa, —C(=S)NRaRa, and —C(—NRa)NRaRa, Ra is C₁₋₆ alkyl, C₅₋₁₂ aryl, C₇₋₁₂ arylalkyl, or heterocycle, Rb is F, Cl, Br, or I, X is O, N, or S. Furthermore, the present application provides a compound in which R‴ is unsubstituted C₁₋₅ alkylene or unsubstituted C₁₋₅ polymethylene.

Furthermore, the present application provides a compound in which X is O.

Furthermore, the present application provides a compound in which the compound of Formula 2 is represented by the following Formula 2-1-2:

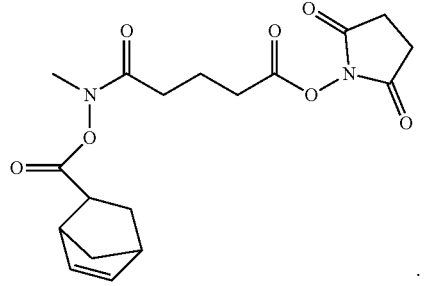

[Formula 2-1-2]

In another aspect, the present application provides a method for producing an antibody-payload conjugate, the method comprising: preparing a linker-Fc binding peptide conjugate by reacting a linker having a structure of Formula 2 with a Fc binding peptide; reacting the linker-Fc binding peptide conjugate with an antibody to obtain an antibody comprising a first click-chemistry functional group; and preparing the antibody-payload conjugate having a structure of the following Formula 8, by reacting the antibody comprising the first click-chemistry functional group with a payload comprising a second click-chemistry functional group capable of doing a click-chemistry reaction with the first click-chemistry functional group:

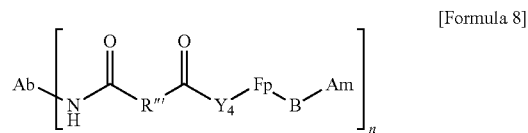

[Formula 8]

wherein, Ab is an antibody, R‴ is an unsubstituted C₁₋₅ alkylene or unsubstituted C₁₋₅ polymethylene, Y₄ is N, Fp is a Fc binding peptide, B is any one structure formed by the click-chemistry reaction of the first click-chemistry functional group and the second click-chemistry functional group, Am is an active moiety or a structure including the active moiety, wherein the active moiety is any one selected from a group consisting of a drug molecule, an imaging moiety, an optical agent, a vitamin, and a toxin, n is an integer of 1 or more and 4 or less.

Furthermore, the present application provides a method for producing an antibody-payload conjugate, wherein the Fc binding peptide is a peptide selected from a group consisting of the following Formula 13 and Formula 14, wherein

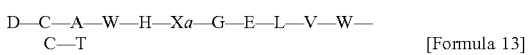

[Formula 13]

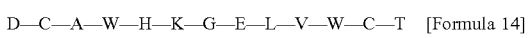

[Formula 14]

wherein D is aspartic acid, C is cysteine, A is alanine, W is tryptophan, H is histidine, Xa is

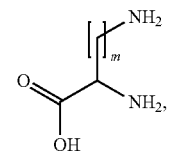

G is glycine, E is glutamate, L is leucine, V is valine, T is threonine, K is lysine, wherein, m is an integer of 1 or more and 4 or less, cysteine at the N-terminal and cysteine at the C-terminal are selectively linked to each other, n=2, and a nitrogen atom linked to Ab is contained in lysine 246 or lysine 248 of both Fcs of the antibody.

In another aspect, the present application provides an antibody-payload conjugate of the following Formula 8:

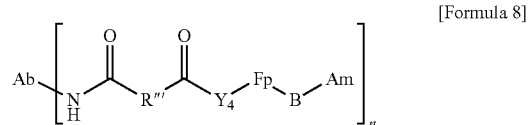

[Formula 8]

wherein, Ab is an antibody, R‴ is unsubstituted C₁₋₅ alkylene or unsubstituted C₁₋₅ polymethylene, Y₄ is N, Fp is a Fc binding peptide, B is any one structure formed by click-chemistry reaction of the first click-chemistry functional group and the second click-chemistry functional group, Am is an active moiety or a structure including the active moiety, wherein the active moiety is any one selected from a group consisting of a drug molecule, an imaging moiety, an optical agent, a vitamin, and a toxin, n is an integer of 1 or more and 4 or less.

Furthermore, the present application provides an antibody-payload conjugate, wherein the Fp is a peptide selected from a group consisting of the following Formula 13 and Formula 14,

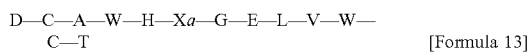
[Formula 13]

D—C—A—W—H—K—G—E—L—V—W—C—T  [Formula 14]

wherein, D is aspartic acid, C is cysteine, A is alanine, W is tryptophan, H is histidine, Xa is

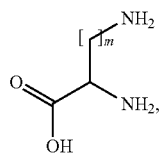

G is glycine, E is glutamate, L is leucine, V is valine, T is threonine, K is lysine, wherein, m is an integer of 1 or more and 4 or less, cysteine at the N-terminal and cysteine at the C-terminal are selectively linked to each other, the Fp is linked via $Y_4$ at amino acid residue 6.

Furthermore, the present application provides an antibody-payload conjugate, wherein B is

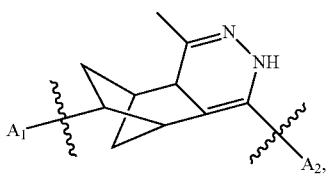

or

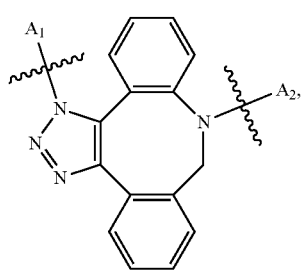

wherein, $A_1$ is linked to the antibody and $A_2$ is linked to Am, or $A_1$ is linked to Am and $A_2$ is linked to the antibody. Furthermore, the present application provides an antibody-payload conjugate, wherein B is

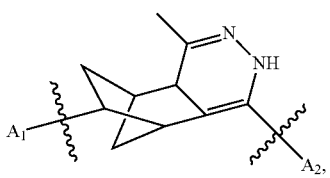

Further, the present application provides an antibody-payload conjugate, wherein Am comprises an anticancer drug. Furthermore, the present application provides an antibody-payload conjugate, wherein the anticancer drug is mertansine (DM1). Further, the present application provides an antibody-payload conjugate, wherein Am comprises two or more anticancer drugs.

Further, the present application provides an antibody-payload conjugate, wherein the nitrogen atom linked to the Ab is contained in lysine 246 or lysine 248 of the Fc of the antibody.

Further, the present application provides an antibody-payload conjugate, wherein n is 2, and the nitrogen atom linked to the Ab is contained in lysine 246 or lysine 248 of both Fcs of the antibody.

In another aspect, the present application provides a pharmaceutical composition for treating cancer, wherein the pharmaceutical composition comprises an antibody-payload comprising an anticancer drug.

Furthermore, the present application provides a pharmaceutical composition, wherein the cancer is breast cancer.

Advantageous Effects

According to the technology disclosed by the present specification, the following effects occur.

Compound 1 disclosed herein provides a linker capable of site-specifically linking a payload to an antibody. The linker has an effect of not affecting biological activity such as the half-life of an antibody, and can be usefully used as bioconjugation for detection, diagnosis, a biomarker, and an anticancer therapeutic.

In addition, Compound 2 disclosed herein provides a linker capable of site-specifically linking a payload to an antibody. The linker can affect the biological activity of a target molecule, and has, for example, an effect of reducing the half-life of a target molecule and/or a payload or promoting excretion. The linker can be usefully used as bioconjugation utilized for detection, diagnosis, and a biomarker.

Furthermore, the antibody-payload conjugates provided by Compounds 1 and 2 have an advantage of having high uniformity due to the uniform binding positions.

BRIEF DESCRIPTION OF THE DRAWINGS

FIGS. 24, 25, 26 and 27 are each the results of cytotoxicity experiments on NCI-N87, BT474, and MDA-MB-468, and a table summarizing the results.

DETAILED DESCRIPTION

Figure 1:
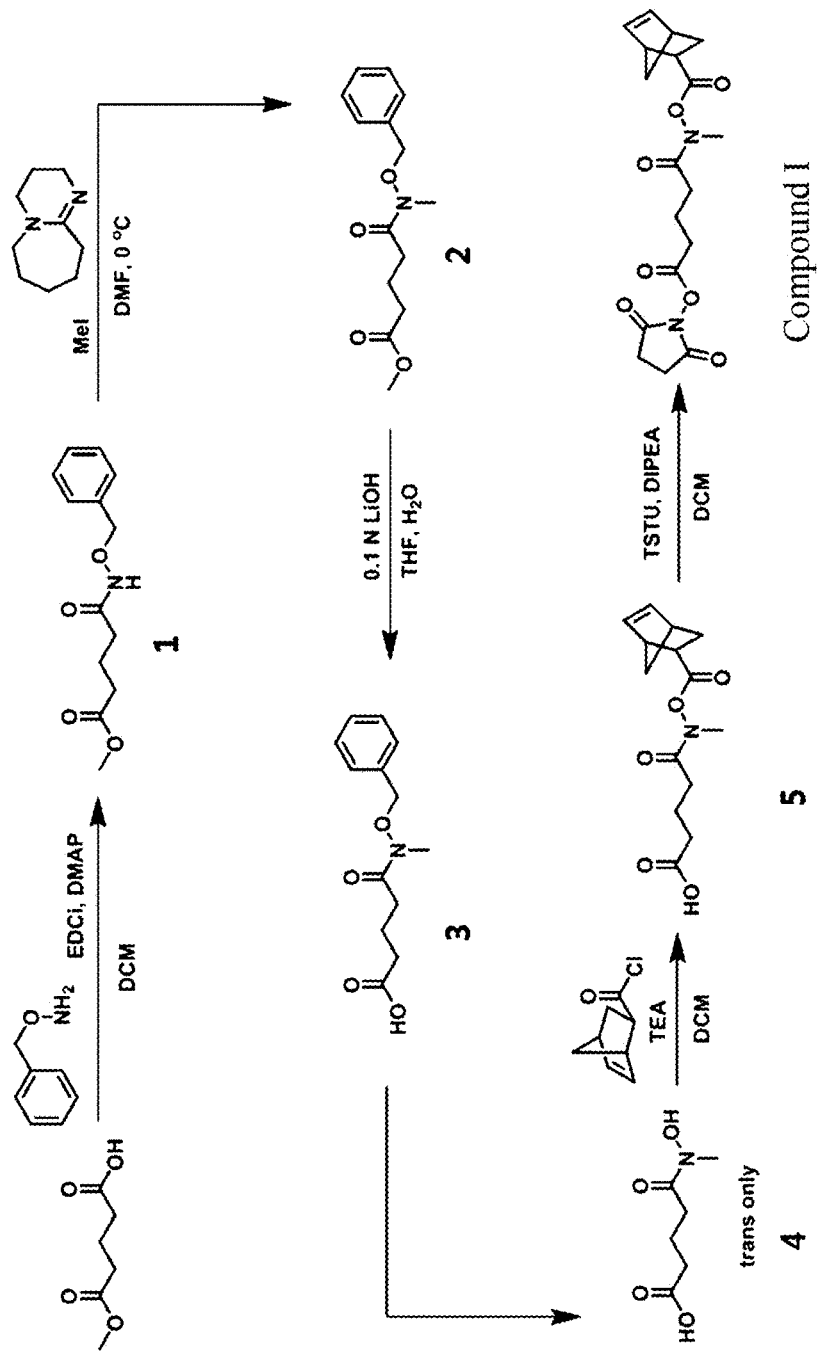
FIG. 1 illustrates an entire synthesis process of Compound I (trans).
Figure 2:
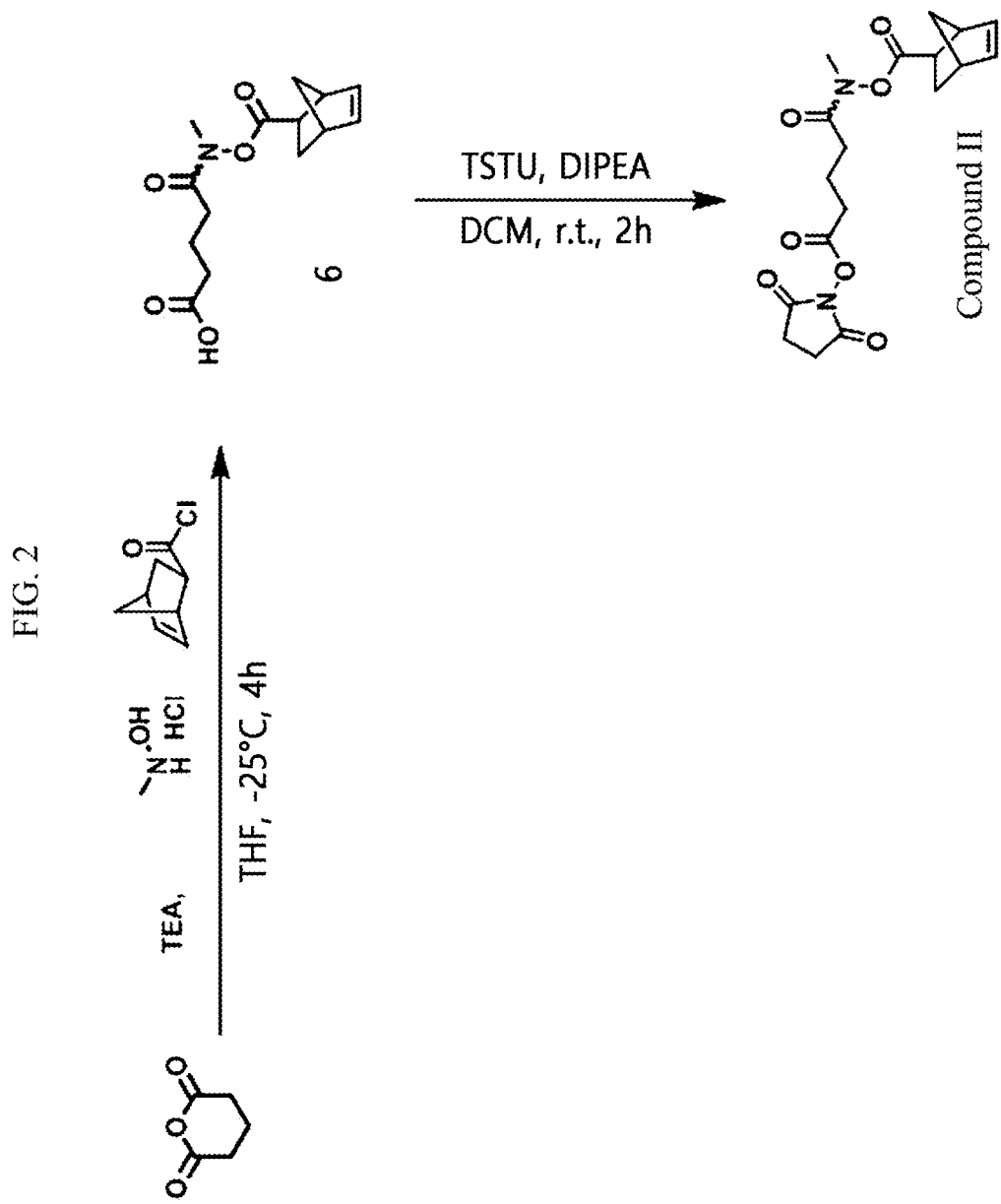
FIG. 2 illustrates an entire synthesis process of Compound II (cis).

The term "heteroalkyl" refers to an alkyl group in which one or more carbon atoms are substituted with a heteroatom such as O, N, or S. For example, when a carbon atom of an alkyl group attached to a parent molecule is substituted with a heteroatom (for example, O, N, or S), the resulting heteroalkyl group is an alkoxy group (for example, —OCH$_3$, and the like), an amine (for example, —NHCH$_3$, —N(CH$_3$)$_2$, and the like), or a thioalkyl group (for example, —SCH$_3$), respectively. When a non-terminal carbon atom of an alkyl group which is not attached to a parent molecule is substituted with a heteroatom (for example, O, N, or S), the resulting heteroalkyl group is an alkyl ether (for example, —CH$_2$CH$_2$—O—CH$_3$, and the like), an alkyl amine (for example, —CH$_2$NHCH$_3$, —CH$_2$N(CH$_3$)$_2$, and the like), or a thioalkyl ether (for example, —CH$_2$—S—CH$_3$), respectively. When a terminal carbon atom of an alkyl group is substituted with a heteroatom (for example, O, N, or S), the resulting heteroalkyl group is a hydroxyalkyl group (for example, —CH$_2$CH$_2$—OH), an aminoalkyl group (for example, —CH$_2$NH$_2$), or an alkyl thiol group (for example, —CH$_2$CH$_2$—SH), respectively. The heteroalkyl group may have, for example, 1 to 20 carbon atoms, 1 to 10 carbon atoms, or 1 to 6 carbon atoms. A C$_1$-C$_6$ heteroalkyl group means a heteroalkyl group having 1 to 6 carbon atoms.

The term "alkylene" refers to a saturated hydrocarbon radical, branched, straight-chain, or cyclic, including two monovalent radical centers, derived by the removal of two hydrogen atoms from the same or two different carbon atom(s) of a parent alkane. For example, the alkylene group may have 1 to 20 carbon atoms, 1 to 10 carbon atoms, or 1 to 6 carbon atoms. A typical alkylene radical includes methylene (—CH$_2$—), 1,1-ethyl (—CH(CH$_3$)—), 1,2-ethyl (—CH$_2$CH$_2$—), 1,1-propyl (—CH(CH$_2$CH$_3$)—), 1,2-propyl (—CH$_2$CH(CH$_3$)—), 1,3-propyl (—CH$_2$CH$_2$CH$_2$—), 1,4-butyl (—CH$_2$CH$_2$CH$_2$CH$_2$—), and the like, but is not limited thereto.

The term "alkenylene" refers to an unsaturated hydrocarbon radical, branched, straight-chain, or cyclic, including two monovalent radical centers, derived by the removal of two hydrogen atoms from the same or two different carbon atom(s) of a parent alkene. For example, the alkenylene group may have 1 to 20 carbon atoms, 1 to 10 carbon atoms, or 1 to 6 carbon atoms. A typical alkenylene group includes 1,2-ethylene (—CH=CH—), but is not limited thereto.

The term "alkynylene" refers to an unsaturated hydrocarbon radical, branched, straight-chain, or cyclic, including two monovalent radical centers, derived by the removal of two hydrogen atoms from the same or two different carbon atom(s) of a parent alkyne. For example, the alkynylene group may have 1 to 20 carbon atoms, 1 to 10 carbon atoms, or 1 to 6 carbon atoms. A typical alkynylene radical includes acetylene (—C≡C—), propargyl (—CH$_2$C≡C—), and 4-pentynyl (—CH$_2$CH$_2$CH$_2$C≡C—), but is not limited thereto.

The term "polymethylene" means an alkylene having one or more carbon atoms, and includes methylene, ethylene, trimethylene, tetramethylene, pentamethylene, hexamethylene, and heptamethylene.

Those skilled in the art will recognize that when a moiety such as "alkyl", "aryl", and "heterocyclyl" is substituted with one or more substituents, these may be selectively referred to as a moiety such as "alkylene", "arylene", and "heterocyclylene" (that is, it means that one or more hydrogen atoms of the parent body "alkyl", "aryl", and "heterocyclyl" moieties are substituted with the mentioned substituent). When a moiety such as "alkyl", "aryl", and "heterocyclyl" is referred as "substituted" in the present application or illustrated as being substituted in the drawings (or being optionally substituted, for example, when the number of substituents is 0 to a positive number), terms such as "alkyl", "aryl", and "heterocyclyl" should be understood as being interchangeable with "alkylene", "arylene", "heterocyclylene", and the like.

The term "acyl" refers to —C(=O)-alkyl, —C(=O)-carbocycle (substituted or unsubstituted), —C(=O)-heterocycle (substituted or unsubstituted), where the alkyl, carbocycle, or heterocycle part thereof is the same as that defined in the present application. Non-limiting examples of the "acyl" include —C(=O)CH$_3$, —C(=O)CH$_2$CH$_3$, —C(=O)CH(CH$_3$)$_2$, —C(=O)C(CH$_3$)$_3$, —C(=O)-phenyl (substituted or unsubstituted), —C(=O)-cyclopropyl (substituted or unsubstituted), —C(=O)-cyclobutyl (substituted or unsubstituted), —C(=O)-cyclopentyl (substituted or unsubstituted), —C(=O)-cyclohexyl (substituted or unsubstituted), —C(=O)-pyridyl (substituted or unsubstituted), and the like.

The terms "substituted", for example, "substituted alkyl", "substituted alkylene", "substituted aryl", "substituted arylalkyl", "substituted heterocyclyl", and "substituted carbocyclyl (for example, substituted cycloalkyl)" mean an alkyl, alkylene, aryl, arylalkyl, heterocyclyl, and carbocyclyl (for example, cycloalkyl), in which one or more hydrogen atoms are each independently substituted with a non-hydrogen substituent, respectively. A typical substituent includes —X, —R, —O—, =O, —OR, —SR, —S—, —NR2, —N+R$_3$, =NR, —C(X)$_3$, —CN, —OCN, —SCN, —N=C=O, —NCS, —NO, —NO$_2$, =N—OH, =N$_2$, —N$_3$, —NHC(=O)R, —C(=O)R, —C(=O)NRR —S(=O)$_2$O—, —S(=O)$_2$OH, —S(=O)$_2$R, —OS(=O)$_2$OR, —S(=O)$_2$NR, —S(=O)R, —OP(=O)(OR)$_2$, —C(=O)R, alkylene-C(=O)R, —C(S)R, —C(=O)OR, alkylene-C(=O)OR, —C(=O)O—, alkylene-C(=O)O—, —C(=S) OR, —C(=O)SR, —C(=S)SR, —C(=O)NRR, alkylene-C(=O)NRR, —C(=S)NRR, —C(=NR)NRR (here, each X is independently a halogen: F, C, Br, or I, and R is independently H, an alkyl, an aryl, an arylalkyl, or a heterocycle), but is not limited thereto. The alkylene, alkenylene, and alkynylene groups may also be similarly substituted.

The "optionally substituted" refers to a particular portion of a compound of Formula 1 having one, two, or more substituents (for example, an optionally substituted aryl group).

The "leaving group" represents a chemical moiety that can be removed or replaced by other chemical groups. Throughout the specification of the present invention, the term leaving group includes a click chemistry functional group, N-hydroxysuccinimide (NHS), or maleimide, but is not limited thereto.

The term "target molecule" or "molecule of interest" means a molecule that is intended to have a payload linked thereto. Exemplarily, the target molecule may be a bioactive molecule, and may be, for example, a protein (or a peptide), a glycan, a nucleic acid (or an oligonucleotide), a lipid, a hormone or a natural drug (or a fragment thereof, or combinations thereof), but is not limited thereto.

The term "payload" means a molecule that is intended to be linked to a target molecule. Exemplarily, the payload may be a compound, a peptide, a polypeptide, a protein, and/or a drug molecule.

The term "click chemistry functional group" collectively refers to a functional group involved in a click chemistry reaction. The type of click chemistry and a functional group involved in the same are typically well known. Examples of the click chemistry reaction include [3+2]cycloadditions, a thiol-ene reaction, a Diels-Alder reaction, an inverse electron demand Diels-Alder reaction, [4+1]cycloadditions, and the like, but are not limited thereto. More specifically, the click chemistry reaction includes a Copper(I)-catalyzed azide-alkyne cycloaddition (CuAAC), a Strain-promoted azide-alkyne cycloaddition (SPAAC), a Strain-promoted alkyne-nitrone cycloaddition (SPANC), a [3+2]cycloaddition of alkene and azide, an inverse-demand Diels-Alder of an alkene and tetrazine, a photoclick reaction of an alkene and tetrazole, and a Huisgen cycloaddition of an azide and an alkyne, but is not limited thereto. The click chemistry functional group includes an alkyne, a cycloalkyne, a cyclooctyne and a cyclononyne (for example, a cycloalkyne such as bicyclo[6.1.0]non-4-yn-9-ylmethanol), a trans-cyclooctene, a nitrone, a nitrile oxide, an azide, a conjugated diene, a dienophile, and a cycloalkyne such as cyclooctyne, cyclononyne, dibenzocyclooctyne (DIBO), biarylazacyclooctynone (BARAC), aryl-less octyne (ALO), difluorinated cyclooctyne (DIFO), monofluorinated (MOFO), dibenzo-aza-cyclooctyne (DIBAC), and dimethoxyazacylooctyne (DIMAC), but is not limited thereto.

The term "ester group activating moiety" collectively refers to a moiety that is linked to an oxygen of an ester group, and thus can convert the ester group to an active ester. For example, when an ester group having a structure of

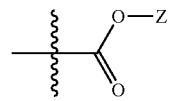

is an active ester, Z is an ester group activating moiety. Exemplarily, the ester group activating moiety includes an N-hydroxysuccinimide group (NHS), a p-nitrophenyl group, and a pentafluorophenyl group, but is not limited thereto. The ester group activating moiety of the present invention includes the content mentioned in WO/2015/122478, but is not limited thereto. The term "active ester" means an ester that is sensitive to a nucleophilic substitution reaction.

In the present specification, terms such as first and second are used to describe various components, and the above terms are used only for the purpose of distinguishing one component from the other.

Further, it should be noted that the terms used in the present specification are merely for describing exemplary embodiments, and are not intended to limit the present invention. Singular expressions include plural expressions unless the context clearly indicates otherwise.

In the present specification, the term such as "comprise", "include" or "have" is intended to indicate the presence of implemented features, numbers, steps, operations, constituent elements, or any combination thereof, and should be understood to mean that the possibility of the presence or addition of one or more other features, numbers, steps, operations, constituent elements, or any combination thereof is not precluded.

Since the present specification may be modified into various forms and include various exemplary embodiments, specific exemplary embodiments will be illustrated and described in detail below. However, the description is not intended to limit the present invention to the specific disclosures, and it is to be understood that all the changes, equivalents and substitutions included in the idea and technical scope of the present invention are included in the present invention.

Hereinafter, the present invention will be described in detail.

The present application may provide a linker that assists in transport and binding reactions such that a payload can be linked to a desired target molecule.

The linker may include two or more functional groups capable of reacting with the payload and/or the target molecule.

The above reaction means that two or more identical or different molecules or some functional groups of the molecule are linked to each other, or a leaving reaction, that is, E1, E2, SN1, SN2 and nucleophilic substitution reactions, and the like occur. The linkage includes all direct or indirect covalent and/or non-covalent bonds.

In an example, a first functional group of the two or more functional groups may be a leaving group.

In an example, a second functional group of the two or more functional groups may be a click chemistry functional group.

The linker may include two or more electrophilic carbon atoms of a carbonyl group.

The electrophilic carbon atom of the carbonyl group may be linked to a functional group.

As an example, the electrophilic carbon atom of the carbonyl group and the functional group may be covalently bonded.

As another example, one or more atoms may be included between the electrophilic carbon atom of the carbonyl group and the functional group. For example, a nucleophilic atom may be included between the electrophilic carbon atom of the carbonyl group and the functional group. In this case, the nucleophilic atom may be O (oxygen), N (nitrogen), or S (sulfur).

The linker may include two or more electrophilic carbon atoms of a carbonyl group, which have different partial positive charges (δ+).

Among the two or more electrophilic carbon atoms of the carbonyl groups, a carbonyl group having the largest partial positive charge (δ+) may be a first carbonyl group carbon atom.

Among the two or more electrophilic carbon atoms of the carbonyl groups, a carbonyl group having the second largest partial positive charge (δ+) may be a second carbonyl group carbon atom.

As an example, the electrophilic carbon atom of the first carbonyl group may be linked to the first functional group. In this case, a nucleophilic atom may be included between the electrophilic carbon atom of the first carbonyl group and the first functional group.

As another example, the electrophilic carbon atom of the second carbonyl group may be linked to the second functional group. In this case, the electrophilic carbon atom of the second carbonyl group may form a covalent bond with the first functional group.

The linker may adjust a position at which a payload to be covalently bound to a target molecule is bound.

For example, the payload may be linked to the electrophilic carbon atom of the first carbonyl group.

The water solubility of the linker may be adjusted by length adjustment. For example, the water solubility of the linker may be increased by increasing the number of alkyl groups including a substituent that may increase the water solubility.

Hereinafter, a linker structure will be described in detail.

According to an aspect disclosed herein, a linker compound represented by the following Formula 1 and/or Formula 2 may be provided.

[Formula 1]
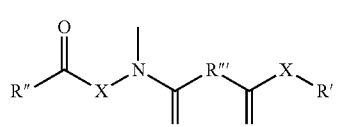

[Formula 2]
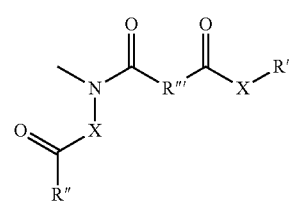

In Formula 1,

R' is an ester group activating moiety. The ester group activating moiety includes an N-hydroxysuccinimide group (NHS), a p-nitrophenyl group, and a pentafluorophenyl group, but is not limited thereto. Furthermore, R' may be any one of

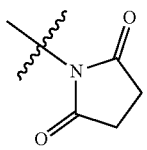 [SMILES: *N1C(=O)CCC1=O]

or

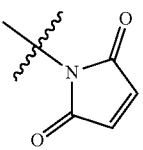

,

R" is any one of click chemistry functional groups, and the click chemistry functional group may be any one or more of an alkyne, a cycloalkyne such as a cyclooctyne and a cyclononyne (for example, bicyclo[6.1.0]non-4-yn-9-yl-methanol), a trans-cyclooctene, a nitrone, a nitrile oxide, an azide, a conjugated diene, and a dienophile, but is not limited thereto.

When the click chemistry functional group is a cycloalkyne, the cycloalkyne may be any one of cyclooctyne, cyclononyne, dibenzocyclooctyne (DIBO), biarylazacyclooctynone (BARAC), aryl-less octyne (ALO), difluorinated cyclooctyne (DIFO), monofluorinated (MOFO), dibenzo-aza-cyclooctyne (DIBAC), and dimethoxyazacyclooctyne (DIMAC). The cycloalkyne is not limited thereto.

When the click chemistry functional group is a conjugated diene, the conjugated diene may be an alkene and a cycloalkane. As an example, the conjugated diene may be a tetrazine (for example, 1,2,3,4-tetrazine and/or 1,2,4,5-tetrazine).

When the click chemistry functional group is a dienophile, the dienophile may be an alkene and a cycloalkane, and the cycloalkane includes a bicyclic or fused cyclic structure. As an example, the dienophile may be norbornene.

R''' is substituted or unsubstituted $C_{1-20}$ alkylene, substituted or unsubstituted $C_{2-20}$ alkenylene, substituted or unsubstituted $C_{1-10}$ alkynylene, substituted or unsubstituted $C_{1-10}$ polymethylene, substituted or unsubstituted $C_{5-12}$ aryl, substituted or unsubstituted $C_{5-14}$ aryl alkylene, substituted or unsubstituted $C_{8-16}$ aryl alkenylene, substituted or unsubstituted $C_{3-10}$ cycloalkylene, substituted or unsubstituted $C_{3-10}$ heterocycloalkylene, or substituted or unsubstituted $C_{5-12}$ heteroaryl, and the heteroalkylene, heterocycloalkylene or heteroaryl includes at least one or more of N, O, or S, and the substitution is substituted with a non-hydrogen substituent, the non-hydrogen substituent is any one or more selected from a group consisting of —Ra, —O—, =O, —ORa, —SRa, —S—, —N(Ra)$_2$, =NRa, —C(Rb)$_3$, —N=C=O, —NCS, —NO, —NO$_2$, =N—OH, =N$_2$, —N$_3$, —NHC(=O)Ra, —C(=O)Ra, —C(=O)NRaRa —S(=O)$_2$O—, —S(=O)$_2$OH, —S(=O)$_2$Ra, —OS(=O)$_2$ORa, —S(=O)$_2$NRa, —S(=O)Ra, —C(=O)Ra, alkylene-C(=O)Ra, —C(=S)Ra, —C(=O)ORa, alkylene-C(=O)ORa, —C(=O)O—, alkylene-C(=O)O—, —C(=S)ORa, —C(=O)SRa, —C(=S)SRa, —C(=O)NRaRa, alkylene-C(=O)NRaRa, —C(=S)NRaRa, —C(=NRa)NRaRa, and Rb, Ra is H, $C_{1-6}$ alkyl, $C_{5-12}$ aryl, $C_{7-12}$ arylalkyl or heterocycle, Rb is F, Cl, Br, or I, X is O, N or S.

In Formula 2,

R' is an ester group activating moiety. The ester group activating moiety includes an N-hydroxysuccinimide group (NHS), a p-nitrophenyl group, and a pentafluorophenyl group, but is not limited thereto. Furthermore, R' may be any one of

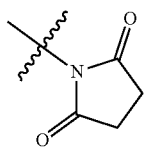 [SMILES: *N1C(=O)CCC1=O]

or

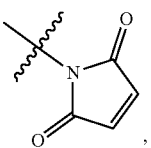,

R'' is any one of click chemistry functional groups, and the click chemistry functional group may be any one or more of an alkyne, a cyclooctyne and a cyclononyne (for example, cycloalkyne such as bicyclo[6.1.0]non-4-yn-9-ylmethanol), a trans-cyclooctene, a nitrone, a nitrile oxide, an azide, a Conjugated Diene, and a dienophile, but not limited thereto.

When the click chemistry functional group is a cycloalkyne, the cycloalkyne may be any one of cyclooctyne, cyclononyne, dibenzocyclooctyne(DIBO), BARAC (biarylazacyclooctynone), ALO(aryl-less octyne), DIFO(difluorinated cyclooctyne), MOFO(monofluorinated), DIBAC (dibenzo-aza-cyclooctyne), and DIMAC (dimethoxyazacylooctyne), but not limited thereto.

When the click chemistry functional group is a conjugated diene, the conjugated diene may be an alkene and a cycloalkane. As an example, the conjugated diene may be a tetrazine (for example, 1,2,3,4-tetrazine and/or 1,2,4,5-tetrazine).

When the click chemistry functional group is a dienophile, the dienophile may be an alkene and a cycloalkane, and the cycloalkane includes a bicyclic or fused cyclic structure. As an example, the dienophile may be transcyclooctene (TCO) or norbornene.

R''' is substituted or unsubstituted $C_{1-20}$ alkylene, substituted or unsubstituted $C_{2-20}$ alkenylene, substituted or unsubstituted $C_{1-10}$ alkynylene, substituted or unsubstituted $C_{1-10}$ polymethylene, substituted or unsubstituted $C_{5-12}$ aryl, substituted or unsubstituted $C_{5-14}$ aryl alkylene, substituted or unsubstituted $C_{8-16}$ aryl alkenylene, substituted or unsubstituted $C_{3-10}$ cycloalkylene, substituted or unsubstituted $C_{3-10}$ heterocycloalkylene, or substituted or unsubstituted $C_{5-12}$ heteroaryl, and the heteroalkylene, heterocycloalkylene or heteroaryl includes at least one or more of N, O, or S, and the substitution is substituted with a non-hydrogen substituent, the non-hydrogen substituent is any one or more selected from a group consisting of —Ra, —O—, =O, —ORa, —SRa, —S—, —N(Ra)$_2$, =NRa, —C(Rb)$_3$, —N=C=O, —NCS, —NO, —NO$_2$, =N—OH, =N$_2$, —N$_3$, —NHC(=O)Ra, —C(=O)Ra, —C(=O)NRaRa —S(=O)$_2$O—, —S(=O)$_2$OH, —S(=O)$_2$Ra, —OS(=O)$_2$ORa, —S(=O)$_2$NRa, —S(=O)Ra, —C(=O)Ra, alkylene-C(=O)Ra, —C(=S)Ra, —C(=O)ORa, alkylene-C(=O)ORa, —C(=O)O—, alkylene-C(=O)O—, —C(=S)ORa, —C(=O)SRa, —C(=S)SRa, —C(=O)NRaRa, alkylene-C(=O)NRaRa, —C(=S)NRaRa, —C(=NRa)NRaRa, and Rb, Ra is H, $C_{1-6}$ alkyl, $C_{5-12}$ aryl, $C_{7-12}$ arylalkyl or heterocycle, Rb is F, Cl, Br, or I, X is O, N or S.

In the Formula of the present invention,

is used to indicate a bond that is an attachment point of a moiety or substituent to a nuclear or skeletal structure.

According to an exemplary embodiment disclosed in the present specification, the compound represented by Formula 1 may be a trans-type compound.

Formula 1 is represented by formula 1-1 below, when formula 1 is same as following:

R' is

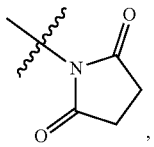

R" is any one of click chemistry functional groups, and the click chemistry functional group is any one or more of an alkyne, a cycloalkyne such as cyclooctyne and a cyclononyne (for example, bicyclo[6.1.0]non-4-yn-9-ylmethanol), a trans-cyclooctene, a nitrone, a nitrile oxide, an azide, a conjugated diene, and a dienophile such as an alkene, and in this case, the cycloalkyne, conjugated diene, and diene are the same as those described above.

R''' is substituted or unsubstituted $C_{1-20}$ alkylene, substituted or unsubstituted $C_{1-20}$ heteroalkylene, substituted or unsubstituted $C_{1-20}$ haloalkyl, or $C_{1-10}$ polymethylene, and the heteroalkylene includes at least one or more selected from a group consisting of N, O, and S, the substitution is substituted with a non-hydrogen substituent, the non-hydrogen substituent is any one or more selected from a group consisting of —Ra, —O—, =O, —ORa, —SRa, —S—, —N(Ra)$_2$, =NRa, —C(Rb)$_3$, —N=C=O, —NCS, —NO, —NO$_2$, =N—OH, =N$_2$, —N$_3$, —NHC(=O)Ra, —C(=O)Ra, —C(=O)NRaRa —S(=O)$_2$O—, —S(=O)$_2$OH, —S(=O)$_2$Ra, —OS(=O)$_2$ORa, —S(=O)$_2$NRa, —S(=O)ORa, —C(=O)Ra, alkylene-C(=O)Ra, —C(=S)Ra, —C(=O)ORa, alkylene-C(=O)ORa, —C(=O)O—, alkylene-C(=O)O—, —C(=S)ORa, —C(=O)SRa, —C(=S)SRa, —C(=O)NRaRa, alkylene-C(=O)NRaRa, —C(=S)NRaRa, —C(=NRa)NRaRa, and Rb, Ra is H, $C_{1-6}$ alkyl, $C_{5-12}$ aryl, $C_{7-12}$ arylalkyl or heterocycle, Rb is F, Cl, Br, or I, and X is any one of O, N, and S.

[Formula 1-1]

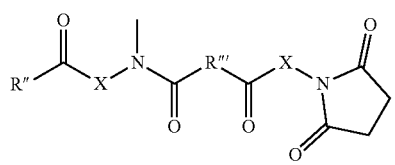

Specifically, R''' is one of

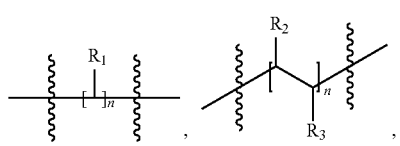

and

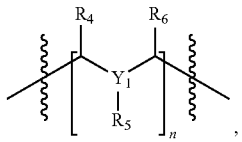

$R_1$ is H,
$R_2$ is H or C(=O),
$R_3$ is H or C(=O),
$R_4$ is H or C(=O),
$R_5$ is H or C(=O),
$R_6$ is H or C(=O),
$Y_1$ may be any one of C, N, O, and S, and
n may be any one of an integer of 1 to 20, but is not limited thereto.
$R_5$ and $R_6$ cannot both be C(=O) at the same time, and when $Y_1$ is any one of N, O, and S, $R_4$, $R_5$, and $R_6$ may not be C(=O).

More specifically, R''' is

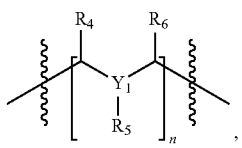

$R_4$ is H or C(=O),
$R_5$ is H or C(=O),
$R_6$ is H or C(=O),
$Y_1$ may be any one of C, N, O, and S, and
n may be any one of an integer of 1 to 10.

In an exemplary embodiment, formula 1-1 is represented by formula 1-1-1 below, when formula 1-1 is same as following:

R' is

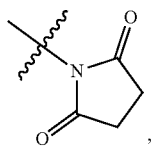

R" is any one of click chemistry functional groups,
R''' is

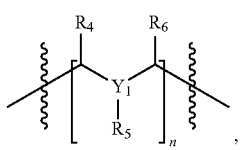

n is 1,
$R_4$ is H or C(=O),
$R_5$ is H or C(=O),
$R_6$ is H or C(=O),
$Y_1$ is C,
and X is any one of N, O, and S.

[Formula 1-1-1]

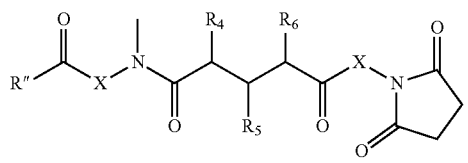

In another exemplary embodiment, formula 1-1 is represented by formula 1-1-2 below, when formula 1-1 is same as following:

R' is

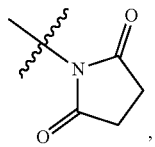

R" is norbornene,
R''' is

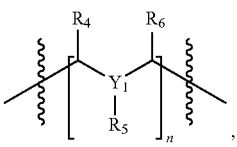

$R_4$ is H,
$R_5$ is H,
$R_6$ is H,
n is 1,
$Y_1$ is C,
and X is O.

[Formula 1-1-2]

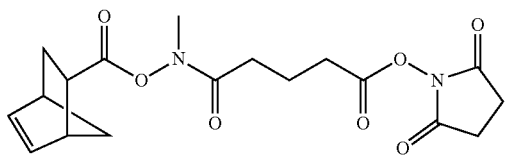

As another exemplary embodiment, the compound which may be represented by Formula 1 may be a compound described in the following Table 1.

TABLE 1

| | |
|---|---|
| Formula 1-1-3 | 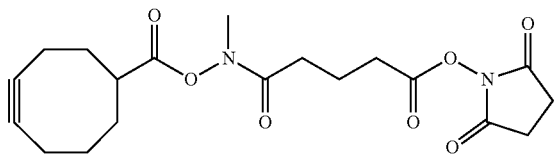 [SMILES: CN(OC(=O)C1CCC#CCCC1)C(=O)CCCC(=O)ON1C(=O)CCC1=O] |
| Formula 1-1-4 | 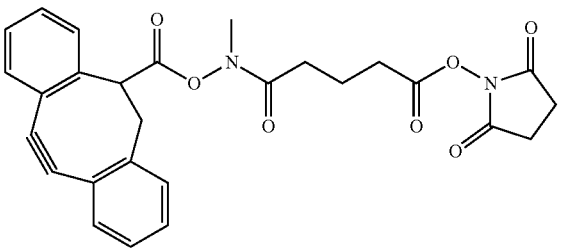 [SMILES: CN(OC(=O)C1Cc2ccccc2C#Cc2ccccc21)C(=O)CCCC(=O)ON1C(=O)CCC1=O] |
| Formula 1-1-5 | 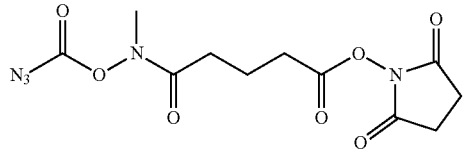 [SMILES: CN(OC(=O)N=[N+]=[N-])C(=O)CCCC(=O)ON1C(=O)CCC1=O] |
| Formula 1-1-6 | 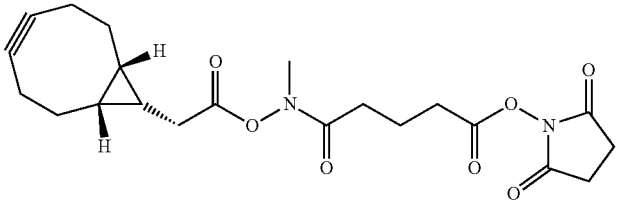 |

TABLE 1-continued

Formula 1-1-7
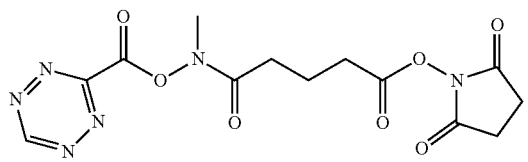 [SMILES: CN(OC(=O)c1nncnn1)C(=O)CCCC(=O)ON1C(=O)CCC1=O]

Formula 1-1-8
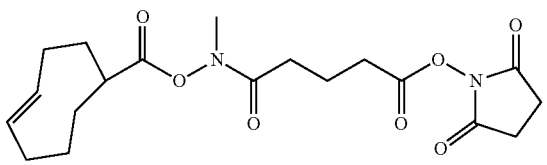 [SMILES: CN(OC(=O)C1CC/C=C/CCC1)C(=O)CCCC(=O)ON1C(=O)CCC1=O]

Formula 1-1-9
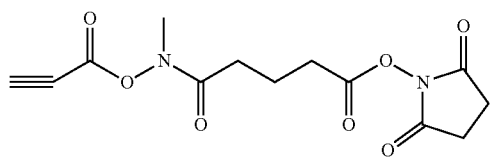 [SMILES: C#CC(=O)ON(C)C(=O)CCCC(=O)ON1C(=O)CCC1=O]

Formula 1-1-10
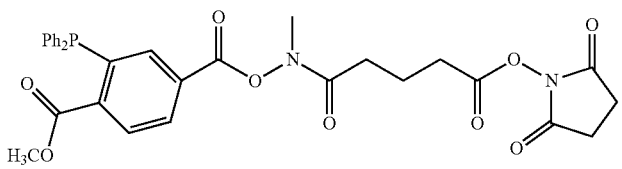

Formula 1-1-11
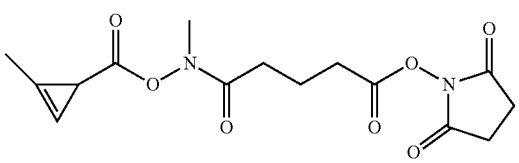 [SMILES: CC1=CC1C(=O)ON(C)C(=O)CCCC(=O)ON1C(=O)CCC1=O]

Formula 1-1-12
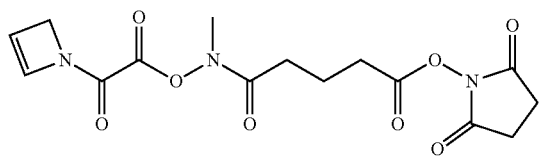 [SMILES: CN(OC(=O)C(=O)N1C=CC1)C(=O)CCCC(=O)ON1C(=O)CCC1=O]

Formula 1-1-13
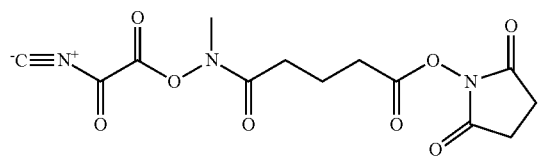

Formula 1 is represented by formula 1-2 below, when formula 1 is same as following:

R' is

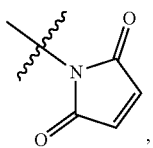

R" is any one of click chemistry functional groups, the click chemistry functional group is any one or more of an alkyne, a cycloalkyne such as a cyclooctyne and a cyclononyne (for example, bicyclo[6.1.0]non-4-yn-9-yl-methanol), a trans-cyclooctene, a nitrone, a nitrile oxide, an azide, a conjugated diene, and a dienophile such as an alkene, and in this case, the cycloalkyne, conjugated diene, and diene are the same as those described above.

R''' is substituted or unsubstituted $C_{1-20}$ alkylene, substituted or unsubstituted $C_{1-20}$ heteroalkylene, substituted or unsubstituted $C_{1-20}$ haloalkyl, or $C_{1-10}$ polymethylene, and the heteroalkylene includes at least one or more selected from a group consisting of N, O, and S, the substitution is substituted with a non-hydrogen substituent, the non-hydrogen substituent is any one or more selected from a group consisting of —Ra, —O—, =O, —ORa, —SRa, —S—, —N(Ra)$_2$, =NRa, —C(Rb)$_3$, —N=C=O, —NCS, —NO, —NO$_2$, =N—OH, =N$_2$, —N$_3$, —NHC(=O)Ra, —C(=O)Ra, —C(=O)NRaRa —S(=O)$_2$O—, —S(=O)$_2$OH, —S(=O)$_2$Ra, —OS (=O)$_2$ORa, —S(=O)$_2$NRa, —S(=O)Ra, —C(=O)Ra, alkylene-C(=O)Ra, —C(=S)Ra, —C(=O)ORa, alkylene- C(=O)ORa, —C(=O)O—, alkylene-C(=O)O—, —C(=S)ORa, —C(=O)SRa, —C(=S)SRa, —C(=O)NRaRa, alkylene-C(=O)NRaRa, —C(=S)NRaRa, —C(=NRa)NRaRa, and Rb, Ra is H, $C_{1-6}$ alkyl, $C_{5-12}$ aryl, $C_{7-12}$ arylalkyl or heterocycle, Rb is F, Cl, Br, or I, and X is any one of O, N, and S.

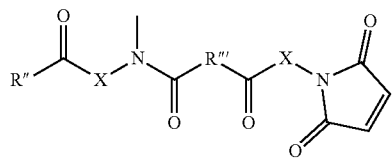
[Formula 1-2]

Specifically, R''' is one of

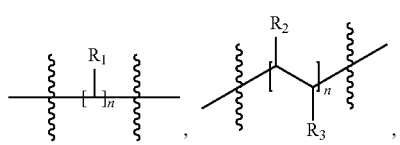

and

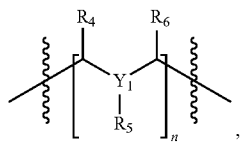

$R_1$ is H,
$R_2$ is H or C(=O),
$R_3$ is H or C(=O),
$R_4$ is H or C(=O),
$R_5$ is H or C(=O),
$R_6$ is H or C(=O),
$Y_1$ may be any one of C, N, O, and S, and
n may be any one of an integer of 1 to 20, but is not limited thereto.

In this case, $R_5$ and $R_6$ cannot both be C(=O), and when $Y_1$ is any one of N, O, and S, $R_4$, $R_5$, and $R_6$ may not be C(=O).

More specifically, R''' is

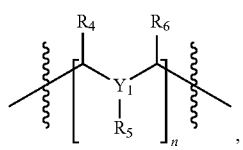

$R_4$ is H or C(=O),
$R_5$ is H or C(=O),
$R_6$ is H or C(=O),
$Y_1$ may be any one of C, N, O, and S, and
n may be any one of an integer of 1 to 10.

In an exemplary embodiment, formula 1-2 is represented by formula 1-2-1 below, when formula 1-2 is same as following:

R''' is

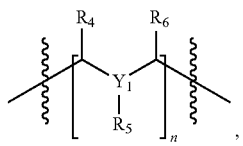

R'' is any one of click chemistry functional groups,
n is 1,
$R_4$ is H or C(=O),
$R_5$ is H or C(=O),
$R_6$ is H or C(=O),
$Y_1$ is C,
and X is any one of N, O, and S.

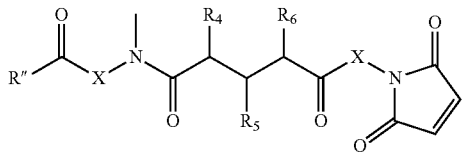
[Formula 1-2-1]

In another exemplary embodiment, formula 1-2 is represented by formula 1-2-2 below, when formula 1-2 is same as following:

R' is

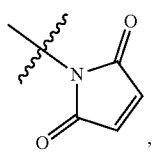

R'' is norbornene,
R''' is

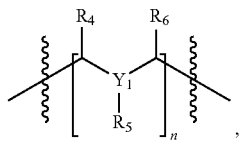

$R_4$ is H,
$R_5$ is H,
$R_6$ is H,
n is 1,
$Y_1$ is C,
and X is O.

[Formula 1-2-2]
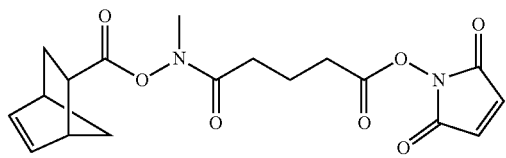
As an exemplary embodiment, the compound which may be represented by Formula 1 may be a compound described in the following Table 2.
TABLE 2
| Formula 1-2-3 | 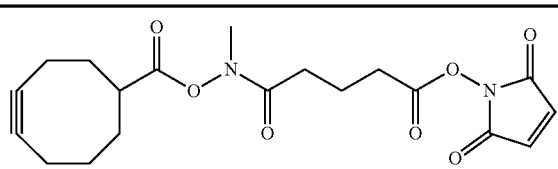 |
| --- | --- |
| Formula 1-2-4 | 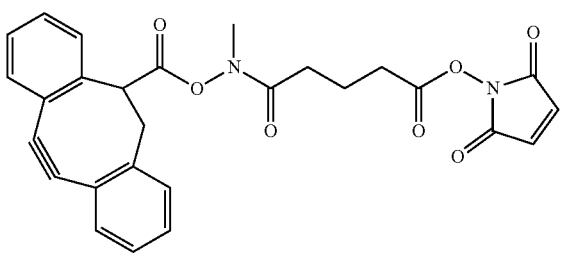 [SMILES: CN(OC(=O)C1Cc2ccccc2C#Cc2ccccc21)C(=O)CCCC(=O)ON1C(=O)C=CC1=O] |
| Formula 1-2-5 | 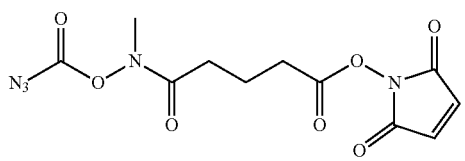 [SMILES: CN(OC(=O)N=[N+]=[N-])C(=O)CCCC(=O)ON1C(=O)C=CC1=O] |
| Formula 1-2-6 | 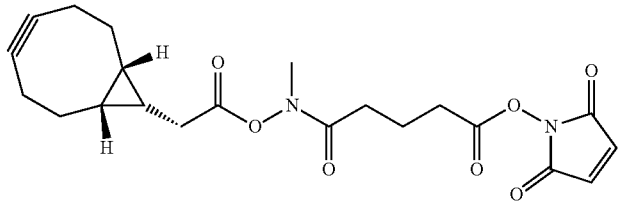 |
| Formula 1-2-7 | 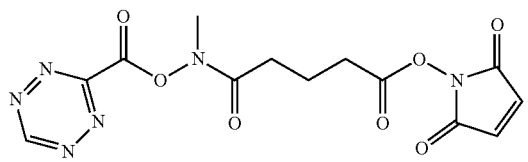 [SMILES: CN(OC(=O)c1nncnn1)C(=O)CCCC(=O)ON1C(=O)C=CC1=O] |
| Formula 1-2-8 | 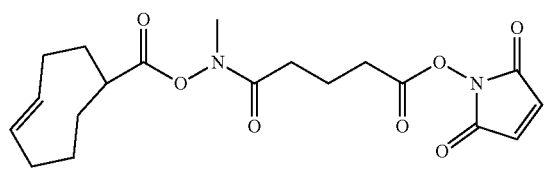 [SMILES: CN(OC(=O)C1CC/C=C/CCC1)C(=O)CCCC(=O)ON1C(=O)C=CC1=O] |
| Formula 1-2-9 | 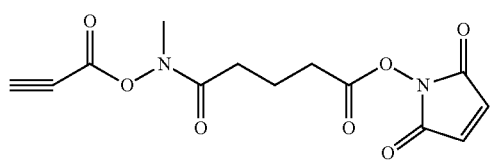 [SMILES: C#CC(=O)ON(C)C(=O)CCCC(=O)ON1C(=O)C=CC1=O] |

TABLE 2-continued

Formula 1-2-10

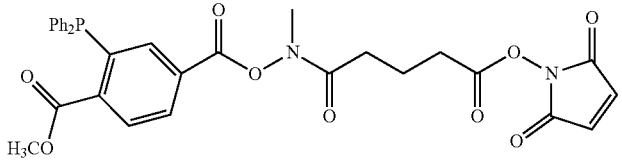

Formula 1-2-11

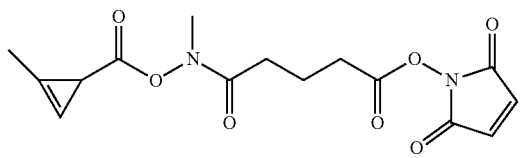 [SMILES: CC1=CC1C(=O)ON(C)C(=O)CCCC(=O)ON1C(=O)C=CC1=O]

Formula 1-2-12

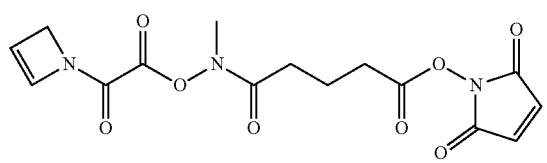 [SMILES: CN(OC(=O)C(=O)N1C=CC1)C(=O)CCCC(=O)ON1C(=O)C=CC1=O]

Formula 1-2-13

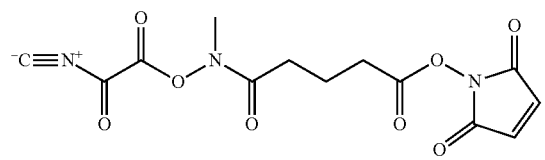

According to an exemplary embodiment disclosed in the present specification, the compound represented by Formula 2 may be a cis-type compound.

Formula 2 is represented by formula 2-1 below, when formula 2 is same as following:

R' is 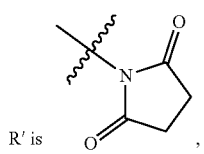 [SMILES: *N1C(=O)CCC1=O],

R'' is any one of click chemistry functional groups,
the click chemistry functional group is any one or more of an alkyne, a cycloalkyne such as a cyclooctyne and a cyclononyne (for example, bicyclo[6.1 0.0]non-4-yn-9-ylmethanol), a trans-cyclooctene, a nitrone, a nitrile oxide, an azide, a conjugated diene, and a dienophile such as an alkene, and in this case, the cycloalkyne, conjugated diene, and diene are the same as those described above.

R''' is substituted or unsubstituted $C_{1-20}$ alkylene, substituted or unsubstituted $C_{1-20}$ heteroalkylene, substituted or unsubstituted $C_{1-20}$ haloalkyl, or $C_{1-10}$ polymethylene, and the heteroalkylene includes at least one or more selected from a group consisting of N, O, and S, the substitution is substituted with a non-hydrogen substituent, the non-hydrogen substituent is any one or more selected from a group consisting of —Ra, —O—, =O, —ORa, —SRa, —S—, —N(Ra)$_2$, =NRa, —C(Rb)$_3$, —N=C=O, —NCS, —NO, —NO$_2$, =N—OH, =N$_2$, —N$_3$, —NHC(=O)Ra, —C(=O)Ra, —C(=O)NRaRa —S(=O)$_2$O—, —S(=O)$_2$OH, —S(=O)$_2$Ra, —OS(=O)$_2$ORa, —S(=O)$_2$NRa, —S(=O)Ra, —C(=O)Ra, alkylene-C(=O)Ra, —C(=S)Ra, —C(=O)ORa, alkylene-C(=O)ORa, —C(=O)O—, alkylene-C(=O)O—, —C(=S)ORa, —C(=O)SRa, —C(=S)SRa, —C(=O)NRaRa, alkylene-C(=O)NRaRa, —C(=S)NRaRa, —C(=NRa)NRaRa, and Rb, Ra is H, $C_{1-6}$ alkyl, $C_{5-12}$ aryl, $C_{7-12}$ arylalkyl or heterocycle, Rb is F, Cl, Br, or I, and X is any one of O, N, and S.

[Formula 2-1]

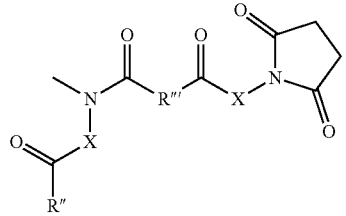

Specifically, R''' is one of

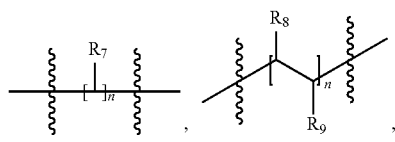

and

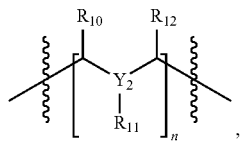

$R_7$ is H,
$R_8$ is H or C(=O),
$R_9$ is H or C(=O),
$R_{10}$ is H or C(=O),
$R_{11}$ is H or C(=O),
$R_{12}$ is H or C(=O),
$Y_2$ may be any one of C, N, O, and S, and
n may be any one of an integer of 1 to 20, but is not limited thereto.
In this case, $R_{11}$ and $R_{12}$ cannot both be C(=O), and when $Y_2$ is any one of N, O, and S, $R_{10}$, $R_{11}$, and $R_{12}$ may not be C(=O).
More specifically, R''' is

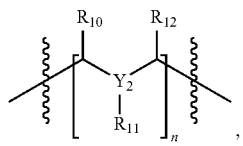

$R_{10}$ is H or C(=O),
$R_{11}$ is H or C(=O),
$R_{12}$ is H or C(=O),
$Y_2$ may be any one of C, N, O, and S, and
n may be any one of an integer of 1 to 10.
In an exemplary embodiment, formula 2-1 is represented by formula 2-1-1 below, when formula 2-1 is same as following:
R' is

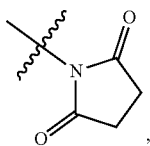

R'' is any one of click chemistry functional groups,
R''' is

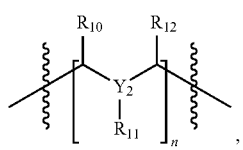

n is 1,
$R_{10}$ is H or C(=O),
$R_{11}$ is H or C(=O),
$R_{12}$ is H or C(=O),
$Y_2$ is C,
and X is any one of N, O, and S.

[Formula 2-1-1]

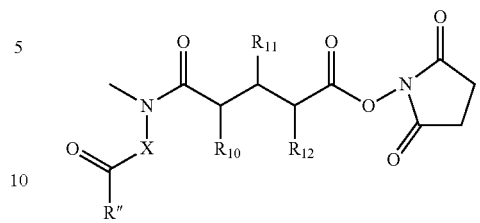

In another exemplary embodiment, formula 2-1 is represented by formula 2-1-2 below, when formula 2-1 is same as following:
R' is

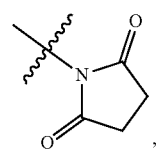

R'' is norbornene,

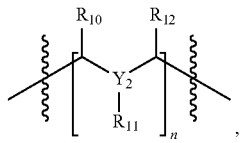

R''' is
n is 1,
$R_{10}$ is H,
$R_{11}$ is H,
$R_{12}$ is H,
$Y_2$ is C,
n is 1, and
X is O.

[Formula 2-1-2]

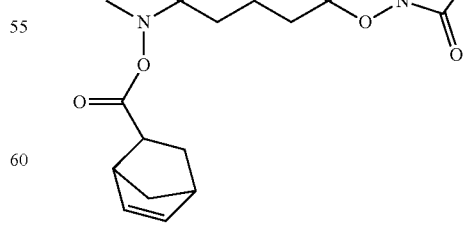

As an exemplary embodiment, the compound which may be represented by Formula 2 may be a compound described in the following Table 3.

TABLE 3
Formula 2-1-3 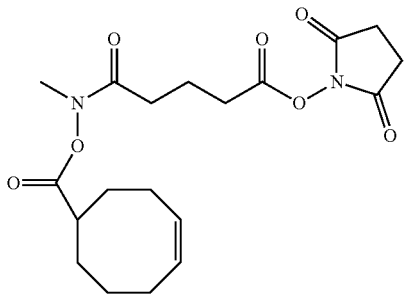 [SMILES: CN(OC(=O)C1CC/C=C\CCC1)C(=O)CCCC(=O)ON1C(=O)CCC1=O]
Formula 2-1-4 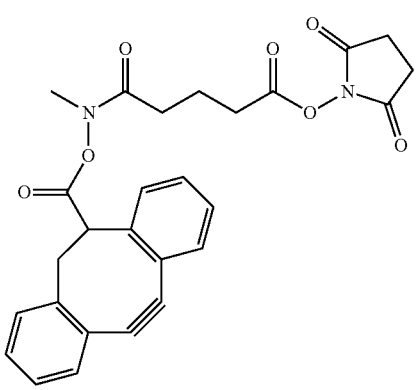 [SMILES: CN(OC(=O)C1Cc2ccccc2C#Cc2ccccc21)C(=O)CCCC(=O)ON1C(=O)CCC1=O]
Formula 2-1-5 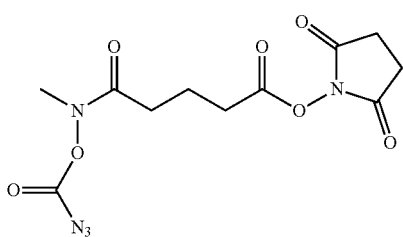 [SMILES: CN(OC(=O)N=[N+]=[N-])C(=O)CCCC(=O)ON1C(=O)CCC1=O]
Formula 2-1-6 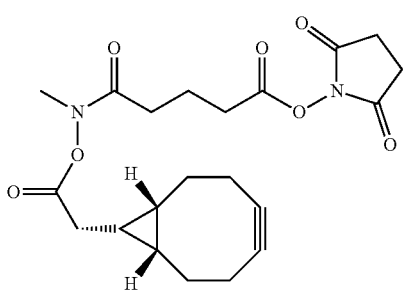
Formula 2-1-7 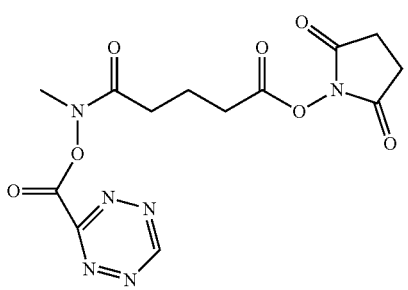 [SMILES: CN(OC(=O)c1nncnn1)C(=O)CCCC(=O)ON1C(=O)CCC1=O]
TABLE 3-continued
Formula 2-1-8 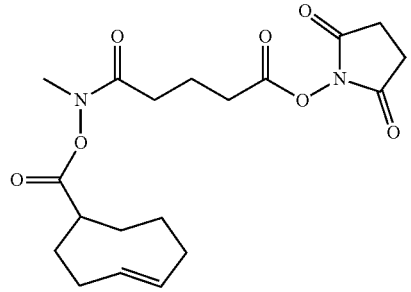 [SMILES: CN(OC(=O)C1CC/C=C/CCC1)C(=O)CCCC(=O)ON1C(=O)CCC1=O]
Formula 2-1-9 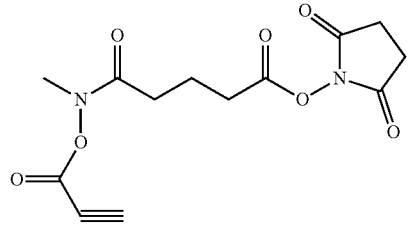 [SMILES: C#CC(=O)ON(C)C(=O)CCCC(=O)ON1C(=O)CCC1=O]
Formula 2-1-10 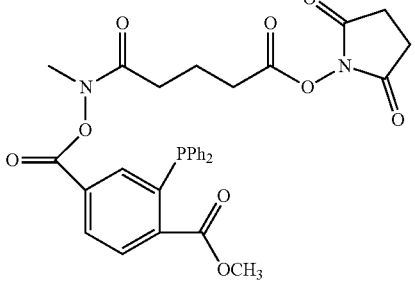
Formula 2-1-11 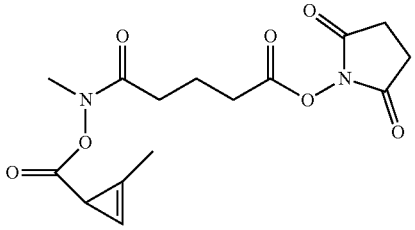 [SMILES: CC1=CC1C(=O)ON(C)C(=O)CCCC(=O)ON1C(=O)CCC1=O]
Formula 2-1-12 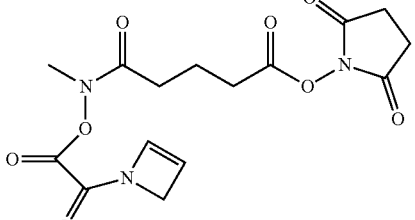
Formula 2-1-13 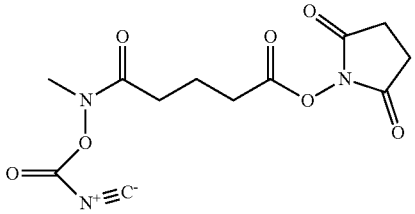 [SMILES: [C-]#[N+]C(=O)ON(C)C(=O)CCCC(=O)ON1C(=O)CCC1=O]

Formula 2 is represented by formula 2-2 below, when formula 2 is same as following:

R' is

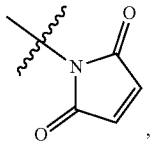

R'' is any one of click chemistry functional groups, the click chemistry functional group is any one or more of an alkyne, a cycloalkyne such as a cyclooctyne and a cyclononyne (for example, bicyclo[6.1.0]non-4-yn-9-ylmethanol), a trans-cyclooctene, a nitrone, a nitrile oxide, an azide, a conjugated diene, and a dienophile such as an alkene, and in this case, the cycloalkyne, conjugated diene, and diene are the same as those described above.

R''' is substituted or unsubstituted $C_{1-20}$ alkylene, substituted or unsubstituted $C_{1-20}$ heteroalkylene, substituted or unsubstituted $C_{1-20}$ haloalkyl, or $C_{1-10}$ polymethylene, and the heteroalkylene includes at least one or more selected from a group consisting of N, O, and S, the substitution is substituted with a non-hydrogen substituent, the non-hydrogen substituent is any one or more selected from a group consisting of —Ra, —O—, =O, —ORa, —SRa, —S—, —N(Ra)$_2$, =NRa, —C(Rb)$_3$, —N=C=O, —NCS, —NO, —NO$_2$, =N—OH, =N$_2$, —N$_3$, —NHC(=O)Ra, —C(=O)Ra, —C(=O)NRaRa —S(=O)$_2$O—, —S(=O)$_2$OH, —S(=O)$_2$Ra, —OS(=O)$_2$ORa, —S(=O)$_2$NRa, —S(=O)Ra, —C(=O)Ra, alkylene-C(=O)Ra, —C(=S)Ra, —C(=O)ORa, alkylene-C(=O)ORa, —C(=O)O—, alkylene-C(=O)O—, —C(=S)ORa, —C(=O)SRa, —C(=S)SRa, —C(=O)NRaRa, alkylene-C(=O)NRaRa, —C(=S)NRaRa, —C(=NRa)NRaRa, and Rb, Ra is H, $C_{1-6}$ alkyl, $C_{5-12}$ aryl, $C_{7-12}$ arylalkyl or heterocycle, Rb is F, Cl, Br, or I, and X is any one of O, N, and S.

[Formula 2-2]

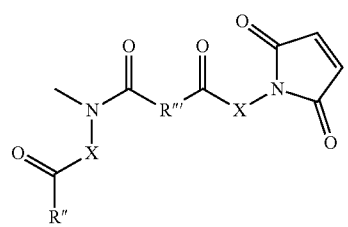

Specifically, R''' is one of

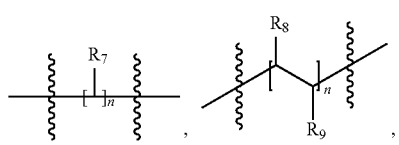

and

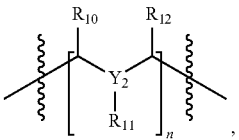

$R_7$ is H,
$R_8$ is H or C(=O),
$R_9$ is H or C(=O),
$R_{10}$ is H or C(=O),
$R_{11}$ is H or C(=O),
$R_{12}$ is H or C(=O),
$Y_2$ may be any one of C, N, O, and S, and
n may be any one of an integer of 1 to 20, but is not limited thereto.

In this case, $R_{11}$ and $R_{12}$ cannot both be C(=O), and when $Y_2$ is any one of N, O, and S, $R_{10}$, $R_{11}$, and $R_{12}$ may not be C(=O).

More specifically, R''' is

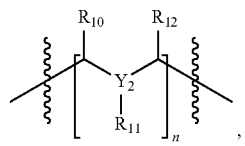

$R_{10}$ is H or C(=O),
$R_{11}$ is H or C(=O),
$R_{12}$ is H or C(=O),
$Y_2$ may be any one of C, N, O, and S, and
n may be any one of an integer of 1 to 10.

In an exemplary embodiment, formula 2-2 is represented by formula 2-2-1 below, when formula 2-2 is same as following:

R' is

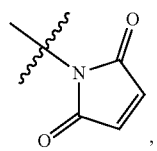

R'' is any one of click chemistry functional groups,
R''' is

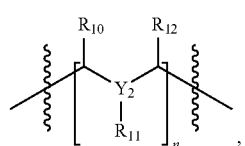

n is 1,
$R_{10}$ is H or C(=O),
$R_{11}$ is H or C(=O),
$R_{12}$ is H or C(=O),
$Y_2$ is C,
and X is any one of N, O, and S.

[Formula 2-2-1]

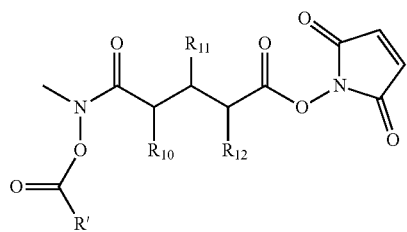

In another exemplary embodiment, formula 2-2 is represented by formula 2-2-2 below, when formula 2-2 is same as following:

R' is,

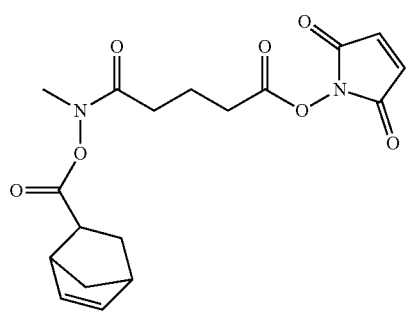

R" is norbornene,
R'" is n is 1,
$R_{10}$ is H,
$R_{11}$ is H,
$R_{12}$ is H,
$Y_2$ is C, and
X is O.

[Formula 2-2-2]

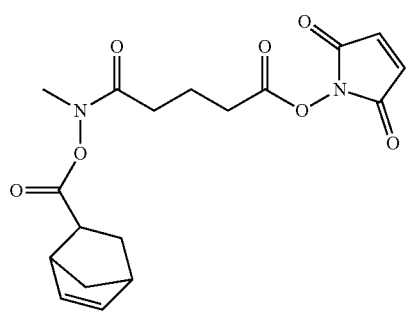

As an exemplary embodiment, the compound which may be represented by Formula 2, may be a compound described in the following Table 4.

TABLE 4

Formula 2-2-3

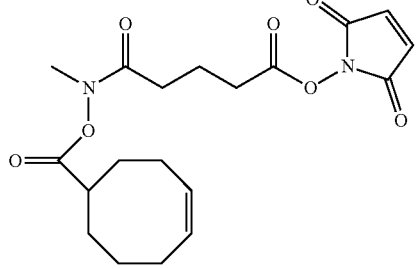

Formula 2-2-4

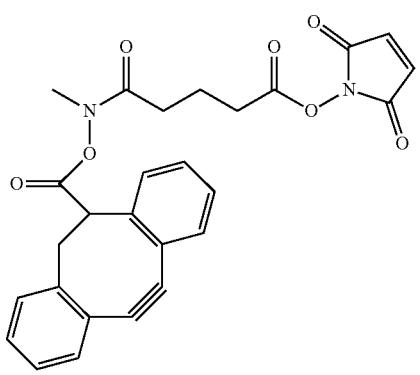 [SMILES: CN(OC(=O)C1Cc2ccccc2C#Cc2ccccc21)C(=O)CCCC(=O)ON1C(=O)C=CC1=O]

Formula 2-2-5

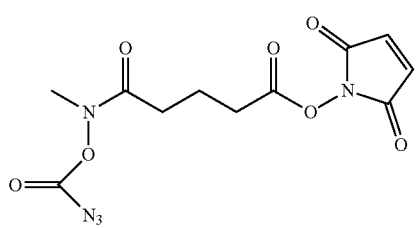 [SMILES: CN(OC(=O)N=[N+]=[N-])C(=O)CCCC(=O)ON1C(=O)C=CC1=O]

Formula 2-2-6

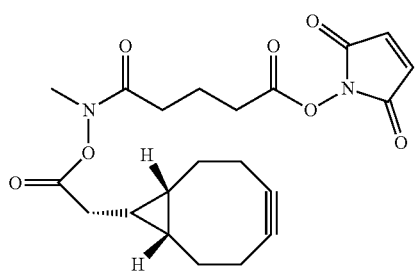

Formula 2-2-7

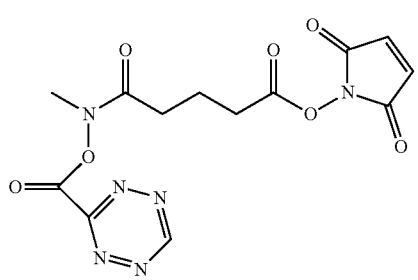 [SMILES: CN(OC(=O)c1nncnn1)C(=O)CCCC(=O)ON1C(=O)C=CC1=O]

TABLE 4-continued

Formula 2-2-8
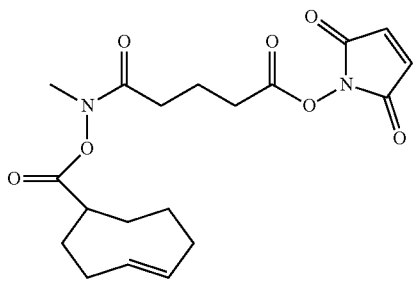 [SMILES: CN(OC(=O)C1CC/C=C/CCC1)C(=O)CCCC(=O)ON1C(=O)C=CC1=O]

Formula 2-2-9
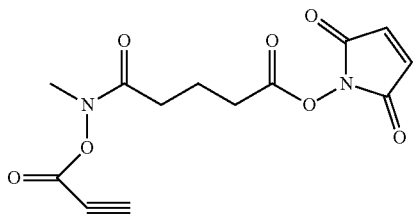 [SMILES: C#CC(=O)ON(C)C(=O)CCCC(=O)ON1C(=O)C=CC1=O]

Formula 2-2-10
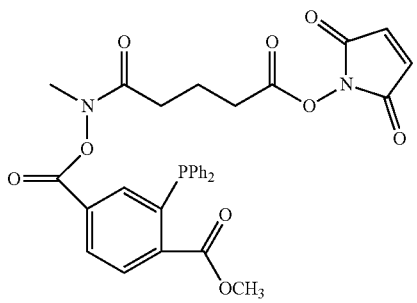

Formula 2-2-11
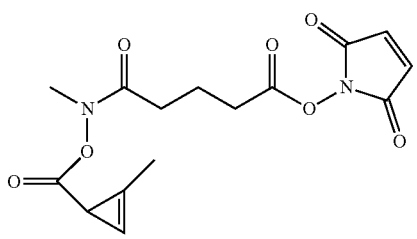 [SMILES: CC1=CC1C(=O)ON(C)C(=O)CCCC(=O)ON1C(=O)C=CC1=O]

Formula 2-2-12
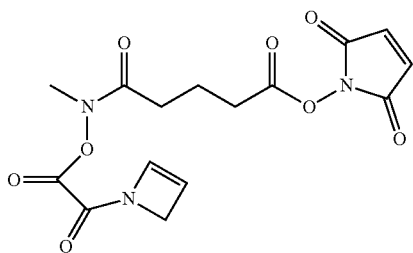 [SMILES: CN(OC(=O)C(=O)N1C=CC1)C(=O)CCCC(=O)ON1C(=O)C=CC1=O]

Formula 2-2-13
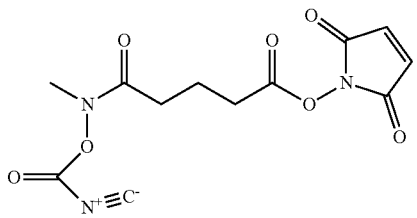 [SMILES: [C-]#[N+]C(=O)ON(C)C(=O)CCCC(=O)ON1C(=O)C=CC1=O]

Hereinafter, when the target molecule is an antibody, a method for preparing an antibody-payload conjugate using the linker described above will be described. The method for preparing an antibody-payload conjugate, the method comprising: (1) preparing a linker-Fc binding peptide conjugate by reacting a linker with a Fc binding peptide; (2) reacting the linker-Fc binding peptide conjugate with an antibody to obtain an antibody comprising the first click-chemistry functional group, and (3) preparing the antibody-payload conjugate by reacting the antibody comprising the first click chemistry functional group with a payload comprising a second click chemistry functional group complementary to the first click chemistry functional group. Hereinafter, each process will be dividedly described.

The method for preparing an antibody-payload conjugate may comprise: (1) preparing a linker-Fc binding peptide conjugate by reacting a linker with a Fc binding peptide.

The Fc binding peptide collectively refers to a peptide having a property of binding to the Fc domain of an antibody. As a representative example of the Fc binding peptide, a 13-mer peptide discovered by DeLano et al., which is known to have a property of binding to the FcRn domain, is well known. The inventors of the present invention invented Fc binding peptides of SEQ ID NOS: 1 to 5 in which a specific residue of the 13-mer peptide was substituted, and enabled the Fc binding peptides to react with a linker. As can be seen in the following structure, the Fc binding peptides of SEQ ID NOS: 1 to 5 can react with the linker via a free amine group included in residue 6.

The Fc binding peptide by SEQ ID NO: 1 is a peptide represented by Formula 13:

$$\text{D—C—A—W—H—Xa—G—E—L—V—W—C—T(SEQ ID NO:1)} \quad \text{[Formula 13]}$$

wherein, D is aspartic acid, C is cysteine, A is alanine, W is tryptophan, H is histidine, Xa is

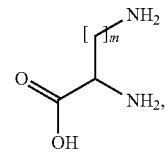

G is glycine, E is glutamate, L is leucine, V is valine, and T is threonine. In this case, m is an integer of 1 or more and 4 or less, and cysteine at the N-terminal and cysteine at the C-terminal may be selectively linked to each other. Xa is 2,3-diaminopropionic acid (Dap) when m=1 (SEQ ID NO: 3), Xa is 2,4-diaminobutyric acid (Dab) when m=2 (SEQ ID NO: 4), Xa is ornithine when m=3 (SEQ ID NO: 5), and Xa is lysine when m=4 (SEQ ID NO: 2).

The Fc binding peptide by SEQ ID NO: 2 is a peptide represented by Formula 14:

$$\text{D—C—A—W—H—K—G—E—L—V—W—C—T} \quad \text{[Formula 14]}$$
$$\text{(SEQ ID NO:2)}$$

wherein, D is aspartic acid, C is cysteine, A is alanine, W is tryptophan, H is histidine, K is lysine, G is glycine, E is glutamate, L is leucine, V is valine, T is threonine, and cysteine at the N-terminal and cysteine at the C-terminal may be selectively linked to each other.

The linker includes the compound according to chemical Formula 1 or chemical Formula 2 and specific examples thereof.

The linker and the Fc binding peptide may be bound by a nucleophilic substitution reaction. Wherein, the nucleophilic substitution reaction may occur when the nucleophilic atom present in the Fc binding peptide attacks a positively charged or a partially positively charged atom of the linker.

Wherein, the nucleophilic atom may be a nitrogen atom of lysine. In addition, the positively charged or partially positively charged atom may be an electrophilic carbon of a carbonyl group.

In the following, it is shown that a compound represented by Formulas 1 and/or 2, which are exemplarily disclosed by the present specification, that is, a linker, binds to an Fc binding peptide to form a linker-Fc binding peptide conjugate.

Exemplarily, the linker-Fc binding peptide conjugate may have a structure of Formula 3.

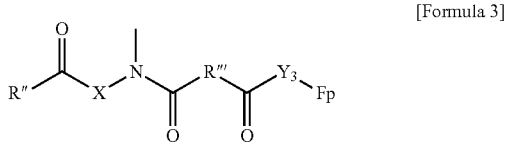

[Formula 3]

In Formula 3,

R" is any one of click chemistry functional groups, the click chemistry functional group is any one or more of an alkyne, a cycloalkyne such as a cyclooctyne and a cyclononyne (for example, bicyclo[6.1.0]non-4-yn-9-ylmethanol), a trans-cyclooctene, a nitrone, a nitrile oxide, an azide, a conjugated diene, and a dienophile, and in this case, the cycloalkyne, conjugated diene, and diene are the same as those described above.

R'" is substituted or unsubstituted $C_{1-20}$ alkylene, substituted or unsubstituted $C_{2-20}$ alkenylene, substituted or unsubstituted $C_{1-10}$ alkynylene, substituted or unsubstituted $C_{1-10}$ polymethylene, substituted or unsubstituted $C_{5-12}$ aryl, substituted or unsubstituted $C_{5-14}$ aryl alkylene, substituted or unsubstituted $C_{8-16}$ aryl alkenylene, substituted or unsubstituted $C_{3-10}$ cycloalkylene, substituted or unsubstituted $C_{3-10}$ heterocycloalkylene, or substituted or unsubstituted $C_{5-12}$ heteroaryl, and the heteroalkylene, heterocycloalkylene or heteroaryl includes at least one or more of N, O, or S, and the substitution is substituted with a non-hydrogen substituent, the non-hydrogen substituent is any one or more selected from a group consisting of —Ra, —O—, =O, —ORa, —SRa, —S—, —N(Ra)₂, =NRa, —C(Rb)₃, —N=C=O, —NCS, —NO, —NO₂, =N—OH, =N₂, —N₃, —NHC(=O)Ra, —C(=O)Ra, —C(=O)NRaRa —S(=O)₂O—, —S(=O)₂OH, —S(=O)₂Ra, —OS(=O)₂ORa, —S(=O)₂NRa, —S(=O)Ra, —C(=O)Ra, alkylene-C(=O)Ra, —C(=S)Ra, —C(=O)ORa, alkylene-C(=O)ORa, —C(=O)O—, alkylene-C(=O)O—, —C(=S)ORa, —C(=O)SRa, —C(=S)SRa, —C(=O)NRaRa, alkylene-C(=O)NRaRa, —C(=S)NRaRa, —C(=NRa)NRaRa, and Rb, Ra is H, $C_{1-6}$ alkyl, $C_{5-12}$ aryl, $C_{7-12}$ arylalkyl or heterocycle, Rb is F, Cl, Br, or I, X may be O, N or S.

$Y_3$ may be any one of O, N, and S.

Fp is a Fc binding peptide. Furthermore, Fp may be any one peptide selected from Formula 13 or 14. Details about Formulas 13 and 14 are the same as those already described.

The Fp may be linked via $Y_3$ at an amino acid residue 6. In this case, the amino acid residue 6 may be lysine, ornithine, 2,3-diaminopropionic acid, or 2,4-diaminobutyric acid.

The compound represented by Formula 3 may be produced by Reaction Scheme 1 as an example.

[Reaction Scheme 1]

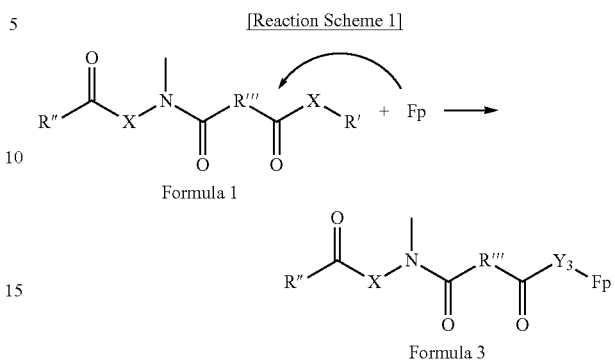

Formula 1

Formula 3

Reaction Scheme 1 is a reaction for producing a compound represented by Formula 3 by reacting the compound represented by Formula 1 with a Fc binding peptide including 1 to 50 amino acids.

The binding reaction between the Fc binding peptide and Formula 1 may be performed by a substitution reaction.

The substitution reaction may be a nucleophilic acyl substitution reaction.

The substitution reaction may be performed by a reaction between the compound of Formula 1 and any one of an amine group (—NH₂), thiol group (—SH), and hydroxy group (—OH) of the Fc binding peptide.

As an example, when the compound of Formula 1 is reacted with an amine group (—NH₂) of the Fc binding peptide, $Y_3$ may be N(H). As peptides of SEQ ID NOS: 1 to 5 include 2,3-diaminopropionic acid, 2,4-diaminobutyric acid, ornithine, or lysine at residue 6, all the corresponding residues include free amine groups so that a substitution reaction may be performed.

As another example, when the compound of Formula 1 is reacted with a thiol group (—SH) of the Fc binding peptide, $Y_3$ may be S.

As an example, when the compound of Formula 1 is reacted with any one of the hydroxy groups (—OH) of the Fc binding peptide, $Y_3$ may be O.

Exemplarily, the linker-Fc binding peptide conjugate may have a structure of Formula 4.

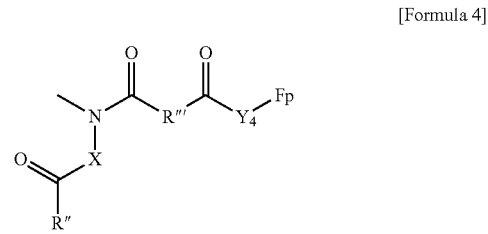

[Formula 4]

In Formula 4,

R" is any one of click chemistry functional groups, the click chemistry functional group is any one or more of an alkyne, a cycloalkyne such as a cyclooctyne and a cyclononyne (for example, bicyclo[6.1.0]non-4-yn-9-ylmethanol), a trans-cyclooctene, a nitrone, a nitrile oxide, an azide, a conjugated diene, and a dienophile, and wherein, the cycloalkyne, conjugated diene, and diene are the same as those described above.

R''' is substituted or unsubstituted $C_{1-20}$ alkylene, substituted or unsubstituted $C_{2-20}$ alkenylene, substituted or unsubstituted $C_{1-10}$ alkynylene, substituted or unsubstituted $C_{1-10}$ polymethylene, substituted or unsubstituted $C_{5-12}$ aryl, substituted or unsubstituted $C_{5-14}$ aryl alkylene, substituted or unsubstituted $C_{8-16}$ aryl alkenylene, substituted or unsubstituted $C_{3-10}$ cycloalkylene, substituted or unsubstituted $C_{3-10}$ heterocycloalkylene, or substituted or unsubstituted $C_{5-12}$ heteroaryl, and the heteroalkylene, heterocycloalkylene or heteroaryl includes at least one or more of N, O, or S, and the substitution is substituted with a non-hydrogen substituent, the non-hydrogen substituent is any one or more selected from a group consisting of —Ra, —O—, =O, —ORa, —SRa, —S—, —N(Ra)$_2$, =NRa, —C(Rb)$_3$, —N=C=O, —NCS, —NO, —NO$_2$, =N—OH, =N$_2$, —N$_3$, —NHC(=O)Ra, —C(=O)Ra, —C(=O)NRaRa —S(=O)$_2$O—, —S(=O)$_2$OH, —S(=O)$_2$Ra, —OS(=O)$_2$ORa, —S(=O)$_2$NRa, —S(=O)Ra, —C(=O)Ra, alkylene-C(=O)Ra, —C(=S)Ra, —C(=O)ORa, alkylene-C(=O)ORa, —C(=O)O—, alkylene-C(=O)O—, —C(=S)ORa, —C(=O)SRa, —C(=S)SRa, —C(=O)NRaRa, alkylene-C(=O)NRaRa, —C(=S)NRaRa, —C(=NRa)NRaRa, and Rb, Ra is H, $C_{1-6}$ alkyl, $C_{5-12}$ aryl, $C_{7-12}$ arylalkyl or heterocycle, Rb is F, Cl, Br, or I, X may be O, N or S.

$Y_4$ may be any one of O, N, and S.

Fp is a Fc binding peptide. Furthermore, Fp may be any one peptide selected from Formula 13 or 14. Details about Formulas 13 and 14 are the same as those already described.

The Fp may be linked via $Y_4$ at amino acid residue 6. In this case, the amino acid residue 6 may be lysine, ornithine, 2,3-diaminopropionic acid, or 2,4-diaminobutyric acid.

The compound represented by Formula 4 may be produced by Reaction Scheme 2 as an example.

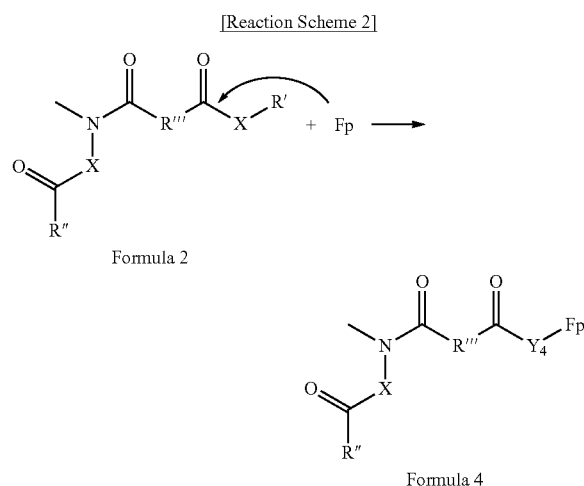

Formula 2

Formula 4

Reaction Scheme 2 is a reaction for producing a compound represented by Formula 4 by reacting the compound represented by Formula 2 with a Fc binding peptide including 1 to 50 amino acids.

The reaction between the Fc binding peptide and Formula 2 may be performed by a substitution reaction.

The substitution reaction may be a nucleophilic acyl substitution reaction.

The substitution reaction may be performed by a reaction between the compound of Formula 2 and any one of an amine group (—NH$_2$), thiol group (—SH), and hydroxy group (—OH) of the Fc binding peptide.

As an example, when the compound of Formula 2 is reacted with an amine group (—NH$_2$) of the Fc binding peptide, $Y_4$ may be N. As peptides of SEQ ID NOS: 1 to 5 include 2,3-diaminopropionic acid, 2,4-diaminobutyric acid, ornithine, or lysine at a residue 6, all the corresponding residues include free amine groups so that a substitution reaction may be performed.

As another example, when the compound of Formula 2 is reacted with a thiol group (—SH) of the Fc binding peptide, $Y_4$ may be S.

As an example, when the compound of Formula 2 is reacted with any one of the hydroxy groups (—OH) of the Fc binding peptide, $Y_4$ may be O.

In Reaction Scheme 1 and Reaction Scheme 2, a compound represented by Formula 3 and/or Formula 4 may be produced by reacting amine group (—NH$_2$), thiol group (—SH), and hydroxy group (—OH) residues of the Fc binding peptide with a carbon atom of the first carbonyl group.

In this case, a carbon of the carbonyl group most closely linked to R', that is, an electrophilic carbon atom of the first carbonyl group may have the largest partial positive charge (δ+).

The method for preparing an antibody-payload conjugate may include (2) reacting the linker-Fc binding peptide with the antibody to obtain an antibody comprising the first click chemistry functional group.

In addition, in this case, when the Fc binding peptide has an affinity for a specific site of the Fc domain, the linker-Fc binding peptide conjugate may be induced to react with a specific site of the antibody. The inventors of the present invention developed a technology capable of transferring the first click chemistry functional group to a specific site of the antibody, particularly, the lysine 246 (Fc-Lys246) or lysine 248 (Fc-248) position of Fc, using the Fc binding peptide of SEQ ID NOS: 1 to 5 having an affinity for the FcRn domain of the antibody.

The reaction between the linker-Fc binding peptide conjugate and the antibody may be a nucleophilic substitution reaction. In this case, the nucleophilic substitution reaction may occur when the nucleophilic atom present in the antibody attacks the positively charged or the partially positively charged atom of the linker-Fc binding peptide conjugate. In this case, the nucleophilic atom may be a nitrogen atom of lysine. In addition, the positively charged or partially positively charged atom may be an electrophilic carbon of a carbonyl group included in the linker structure.

In an example, the antibody comprising the first click chemistry functional group may be represented by Formula 5.

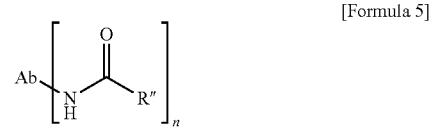

[Formula 5]

In Formula 5,

Ab is an antibody. In a specific embodiment, Ab may be trastuzumab.

R" is any one of click chemistry functional groups, the click chemistry functional group is any one or more of an alkyne, a cycloalkyne such as a cyclooctyne and a cyclononyne (for example, bicyclo[6.1.0]non-4-yn-9-ylmethanol), a trans-cyclooctene, a nitrone, a nitrile oxide, an azide, a conjugated diene, and a dienophile, and in this case, the cycloalkyne, conjugated diene, and diene are the same as those described above.

In addition, the nitrogen atom linked to Ab may be contained in lysine 246 or lysine 248 of the Fc of the antibody. In a specific embodiment, the nitrogen linked to Ab may be included in lysine 246 of the Fc of the antibody. In a specific embodiment, the nitrogen atom linked to Ab may be contained in lysine 248 of the Fc of the antibody.

n is an integer of 1 or more and 4 or less. Exemplarily, n may be 2. In this case, R" may be linked to lysine 246 or lysine 248 which is included in two Fcs in one antibody, respectively, to produce such a structure. In another example, n may be 4. In this case, R" may be linked to lysine 246 and lysine 248, which is included in two Fcs in one antibody, respectively, to produce such a structure.

n is 2, and the nitrogen atom linked to the Ab may be contained in lysine 246 of both Fcs of the antibody. Alternatively, n is 2, and the nitrogen atom linked to the Ab may be contained in lysine 248 of both Fcs of the antibody.

The antibody of Formula 5 may be produced by a reaction represented by the following Reaction Scheme 3.

[Reaction Scheme 3]

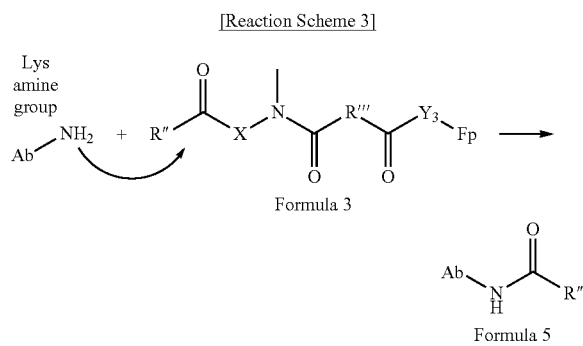

Formula 3

Formula 5

In this case, details about Formulas 3 and 5 are the same as those already described.

In this case, as peptides of SEQ ID NOS: 1 to 5 include 2,3-diaminopropionic acid, 2,4-diaminobutyric acid, ornithine, or lysine at residue 6, respectively, all the corresponding residues have only a difference in length of a carbon skeleton including a free amine group, and have similar structures. Accordingly, all the peptides of SEQ ID NOS: 1 to 5 show a property of binding to the Fc domain of the antibody.

In another example, the antibody comprising the first click chemistry functional group may be represented by Formula 6.

[Formula 6]

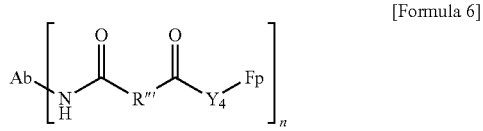

In Formula 6,

Ab is an antibody. In a specific embodiment, Ab may be trastuzumab.

R'" is substituted or unsubstituted $C_{1-20}$ alkylene, substituted or unsubstituted $C_{2-20}$ alkenylene, substituted or unsubstituted $C_{1-10}$ alkynylene, substituted or unsubstituted $C_{1-10}$ polymethylene, substituted or unsubstituted $C_{5-12}$ aryl, substituted or unsubstituted $C_{5-14}$ aryl alkylene, substituted or unsubstituted $C_{8-16}$ aryl alkenylene, substituted or unsubstituted $C_{3-10}$ cycloalkylene, substituted or unsubstituted $C_{3-10}$ heterocycloalkylene, or substituted or unsubstituted $C_{5-12}$ heteroaryl, and the heteroalkylene, heterocycloalkylene or heteroaryl includes at least one or more of N, O, or S, and the substitution is substituted with a non-hydrogen substituent, the non-hydrogen substituent is any one or more selected from a group consisting of —Ra, —O—, =O, —ORa, —SRa, —S—, —N(Ra)$_2$, =NRa, —C(Rb)$_3$, —N=C=O, —NCS, —NO, —NO$_2$, =N—OH, =N$_2$, —N$_3$, —NHC(=O)Ra, —C(=O)Ra, —C(=O)NRaRa —S(=O)$_2$O—, —S(=O)$_2$OH, —S(=O)$_2$Ra, —OS(=O)$_2$ORa, —S(=O)$_2$NRa, —S(=O)Ra, —C(=O)Ra, alkylene-C(=O)Ra, —C(=S)Ra, —C(=O)ORa, alkylene-C(=O)ORa, —C(=O)O—, alkylene-C(=O)O—, —C(=S)ORa, —C(=O)SRa, —C(=S)SRa, —C(=O)NRaRa, alkylene-C(=O)NRaRa, —C(=S)NRaRa, —C(=NRa)NRaRa, and Rb.

In addition, the nitrogen atom linked to Ab may be contained in lysine 246 or lysine 248 of the Fc of the antibody. In a specific embodiment, the nitrogen linked to Ab may be included in lysine 246 of the Fc of the antibody. In a specific embodiment, the nitrogen atom linked to Ab may be contained in lysine 248 of the Fc of the antibody.

Further, in this case, the Fc binding peptide may comprise a first click chemistry functional group. The click chemistry functional group is any one or more of an alkyne, a cycloalkyne such as cyclooctyne and cyclononyne (for example, bicyclo[6.1.0]non-4-yn-9-ylmethanol), a trans-cyclooctene, a nitrone, a nitrile oxide, an azide, a conjugated diene, and a dienophile, and in this case, the cycloalkyne, conjugated diene, and diene are the same as those described above. In addition, the Fc binding peptide may comprise a first click chemistry group at an amino acid residue adjacent to the N-terminal of the sequence thereof. Furthermore, the Fc binding peptide may include a first click chemistry group at the N-terminal of the sequence thereof. Alternatively, the Fc binding peptide may include a first click chemistry functional group at an amino acid residue adjacent to the C-terminal of the sequence thereof. Furthermore, the Fc binding peptide may comprise a first click chemistry functional group at the C-terminal of the sequence thereof.

Fp is a Fc binding peptide. Furthermore, Fp may be any one peptide selected from Formula 13 or 14. Details about Formulas 13 and 14 are the same as those already described.

Fp may be linked via Y$_3$ at amino acid residue 6. In this case, the amino acid residue 6 may be lysine, ornithine, 2,3-diaminopropionic acid, or 2,4-diaminobutyric acid.

n is an integer of 1 or more and 4 or less. Exemplarily, n may be 2. In this case, Fp may be linked to lysine 246 or lysine 248 which is included in two Fcs in one antibody, respectively, to produce such a structure. In another example, n may be 4. In this case, R" may be linked to lysine 246 and lysine 248 which is included in two Fcs in one antibody, respectively, to produce such a structure.

n is 2, and the nitrogen atom linked to the Ab may be contained in lysine 246 of both Fcs of the antibody. In another example, n is 2, and the nitrogen atom linked to the Ab may be contained in lysine 248 of both Fcs of the antibody.

The antibody of Formula 6 may be produced by a reaction represented by the following Reaction Scheme 4.

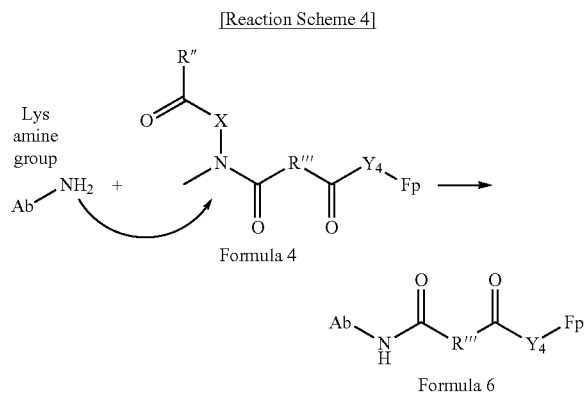

In this case, details about Formulas 4 and 6 are the same as those already described.

In this case, as peptides of SEQ ID NOS: 1 to 5 include 2,3-diaminopropionic acid, 2,4-diaminobutyric acid, ornithine, or lysine at a residue 6, respectively, all the corresponding residues have only a difference in length of a carbon skeleton including a free amine group, and have similar structures. Accordingly, all the peptides of SEQ ID NOS: 1 to 5 show a property of binding to the Fc domain of the antibody.

The method for preparing an antibody-payload conjugate may include (3) preparing the antibody-payload conjugate by reacting the antibody comprising the first click chemistry functional group with a payload comprising a second click chemistry functional group complementary to the first click chemistry functional group.

The payload may include an active moiety. The active moiety may be one or more selected from a nucleic acid, a peptide, and a compound. The active moiety may be any one selected from a group consisting of a drug molecule, an imaging moiety, an optical agent, a vitamin, and a toxin. In a specific embodiment, the active moiety may be a drug molecule. The drug molecule may be a prodrug, a precursor drug, or a drug. The drug molecule may be an anticancer drug, an anti-inflammatory agent, another anti-disease agent, and an antimicrobial agent (antibacterial agent, antifungal agent, antiviral agent). In a specific embodiment, the drug molecule may be mertansine (DM1). In a specific embodiment, the payload may include two or more drug molecules. In a specific embodiment, the active moiety may be an imaging moiety. The imaging moiety may be a contrast agent, a radioisotope, a fluorescent material. In a specific embodiment, the active moiety may be an optical agent, a vitamin, a toxin, or the like, but is not limited thereto.

In addition, the payload includes a second click chemistry functional group. Wherein, the click chemistry functional group is any one or more of an alkyne, a cycloalkyne such as cyclooctyne and cyclononyne (for example, bicyclo[6.1.0]non-4-yn-9-ylmethanol), a trans-cyclooctene, a nitrone, a nitrile oxide, an azide, a conjugated diene, and a dienophile, and in this case, the cycloalkyne, conjugated diene, and diene are the same as those described above.

In an example, the antibody-payload conjugate may be represented by Formula 7.

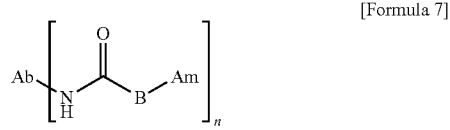

In Formula 7,

Ab is an antibody. In a specific embodiment, Ab may be trastuzumab.

The nitrogen atom linked to Ab may be contained in lysine 246 or lysine 248 of the Fc of the antibody. In a specific embodiment, the nitrogen linked to Ab may be contained in lysine 246 of the Fc of the antibody. In a specific embodiment, the nitrogen atom linked to Ab may be contained in lysine 248 of the Fc of the antibody.

B may be any one of the structures formed by a click-chemistry of a first click chemistry functional group and a second click chemistry functional group. For example, B may be any one of the structures which may be produced by two reactions selected from an alkyne, a cycloalkyne such as cyclooctyne and cyclononyne (for example, bicyclo[6.1.0]non-4-yn-9-ylmethanol), a trans-cyclooctene, a nitrone, a nitrile oxide, an azide, a conjugated diene, and a dienophile. In a specific embodiment, B may be

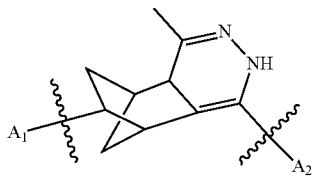

or

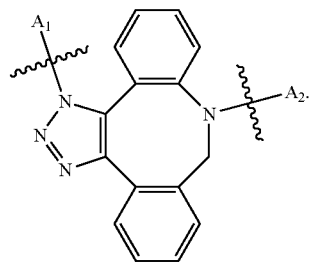

Wherein, $A_1$ may be linked to an antibody, and $A_2$ may be linked to Am. Or, $A_1$ may be linked to Am, and $A_2$ may be linked to an antibody.

Am is an active moiety or a structure comprising the same. In one embodiment, Am may include two or more active moieties. The content on the active moiety is the same as that described in the description of the payload.

n is an integer of 1 or more and 4 or less. Exemplarily, n may be 2. In this case, the payload may be linked to lysine 246 or lysine 248 which is included in two Fcs in one antibody, respectively, to produce such a structure. In another example, n may be 4. In this case, R" may be linked to lysine 246 and lysine 248 which is included in two Fcs in one antibody, respectively, to produce such a structure.

n is 2, and the nitrogen atom linked to the Ab may be contained in lysine 246 of both Fcs of the antibody. In another embodiment, n is 2, and the nitrogen atom linked to the Ab may be contained in lysine 248 of both Fcs of the antibody.

The compound represented by Formula 7 may be produced by Reaction Scheme 5 as an example.

[Reaction Scheme 5]

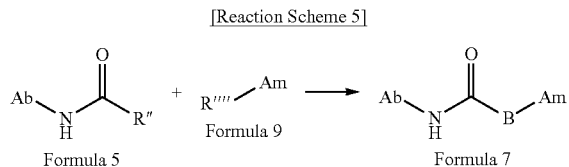

In this case, R″ is the first click chemistry functional group, and is the same as that described when Formula 5 is described in the above.

Further, R″″ is the second click chemistry functional group, and is the same as that described when the payload is described.

In an example, the antibody-payload conjugate may be represented by Formula 8.

[Formula 8]

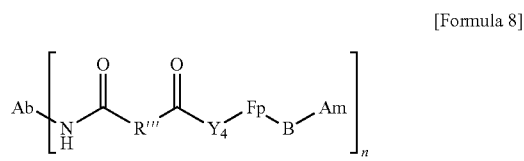

In Formula 8,

Ab is an antibody. In a specific embodiment, Ab may be trastuzumab.

The nitrogen atom linked to Ab may be contained in lysine 246 or lysine 248 of the antibody. In a specific embodiment, the nitrogen atom linked to Ab may be contained in lysine 246 of the antibody. In a specific embodiment, the nitrogen atom linked to Ab may be contained in lysine 248 of the antibody.

B may be any one of the structures formed by a click-chemistry of a first click chemistry functional group and a second click chemistry functional group. For example, B may be any one of the structures which may be produced by two reactive moieties selected from an alkyne, a cycloalkyne such as cyclooctyne and cyclononyne (for example, bicyclo[6.1.0]non-4-yn-9-ylmethanol), a trans-cyclooctene, a nitrone, a nitrile oxide, an azide, a conjugated diene, and a dienophile. In a specific embodiment, B may be

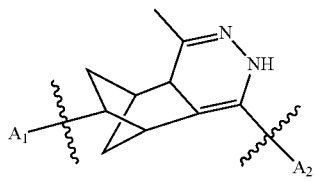

or

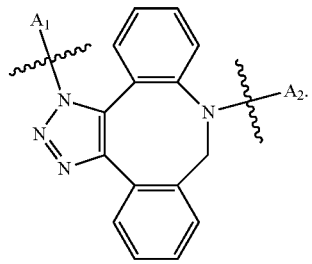

Wherein, $A_1$ may be linked to an antibody, and $A_2$ may be linked to Am. Or, $A_1$ may be linked to Am, and $A_2$ may be linked to an antibody.

Fp is a Fc binding peptide. Furthermore, Fp may be any one peptide selected from Formula 13 or 14. Details about Formulas 13 and 14 are the same as those already described.

The Fp may be linked via $Y_4$ at amino acid residue 6. In this case, the amino acid residue 6 may be lysine, ornithine, 2,3-diaminopropionic acid, or 2,4-diaminobutyric acid.

Am is an active moiety or a structure containing the same. In a specific embodiment, Am may include two or more active moieties. The content on the active moiety is the same as that described in the description of the payload.

B may be bonded to an amino acid residue adjacent to the N-terminal of the Fc binding peptide sequence. In another embodiment, B may be bonded to the N-terminal of the Fc binding peptide. In another embodiment, B may be bonded to an amino acid residue adjacent to the C-terminal of the Fc binding peptide sequence. In another embodiment, B may be bonded to the C-terminal of the Fc binding peptide.

n is an integer of 1 or more and 4 or less. Exemplarily, n may be 2. In this case, the payload may be linked to lysine 246 or lysine 248 which is included in two Fcs in one antibody, respectively, to produce such a structure. In another example, n may be 4. In this case, payload may be linked to lysine 246 and lysine 248 which is included in two Fcs in one antibody, respectively, to produce such a structure.

n is 2, and the nitrogen atom linked to the Ab may be contained in lysine 246 of both Fcs of the antibody. Alternatively, n is 2, and the nitrogen atom linked to the Ab may be contained in lysine 248 of both Fcs of the antibody.

A compound represented by Formula 8 may be produced by Reaction Scheme 6 as an example.

[Reaction Scheme 6]

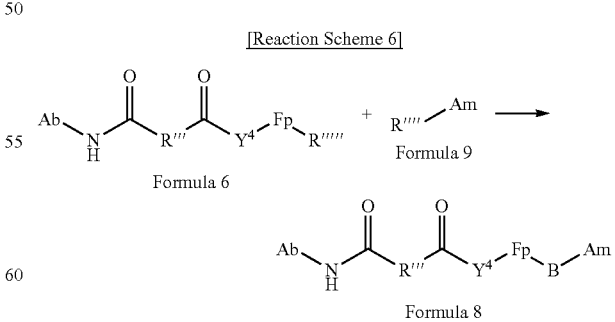

In this case, R″″ is a first click chemistry functional group, and is the same as that described when Formula 6 is described in the above. A first click chemistry functional group may be involved in an amino acid residue in the process of synthesizing a Fc binding peptide. Any one residue may be used as the amino acid residue in which the first click chemistry functional group is involved, but it is preferred that the amino acid residue is not residue 6. This is because the residue 6 is a residue designed for the substitution reaction with the linker. Through the process of artificial synthesis of the peptide, the Fc binding peptide may include the first click chemistry functional group at an amino acid residue adjacent to the N-terminal of the sequence thereof. In a specific embodiment, the Fc binding peptide may include the first click chemistry group at the N-terminal of the sequence thereof. In a specific embodiment, the Fc binding peptide may include the first click chemistry functional group at an amino acid residue adjacent to the C-terminal of the sequence thereof. In a specific embodiment, the Fc binding peptide may include the first click chemistry functional group at the C-terminal of the sequence thereof.

Further, R"" is a second click chemistry functional group, and is the same as that described when the payload is described.

The present application may provide a linker that assists in transport and binding reactions such that a payload can be linked to a desired target molecule.

The linker or linker moiety may be directly linked to a target molecule. The linker moiety directly linked to the target molecule may be linked to a payload.

The linker moiety may be a part of residue or a part of functional group of the linker.

For example, the linker moiety may be R" or a part of residue including R".

For example, the linker moiety may be a part of residue of the linker excluding R".

The target molecule, to which the linker moiety is linked, may be linked to a payload by a click reaction, that is, a reaction between click chemistry functional groups, but is not limited thereto.

In an exemplary embodiment, when the linker has a structure of Formula 1, the linker moiety linked to the target molecule may include a click chemistry functional group.

In this case, the linker moiety linked to the target molecule may participate in a click reaction along with the payload.

Such a linker may not affect the biological activity of the target molecule. That is, the linker may have little effect on the half-life, excretion, blood stability, and the like of the target molecule.

The half-life of the target molecule may be determined by the FcRn binding affinity of the target molecule. For example, the target molecule may be recycled in vivo by binding to FcRn, and the half-life may be increased in vivo.

The excretion of the target molecule may be determined by the extent to which the target molecule is excreted by the kidneys as a result of the aggregation of protein bodies.

As an example, the linker may increase the half-life of a drug in blood by linking a protein and a compound which have a short intracellular half-life. For example, a drug may be linked to a target molecule which have long intracellular half-like.

In another exemplary embodiment, when the linker has a structure of Formula 2,
the linker moiety linked to the target molecule may not include a click chemistry functional group.

The linker moiety linked to the target molecule may be linked to a peptide, a polypeptide, a protein and/or a compound comprising a click chemistry functional group.

The peptide, polypeptide, protein and/or compound may be linked to the payload by a click reaction.

Such a linker may affect the biological activity of the target molecule. When the linker affects the biological activity of the target molecule, the linker affects the half-life, excretion, or blood stability of the target molecule. For example, when the linker is indirectly linked to the target molecule, the linker may rapidly release the payload in vivo by reducing the half-life of the target molecule.

The linker may be linked to a peptide or polypeptide having a binding affinity for a specific target molecule. Such a linker may site-specifically link the payload to the target molecule.

As an example, the target molecule may be an antibody.

For example, the antibody may be an IgG antibody or a partial fragment of the IgG antibody. The IgG antibody may be a human IgG (IgG1, IgG2, IgG3, or IgG4) and/or a rabbit IgG. The IgG antibody may be a human-derived $CH_2$—$CH_3$ domain. The target molecule may be an antibody, or a partial fragment of the antibody, but is not limited thereto.

As an example, the Fc binding peptide may have a binding affinity with the antibody.

For example, the Fc binding peptide may have a binding affinity with an IgG antibody. The Fc binding peptide may have a specific binding affinity with a specific domain of an IgG antibody.

For example, the Fc binding peptide may have specificity for a heavy-chain or light-chain variable region of an IgG antibody.

For example, the Fc binding peptide may have specificity with a constant domain of the heavy chain of an IgG antibody. In this case, the heavy chain constant domain may be a $CH_2$ domain and/or a $CH_3$ domain.

The Fc binding peptide may be a peptide or polypeptide to which a compound is linked.

For example, the Fc binding peptide may include a click chemistry functional group.

The present invention provides a method for treating cancer, the method comprising administering an antibody-payload conjugate. In this case, the cancer may be selected from bladder cancer, bone cancer, brain cancer, breast cancer, heart cancer, cervical cancer, colorectal cancer, rectal cancer, esophageal cancer, fibrosarcoma, gastric cancer, gastrointestinal cancer, head and neck cancer, Kaposi's sarcoma, renal cancer, leukemia, liver cancer, lung cancer, lymphoma, melanoma, myeloma, ovarian cancer, pancreatic cancer, penile cancer, prostate cancer, testicular germ cell cancer, thymoma, and thymus cancer. Furthermore, the cancer may be breast cancer.

The present invention provides a pharmaceutical composition for treating cancer, the composition including an antibody-payload conjugate. In this case, the cancer may be selected from bladder cancer, bone cancer, brain cancer, breast cancer, heart cancer, cervical cancer, colorectal cancer, rectal cancer, esophageal cancer, fibrosarcoma, gastric cancer, gastrointestinal cancer, head and neck cancer, Kaposi's sarcoma, renal cancer, leukemia, liver cancer, lung cancer, lymphoma, melanoma, myeloma, ovarian cancer, pancreatic cancer, penile cancer, prostate cancer, testicular germ cell cancer, thymoma, and thymus cancer. Furthermore, the cancer may be breast cancer.

Hereinafter, the present invention will be described in more detail through Examples.

These Examples are provided only for more specifically describing the present invention, and it will be obvious to a person with ordinary skill in the art to which the present invention pertains that the scope of the present invention is not limited by these Examples. The numbers given to the names of the compounds in the following Examples are written with reference to the drawings.

[Example 1] Synthesis method of compound I (Trans Linker: NHS & Norbornene, Formula 1-1-2) and confirmation of structure thereof Example 1-1. Synthesis and confirmation of the structure of compound 1

10 g (68.4 mmol, 1.0 eq) of monomethylglutarate was dissolved in 250 mL of dichloromethane (DCM) and the resulting solution was stirred. 17.7 g (92.3 mmol, 1.34 eq) of 1-ethyl-3-(3-dimethylaminopropyl)carbodiimide (EDCi) and 24 mL (138 mmol, 2.0 eq) of N,N-diisopropylethylamine (DIPEA) were slowly added dropwise thereto, the resulting solution was stirred for 20 minutes, and then 8 mL (68.7 mmol, 1.0 eq) of O-benzylhydroxyamine was slowly added dropwise thereto. After 18 hours, the reaction solution was removed by concentration under reduced pressure, and the residue was re-dissolved in ethyl acetate (EA). The organic layer was washed three times using a 10% citric acid solution and dried using a saturated salt solution and sodium sulfate. A target compound was used in the next reaction without purification (crude yield: 12.9 g, 88%). TLC (EA: Hex=2:1); Rf=0.5

1 H NMR (300 MHz, DMSO) δ 7.35 (d, J=3.5 Hz, 5H), 4.75 (d, J=3.5 Hz, 2H), 3.56 (d, J=4.0 Hz, 3H), 2.26 (td, J=7.3, 3.8 Hz, 2H), 1.96 (t, J=5.6 Hz, 2H), 1.78-1.61 (m, 2H).

Example 1-2 Synthesis and Confirmation of structure of Compound 2

After 12.9 g of Compound 1 was dissolved in 200 mL of N,N-dimethylformamide (DMF), the resulting solution was stirred at 0° C. 24 mL (160 mmol, 3.08 eq) of 1,8-diazabicyclo(5.4.0)undec-7-ene (DBU) and 10 mL (160 mmol, 3.08 eq) of methyl iodide (MeI) were slowly added dropwise thereto. 0.2 mL of diethylamine was slowly added dropwise thereto. After the resulting solution was stirred for 20 hours, the reaction solvent was mixed with Celite and removed by concentration under reduced pressure, and a target compound was purified by column chromatography (EA:Hex=1:1) to obtain 7.6 g (yield: 56%). TLC (EA:Hex=1:1); Rf=0.5

1 H NMR (300 MHz, cdcl3) δ 7.44-7.33 (m, 5H), 4.82 (s, 2H), 3.65 (s, 3H), 3.20 (s, 3H), 2.43 (d, J=7.2 Hz, 2H), 2.34 (t, J=7.3 Hz, 2H), 1.98-1.85 (m, 2H).

Example 1-3 Synthesis and confirmation of structure of Compound 3

After 4.18 g (15.8 mmol, 1.0 eq) of Compound 2 was dissolved in 100 mL of tetrahydrofuran (THF), the resulting solution was stirred. 5 mL of 2 N lithium hydroxide (LiOH) was slowly added dropwise thereto at 0° C., and then the resulting solution was stirred for 3 hours. The reaction was terminated by adding 60 mL of H₂O thereto, and washing was performed twice on the aqueous layer using 150 ml of EA. Then, the aqueous layer was titrated to pH 3.0 using 2N HCl solution, and the target compound was extracted three times using 50 ml of EA. The organic layer was dried using a saturated salt solution and sodium sulfate to obtain 2.46 g (yield: 62%). TLC (EA:Hex=1:1); Rf=0.1

1H NMR (300 MHz, DMSO) δ 12.06 (s, 1H), 7.51-7.29 (m, 5H), 4.86 (s, 2H), 3.13 (s, 3H), 2.38 (t, J=7.3 Hz, 2H), 2.22 (dt, J=11.7, 7.4 Hz, 4H).

Example 1-4 Synthesis and confirmation of structure of Compound 4

After 2.46 g of Compound 3 was dissolved in 40 mL of methanol (MeOH), a hydrogenation reaction was performed in the presence of palladium on carbon (Pd/C) over 18 hours, and after the reaction was terminated, the Pd/C was removed through a short-path column, and then a target compound was purified and concentrated to obtain 1.2 g (yield: 76%).

1H NMR (300 MHz, DMSO) δ 12.06 (s, 1H), 7.51-7.29 (m, 5H), 4.86 (s, 2H), 3.13 (s, 3H), 2.38 (t, J=7.3 Hz, 2H), 2.22 (dt, J=11.7, 7.4 Hz, 4H).

Example 1-5 Synthesis and confirmation of structure of Compound 5

0.17 g (1.06 mmol, 1.0 eq) of Compound 4 was dissolved in 10 mL of DCM and the resulting solution was stirred. 0.22 g (1.73 mmol, 1.63 eq) of exo-5-norbornene acid chloride and 0.2 mL (1.1 mmol, 1.0 eq) of DIPEA were slowly added dropwise thereto at 0° C. After the resulting solution was stirred for 2 hours, the organic layer was washed three times using a 10% citric acid solution, and dried using a saturated salt solution and sodium sulfate. A target compound was used in the next reaction without purification (crude yield: 0.24 g, 68%). TLC (DCM:MeOH=10:1); Rf=0.3

Expected M.W. (M+H)+: 282.13 g/mol
Measured M.W. (M+H)+: 282.1 g/mol

Example 1-6 Synthesis and confirmation of structure of Compound I 0.24 g (0.72 mmol, 1.0 eq) of Compound 5 was dissolved in 3 mL of DCM and the resulting solution was stirred. 0.26 g (0.87 mmol, 1.2 eq) of N,N,N',N' tetramethyl-O—(N-succinimidyl)uroniumtetrafluorborate (TSTU) and 0.15 mL (0.87 mmol, 1.2 eq) of DIPEA were slowly added dropwise thereto. After the resulting solution was stirred for 1 hour, the organic layer was washed three times using a 10% citric acid solution, and dried using a saturated salt solution and sodium sulfate. A target compound was purified through column chromatography (EA:Hex=1:1) to obtain 0.04 g (yield: 15%). TLC (EA:Hex=1:1); Rf=0.3 (see FIG. 1)

1H NMR (300 MHz, DMSO) δ 6.18 (ddd, J=16.9, 5.5, 3.0 Hz, 2H), 2.94 (s, 1H), 2.80 (s, 4H), 2.71 (s, 1H), 2.67 (q, J=1.0 Hz, 3H), 2.25 (dd, J=25.9, 18.6 Hz, 4H), 1.86 (ddd, J=18.9, 11.5, 5.8 Hz, 4H), 1.45-1.26 (m, 4H).

[Example 2] Synthesis method and confirmation structure of Compound II (Cis Linker: NHS & Norbornene, Formula 2-1-2)

Example 2-1 Synthesis and confirmation structure of Compound 6

0.1 g (0.88 mmol, 1.0 eq) of N-methylhydroxyamine hydrochloride was dissolved in 2 mL of tetrahydrofurane (THF) at −25° C., and the resulting solution was stirred. 0.07 g (0.88 mmol, 1.0 eq) of glutaric anhydride was added thereto, the resulting solution was stirred for 10 minutes, and then 0.25 mL (1.76 mmol, 2.0 eq) of triethylamine was slowly added dropwise thereto. After 1 hour, 0.14 g (0.88 mmol, 1.0 eq) of (1S,2R,4S)-bicyclo[2.2.1]hept-5-ene-2-carbonyl chloride and 0.12 mL (0.88 mmol, 1.0 eq) of triethylamine were slowly added dropwise thereto, and then the reaction was performed at room temperature for 1 hour. After the reaction solution was removed by concentration under reduced pressure, the residue was re-dissolved in ethyl acetate (EA), the resulting solution was washed three times using a 10% citric acid solution, and dried using a saturated salt solution and sodium sulfate. A target compound was used in the next reaction without purification. TLC (DCM: MeOH=3:1, acetic acid 1 drop); Rf=0.4

Calculated mass (M+H)+: 282.13 g/mol
Measured mass (M+H)+: 282.1 g/mol

Example 2-2 Synthesis of Compound II

Compound 6 was dissolved in 2 mL of dichloromethane (DCM), and 0.22 g (0.73 mmol, 0.8 eq) of TSTU and 0.15 mL (0.88 mmol, 1.0 eq) of N,N-diisopropylethylamine (DIPEA) were slowly added dropwise thereto. After reaction for 1 hour, the reaction solution was washed three times using a 10% citric acid solution, and dried using a saturated sodium hydrogen carbonate solution, a saturated salt solution, and sodium sulfate. A target compound was purified through column chromatography (EA:Hex=1:1) TLC (EA:Hex=2:1); Rf=0.4 (see FIG. 3)

Example 2-3 Confirmation of structure of Compound II

Figure 6:
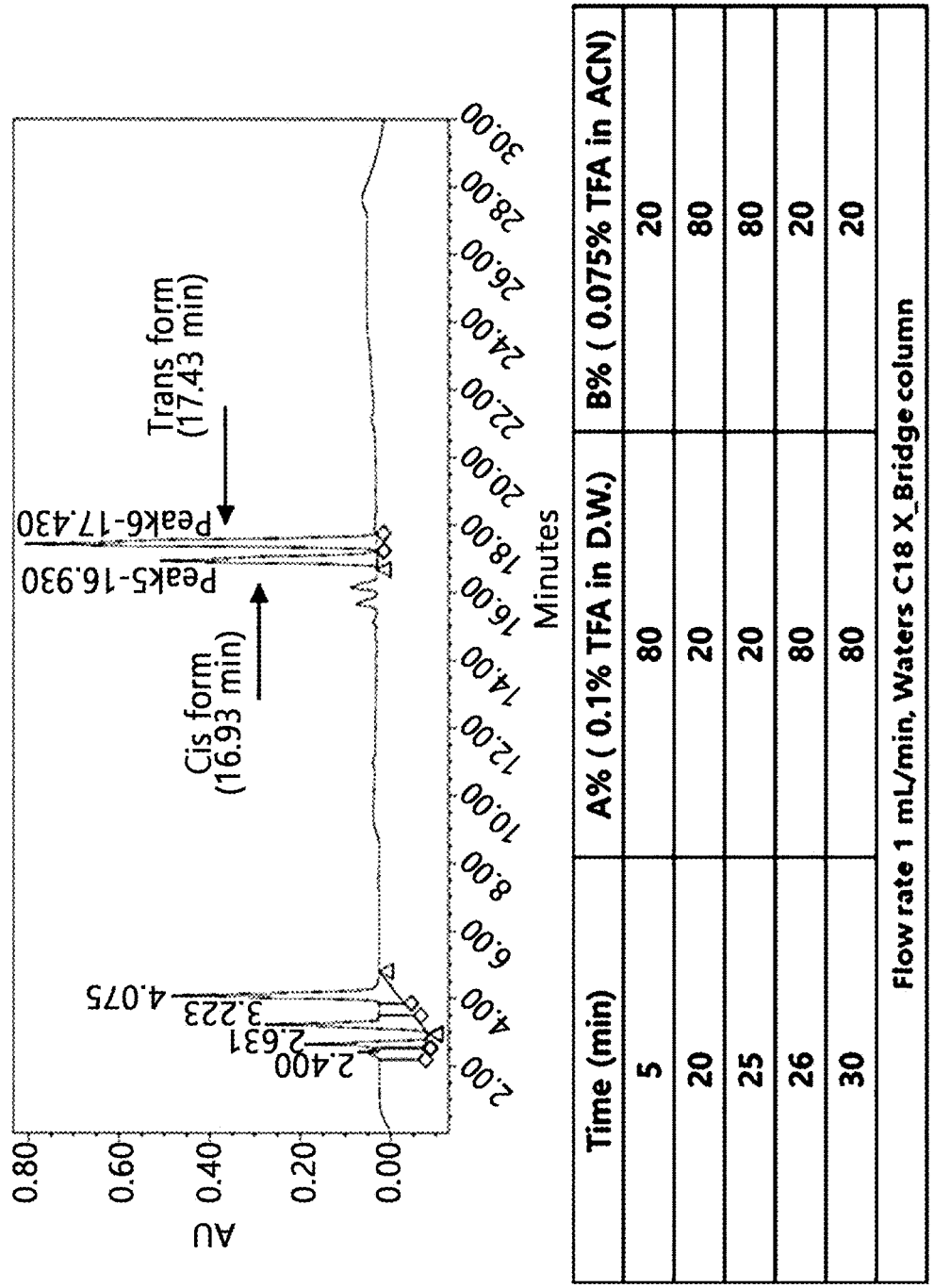
FIG. 6 illustrates the results of confirming the isomer structure of Compound II through HPLC.
Figure 7:
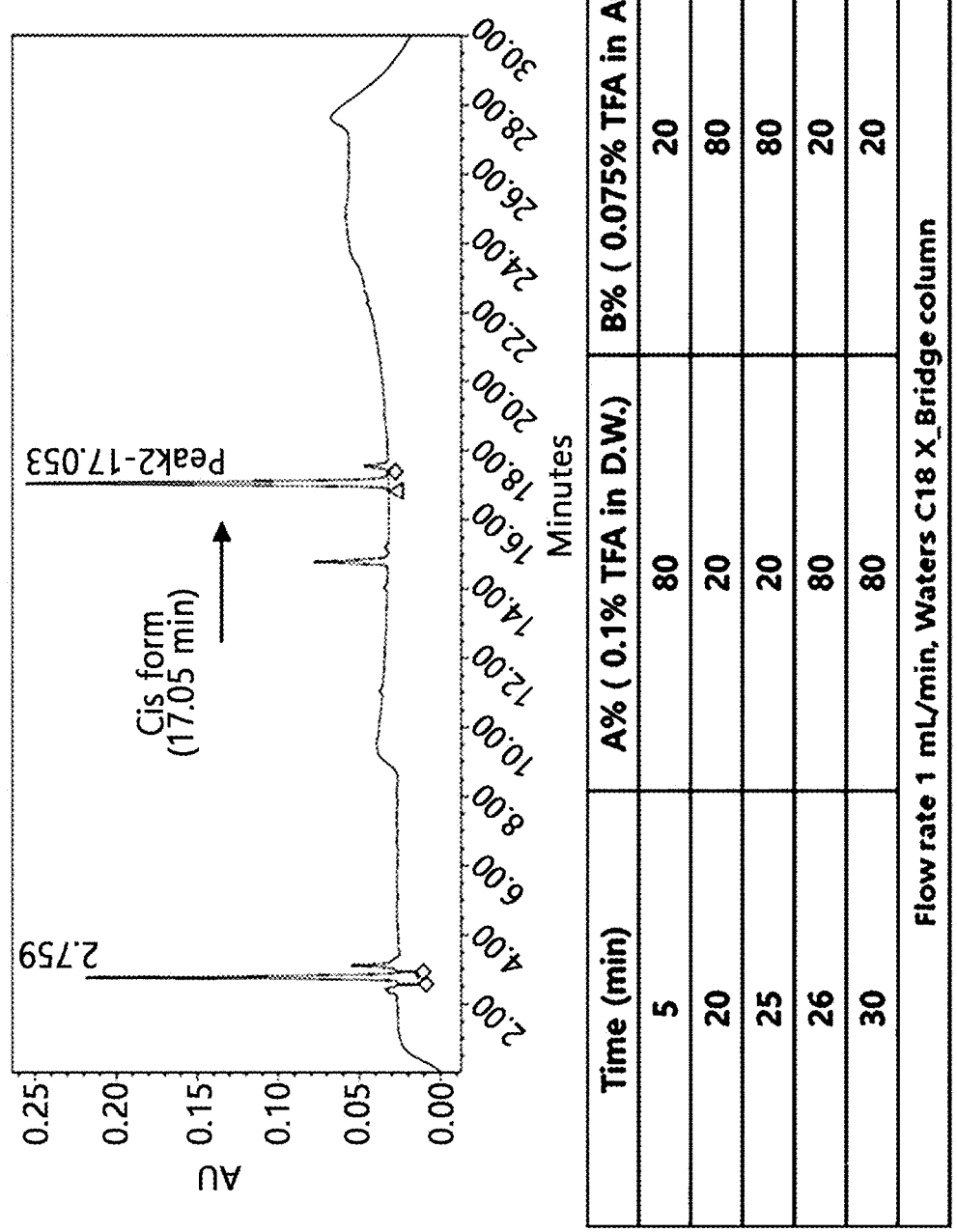
FIG. 7 illustrates the results of obtaining Compound II through HPLC.

A final Compound II was synthesized by the method specified in Examples 2-1 and 2-2, and the presence of an isomer was confirmed through HPLC analysis as illustrated in FIG. 6. HPLC purification was performed based on the analysis conditions illustrated in FIG. 6, and compound II(cis) having a purity as shown in FIG. 7 was obtained through HPLC analysis. The analysis of the final Compound II was completed by confirming the structural analysis of the purified Compound II by mass spectrometry.

Calculated mass (M+H)+: 379.14 g/mol
Measured mass (M+H)+: 379.0 g/mol

[Example 3] Confirmation of structure of isomer Compound 6 (Cis Linker or Trans Linker: NHS & Norbornene)

The cis and trans structures of Compound 6, which is an isomer, were confirmed using a high speed liquid chromatograph (HPLC) apparatus. For HPLC analysis, Waters 2695 HPLC model from Waters was used, and as an analysis column, Xbridge C18 (4.6×250 mm, 5 μm; Waters) was used, and in the case of a mobile phase solvent, water including 0.1% trifluoroacetic acid as an A solvent and acetonitrile including 0.075% trifluoroacetic acid as a B solvent were used. According to the above description, the characteristics of each structure were analyzed by the absorbance at a wavelength of 220 nm.

Figure 3:
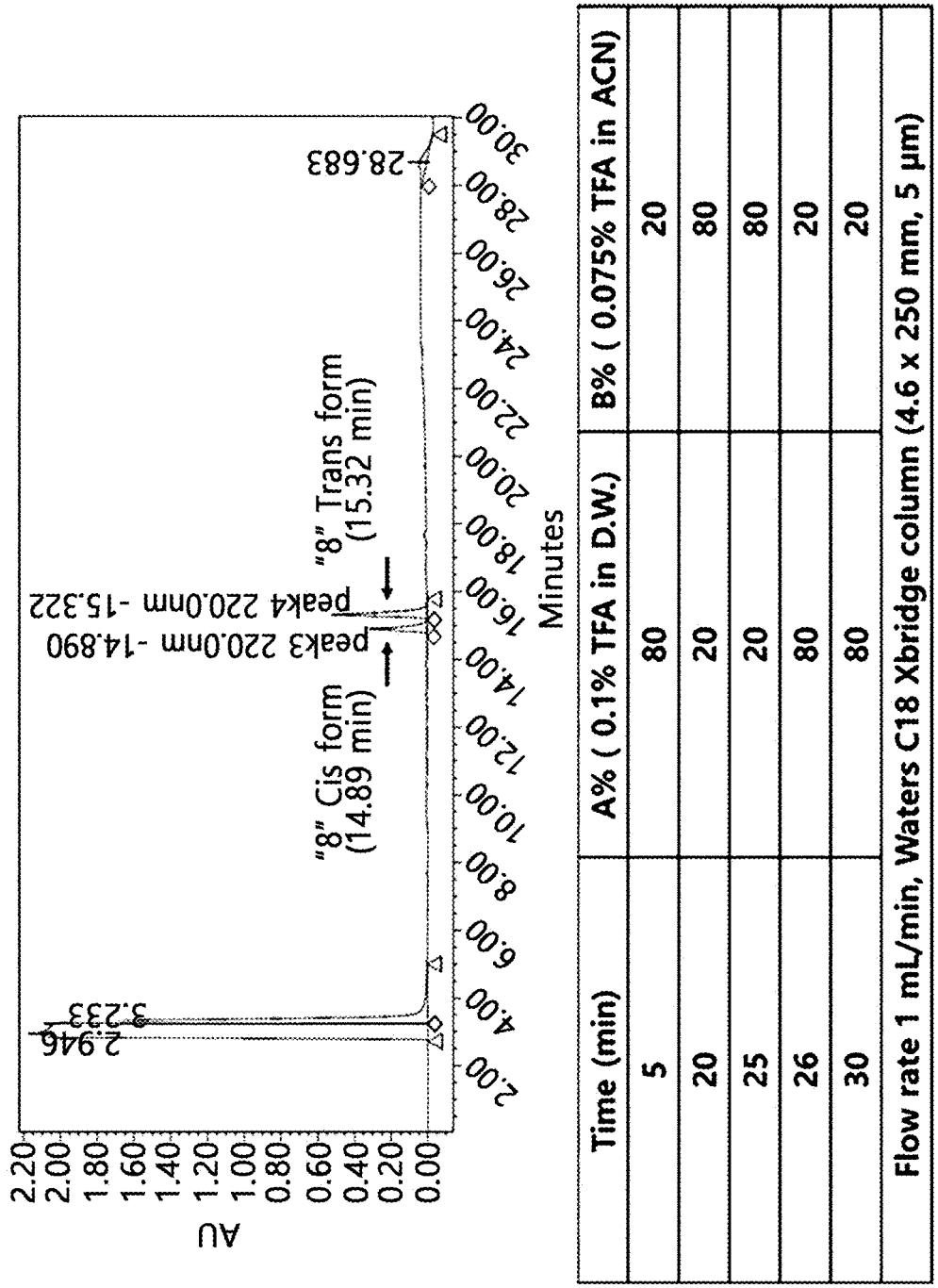
FIG. 3 illustrates the results of HPLC spectrum analysis of the isomer structure of Compound 6.
Figure 4:
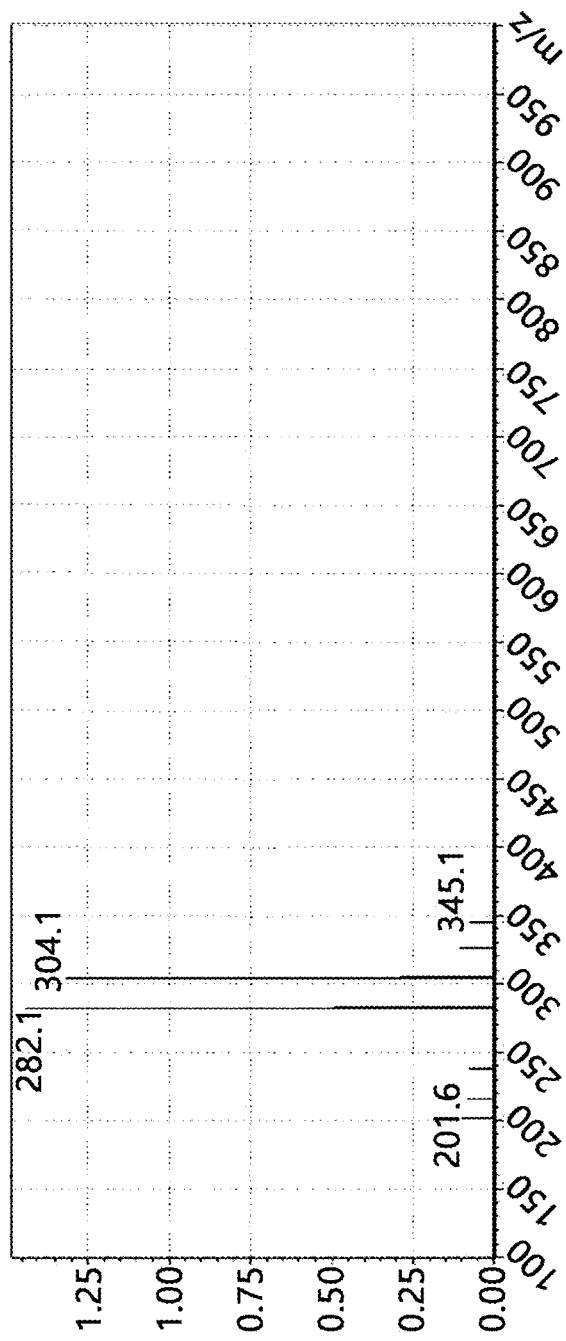
FIG. 4 illustrates the results of molecular weight analysis of Compound 6 (cis).
Figure 5:
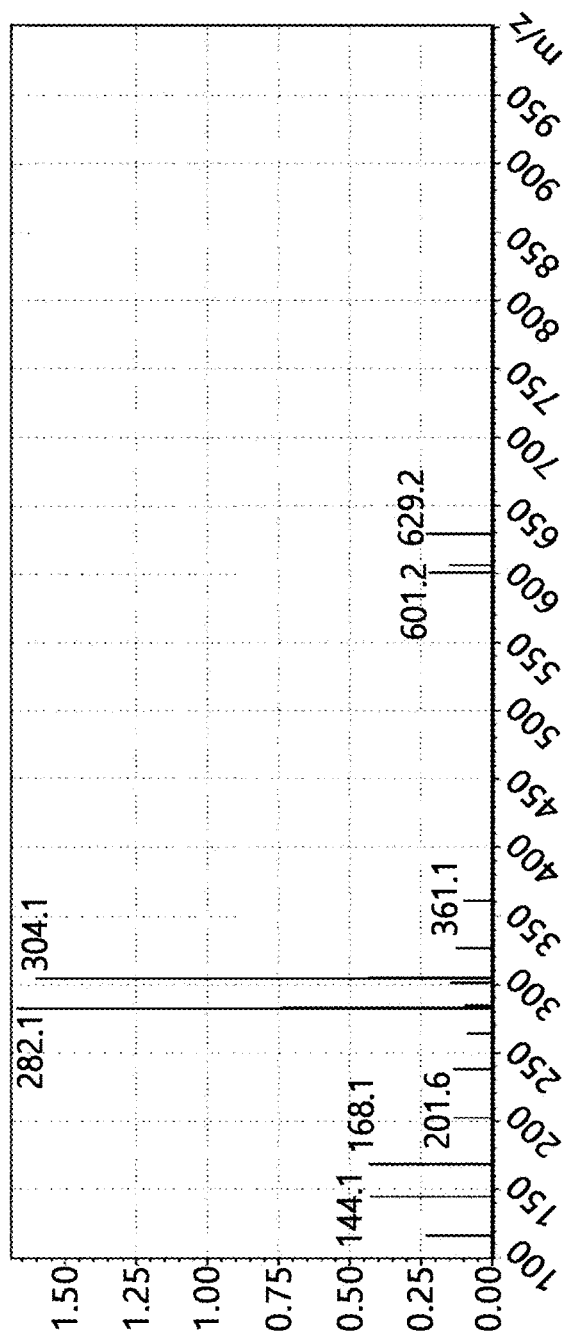
FIG. 5 illustrates the results of molecular weight analysis of Compound 6 (trans).

As illustrated in FIG. 3, it was confirmed that the peaks were observed at 14.89 minutes for the cis-form structure of Compound 6 and at 15.32 minutes for the trans-form structure of Compound 6. The analysis for each structure was confirmed by mass spectrometry (Shimadzu, LCMS-8050), and FIGS. 4 and 5 illustrate the results of mass spectrometry for the cis and trans structures of Compound 6. As a result of confirming the molecular weight, it was confirmed that as the material corresponding to each peak, a molecular weight of 282, to which one hydrogen molecule was bound, was observed.

Calculated mass (M+H)+: 282.13 g/mol
Measured mass (M+H)+: 282.1 g/mol

[Example 4] Synthesis and confirmation of structure of Fc binding peptide

Example 4-1. Synthesis and confirmation of structure of FcBP(6Lys)-Norbornene

[Formula 10]

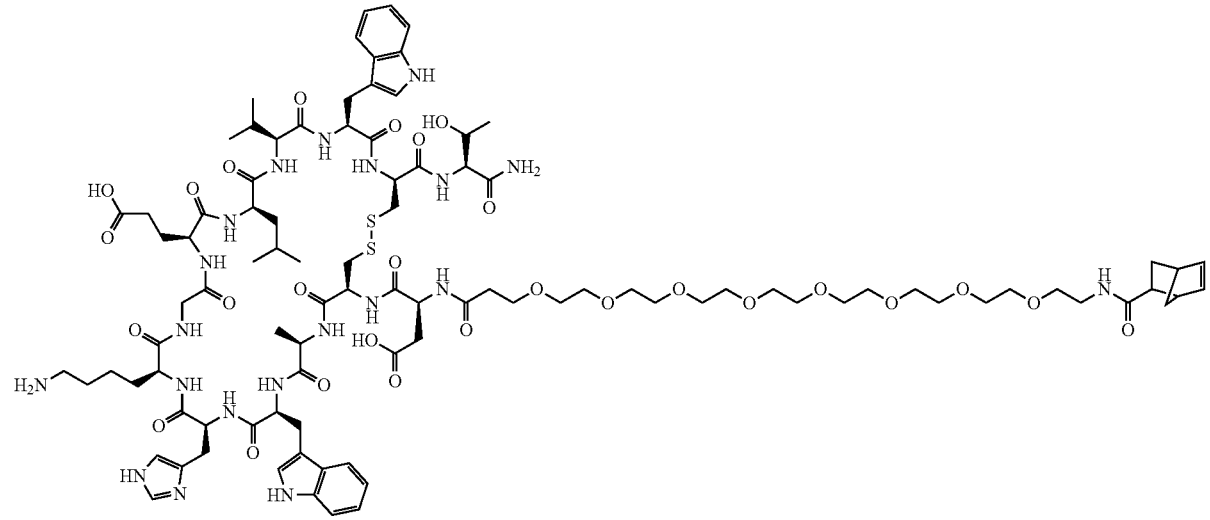

FcBP(6Lys)-Norbornene
Exact Mass: 2086.97
Molecular Weight: 2088.40

Example 4-1-1: Synthesis of FcBP(6Lys)-Norbornene

List of Fmoc amino acids used and order of introduction of Fmoc amino acids used Fmoc-L-Thr(tBu)-OH, Fmoc-Cys(Trt)-OH, Fmoc-L-Trp(Boc)-OH, Fmoc-L-Val-OH, Fmoc-L-Leu-OH, Fmoc-L-Glu(OtBu)-OH, Fmoc-Gly-OH, Fmoc-Lys(Boc)-OH, Fmoc-L-His(Trt)-OH, Fmoc-L-Trp(Boc)-OH, Fmoc-Ala-OH, Fmoc-Cys(Trt)-OH, Fmoc-Asp(tBu)-OH.

Production Method (a) Introduction of Amino Acids

The amount of reagent used in the following process was based on 0.25 mmole. 0.5 g of a clear amide resin (0.48 mmole/g, Peptides International, USA) was put into a synthesis reactor, and 1 mmole of each Fmoc-amino acid block weighed and prepared in the order of the peptide amino acid sequence from the C-terminal to the N-terminal.

A reaction of attaching the activated residue to the clear amide resin by activating the Fmoc-amino acid was performed sequentially from the C-terminal amino acid.

The removal of Fmoc was performed in 20% piperidine-containing DMF, and for the activation and introduction of the residue, amino acids prepared according to the sequence were mixed with 2 mL of a 0.5 M HOBt-containing DMF solution, 2 mL of a 0.5 M HBTU-containing DMF solution, and 174 µL of DIPEA for 5 minutes, and then the resulting mixture was poured into a reactor containing a resin and was mixed for 2 hours.

The confirmation of the introduction reaction was performed by the Kaiser test method, and when it was confirmed that there was no reaction, the introduction reaction was repeated once more, or capping was performed with a 20% $Ac_2O$-containing DMF solution. The resin was sufficiently washed with DMF and DCM before moving on to the next step in each introduction reaction and Fmoc removal process. Such a process was performed repeatedly until a target peptide sequence was completed.

(b) Introduction of H-PEG8—OH

To introduce H-$PEG_8$-OH at the N-terminal after all amino acid introductions had been completed, 1 mL of 0.5 M Fmoc-N-amido-dPEG8-acid in a DMF solution, 1 mL of a 0.5 M HBTU-containing DMF solution, 1 mL of a 0.5 M HOBt-containing DMF solution, and 87 µL of DIPEA were mixed for 5 minutes, and then the resulting mixture was poured into a reactor containing a resin and was mixed for 2 hours.

The progress of the reaction was confirmed by the Kaiser test method, and when it was determined that unreacted amines remained, the reaction time was further extended by 1 to 3 hours, or the reaction solution was emptied and the aforementioned reaction process was repeated again. An N-terminal Fmoc protecting group was removed using 20% piperidine-containing DMF, and then the resin to which the peptide was attached was dried and weighed.

(c) Introduction of Norbornene

For the removal of the N-terminal Fmoc protecting group, 4 eq. of norbornene carboxylic acid, 2 mL of a 0.5 M HOBt-containing DMF solution, 2 mL of a 0.5 M HBTU-containing DMF solution, and 174 µL of DIPEA were mixed with a resin for 5 minutes, and then the resulting mixture was poured into a reactor containing a resin and was mixed for 2 hours. The confirmation of the introduction reaction was performed by the Kaiser test method, and when it was confirmed that there was no reaction, the introduction reaction was repeated once more.

(d) The peptide was cleaved from the resin by stirring 250 mg of the peptide-attached resin prepared in step (c) with 2 ml of a mixture of TFA, TIS, water, and EDT(94:1.0:2.5:2.5) at room temperature for 120 minutes. The cleavage mixture was filtered, the filtrate was concentrated by about half with nitrogen gas, and then ether was poured to precipitate the peptide. The precipitated peptide was further washed three times with ether and dried with nitrogen gas. The dried precipitate was dissolved in 0.1% TFA-30% ACN-containing water, the resulting solution was stirred for 6 hours, and then concentrated.

After the concentrate was dissolved in a 0.01 M ammonium acetate buffer (pH 6.5) solution containing 5%-DMSO-20%-ACN at a concentration of 0.1 mg/mL, and the resulting solution was stirred in an air-exposed state for 3 days. The progress of a disulfide bond formation reaction was observed by HPLC, and when it was determined that the reaction did not proceed any further, the reaction solution was freeze-dried to obtain a peptide precipitate.

(e) Purification

Figure 8:
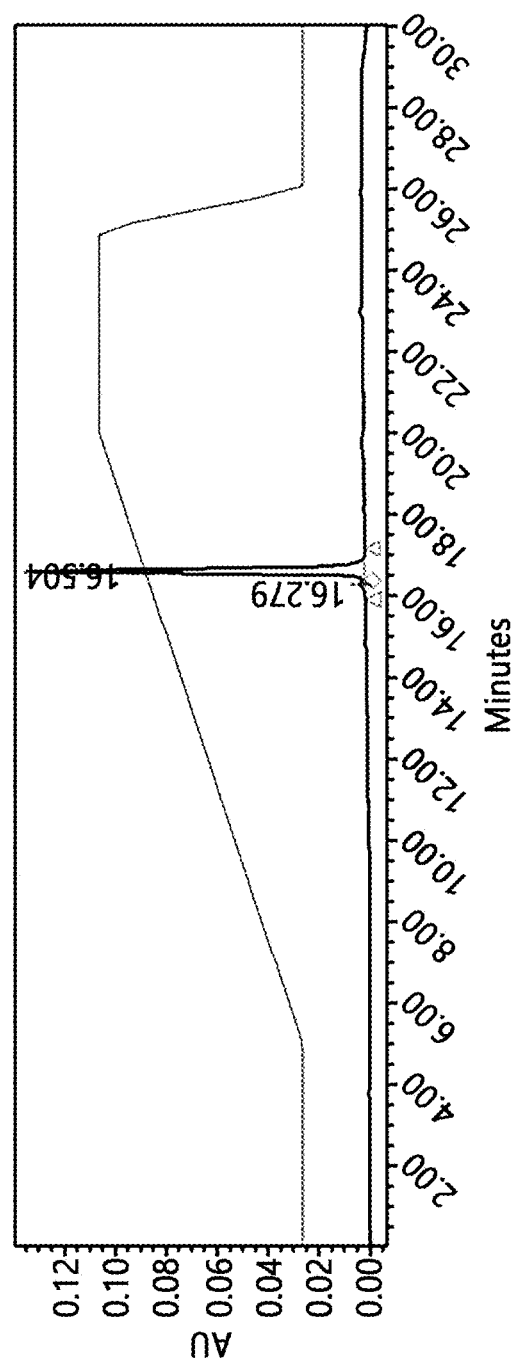
FIG. 8 illustrates the HPLC results of FcBP(6Lys)-Norbornene.

The peptide precipitate obtained by lyophilization in step (d) was purified under the prep-LC conditions shown in the following Table 5 and lyophilized. It was confirmed by analytical HPLC that each of the obtained peptides had a purity of 90% or more, and the results are illustrated in FIG. 8.

norbornene-PEG8-Asp-Cys\*-Ala-Trp-His-Lys-Gly-Glu-Leu-Val-Trp-Cys\*-Thr-$NH_2$ (Cys\*: disulfide binding site)

TABLE 5

| Prep-LC purification conditions | |
|---|---|
| Device name | Waters 2525 pump, Waters 2487 UV detector |
| Column | Waters, XBridge Prep C18 5 µm OBD 19 × 250 mm |
| Mobile phase A/B | 0.1% TFA in $H_2O$/0.1% TFA in Acetonitrile |
| Gradient | 0 min → 30 min: B 20% → B 100% |
| Flow rate | 10 mL/min    Detected wavelength    UV 280 nm |

Example 4-1-2: Confirmation of structure of FcBP(6Lys)-norbornene (oxidized form)

The synthesis of FcBP (6Lys) was confirmed by LC mass-based molecular weight measurement.

Measurement apparatus: Waters Quattro Premier XE

Calculated molecular weight: 2088.40 g/mol

Measured molecular weight $(M/2+H)^{2+}$: 1044.84 g/mol

Figure 9:
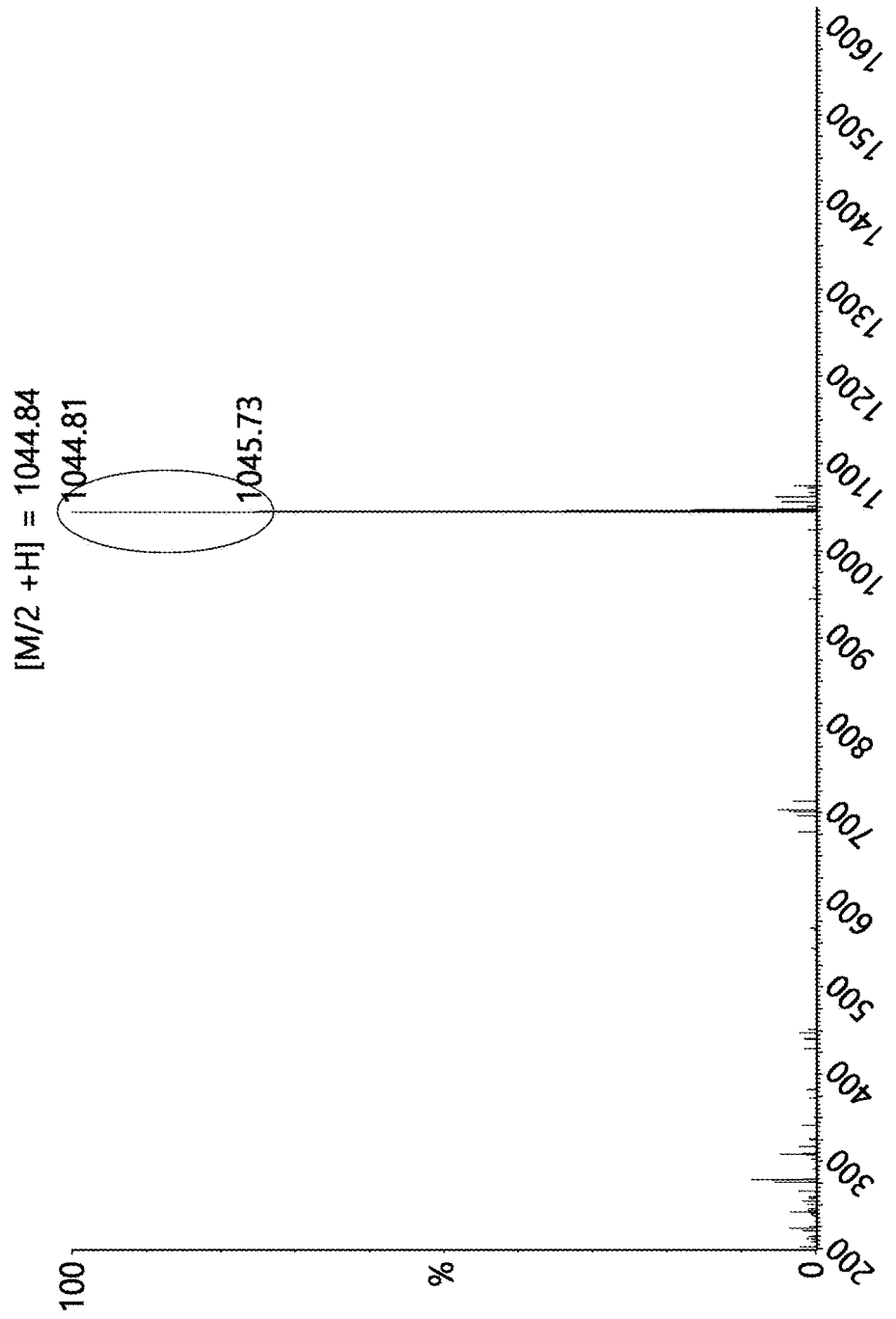
FIG. 9 illustrates the LC mass results of FcBP(6Lys)-Norbornene.

The results are illustrated in FIG. 9.

Example 4-2. Synthesis and confirmation of structure of Compound I -FcBP (6Lys)-norbornene

[Formula 11]

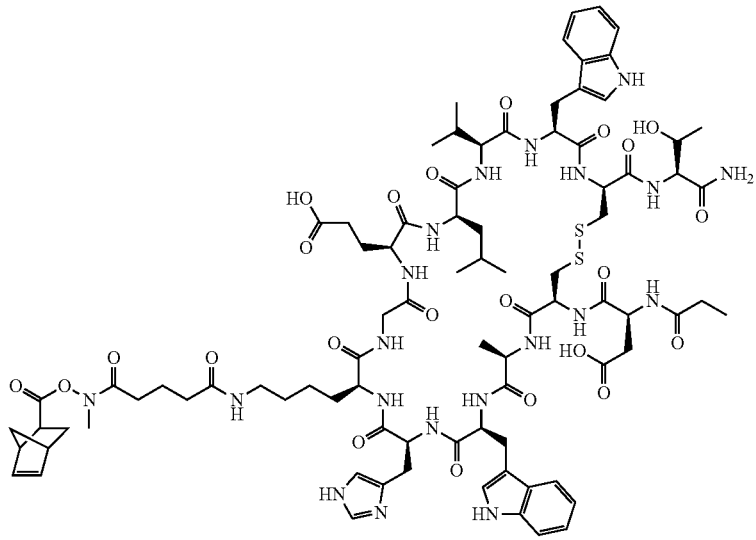

Compound I

FcBP(6Lys)-Norbornene
Exact Mass: 2350.09
Molecular Weight: 2351.69

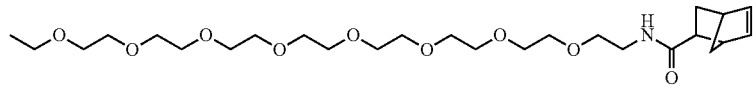

Example 4-2-1: Synthesis of Compound I -FcBP (6Lys)-norbornene

Compound I (trans-norbornene Weinreb amide)-FcBP was synthesized in DMF, and in order to introduce Compound I into FcBP (6Lys)-norbornene, 3 eq of DIPEA and 3 μmol of Compound I were dissolved in 2.5 μmol of FcBP (6Lys)-norbornene dissolved in DMF, and the resulting solution was stirred.

To confirm the introduction reaction, analysis was performed by HPLC, and when the reaction was not terminated, the termination of the reaction was observed by adding DIPEA therein in 1 eq increments.

After the termination of the reaction was confirmed, the reaction solution was concentrated, and I-FcBP (6 Lys)-norbornene was purified through the Preparative-HPLC. 2.07 μmol was obtained by lyophilization after purification, and the purity was also confirmed using HPLC (Purity; >95% (HPLC), yield: 83%).

Figure 10:
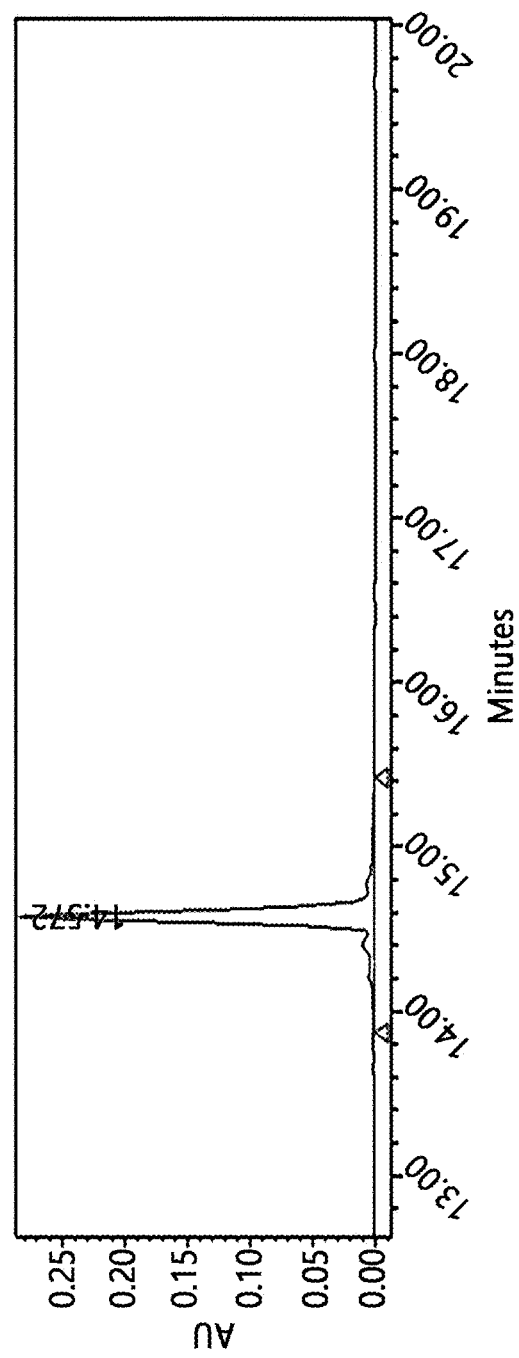
FIG. 10 illustrates the HPLC results of Compound I -FcBP(6Lys)-norbornene.

The results are illustrated in FIG. 10.

Example 4-2-2: Confirmation of structure of Compound I -FcBP(6Lys)-norbornene The synthesis of Compound I-FcBP(6Lys)-norbornene was confirmed by LC mass-based molecular weight measurement.

Figure 11:
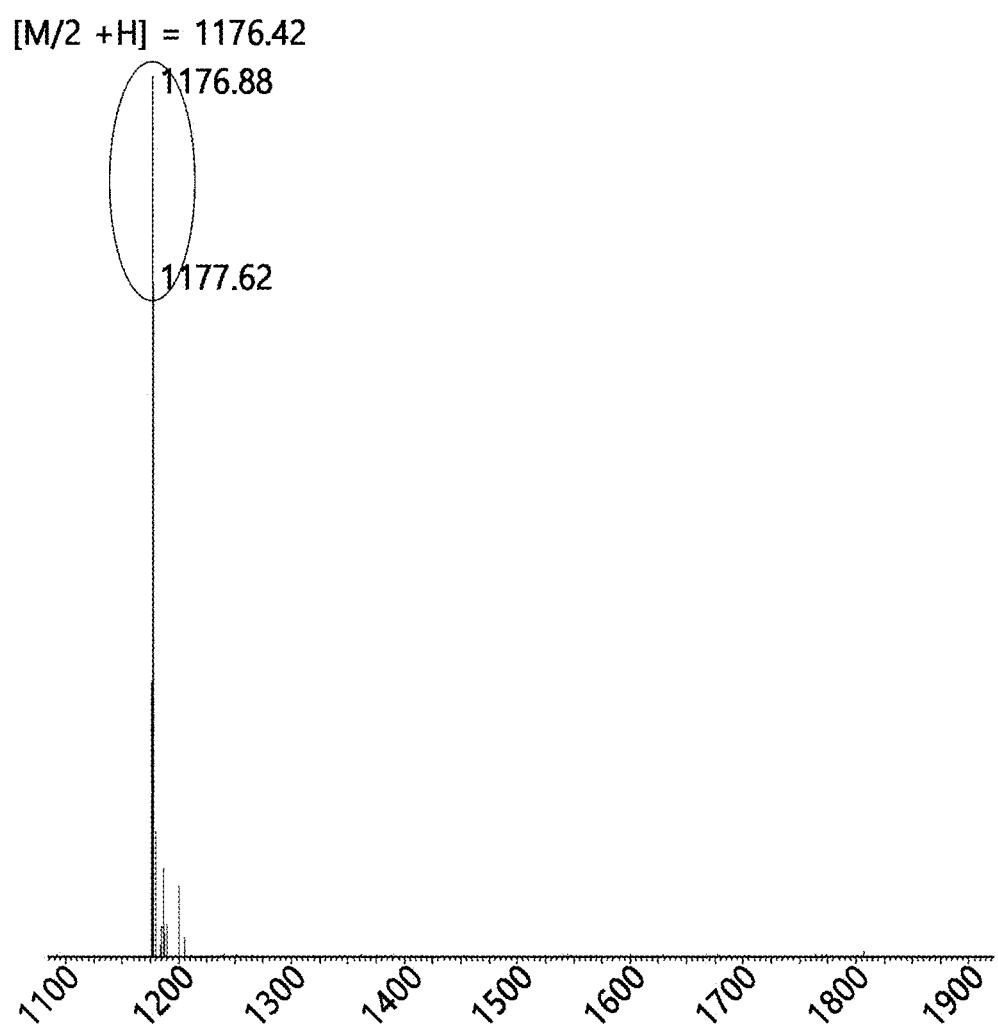
FIG. 11 illustrates the LC mass results of Compound I-FcBP(6Lys)-norbornene.

Measurement apparatus: Waters Quattro Premier XE
Calculated molecular weight: 2351.69 g/mol
Measured molecular weight $(M/2+H)^2+$: 1176.42 g/mol
The results are illustrated in FIG. 11.

Example 4-3. Synthesis and confirmation of structure of Compound H -FcBP(6Lys)-Norbornene

[Formula 12]

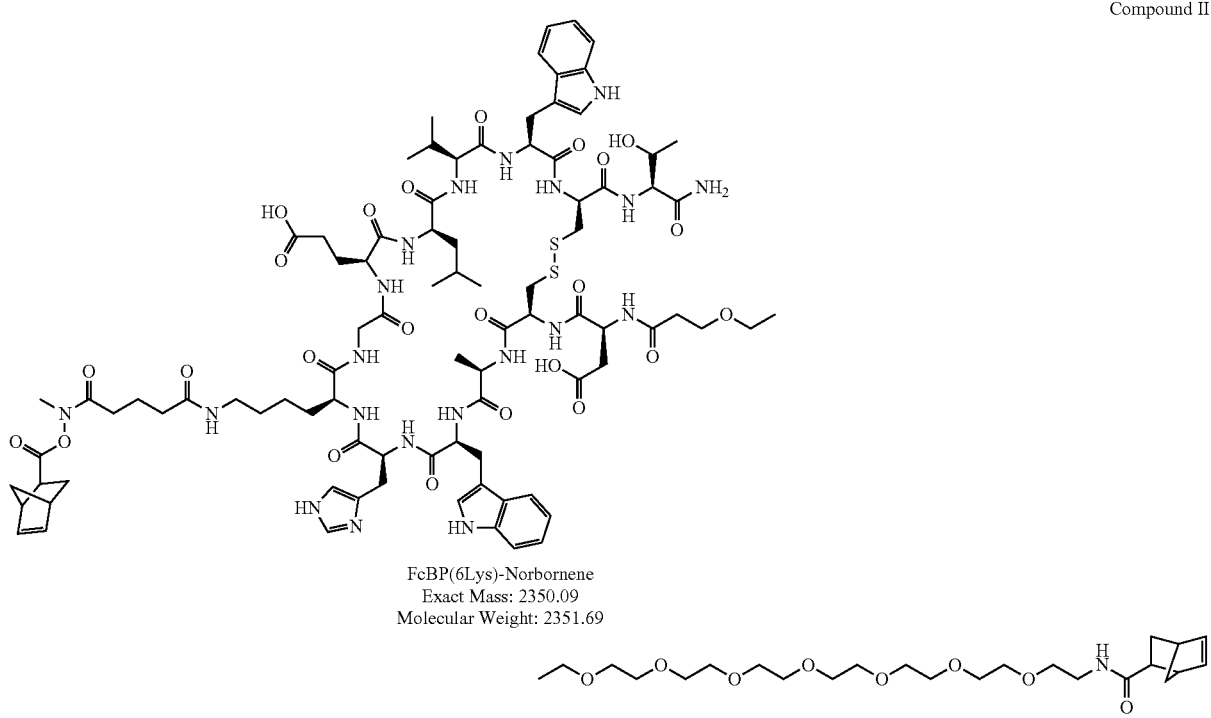

Example 4-3-1: Synthesis of Compound H -FcBP (6Lys)-norbornene

Compound H (cis-norbornene Weinreb amide)-FcBP was synthesized in DMF, and in order to introduce Compound II into FcBP (6Lys)-norbornene, 3 eq of DIPEA and 3 μmol of Compound II were dissolved in 2.5 μmol of FcBP (6Lys)-norbornene dissolved in DMF, and the resulting solution was stirred.

To confirm the introduction reaction, analysis was performed by HPLC, and when the reaction was not terminated, the termination of the reaction was observed by adding DIPEA therein in 1 eq increments.

After the termination of the reaction was confirmed, the reaction solution was concentrated and II-FcBP (6Lys)-norbornene was purified through Preparative-HPLC. 2.02 μmol was obtained by lyophilization after purification, and the purity was also confirmed using HPLC (Purity; >95% (HPLC), yield: 81%).

Figure 12:
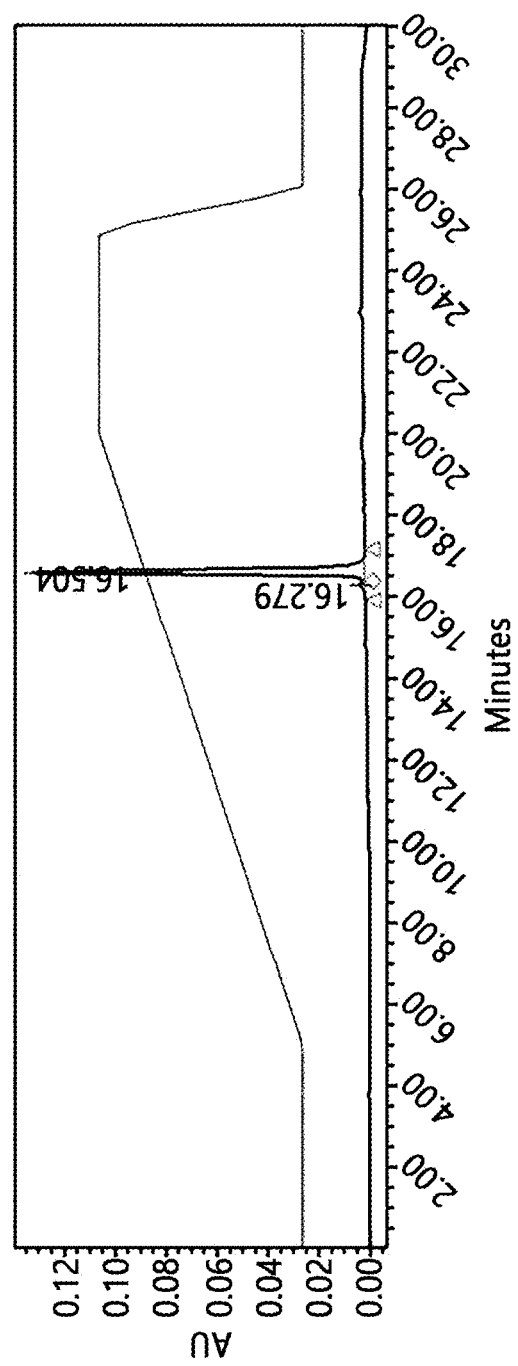
FIG. 12 illustrates the HPLC results of Compound II-FcBP(6Lys)-norbornene.

The results are illustrated in FIG. 12.

Example 4-3-2: Confirmation of Compound H -FcBP (6Lys)-norbornene

Figure 13:
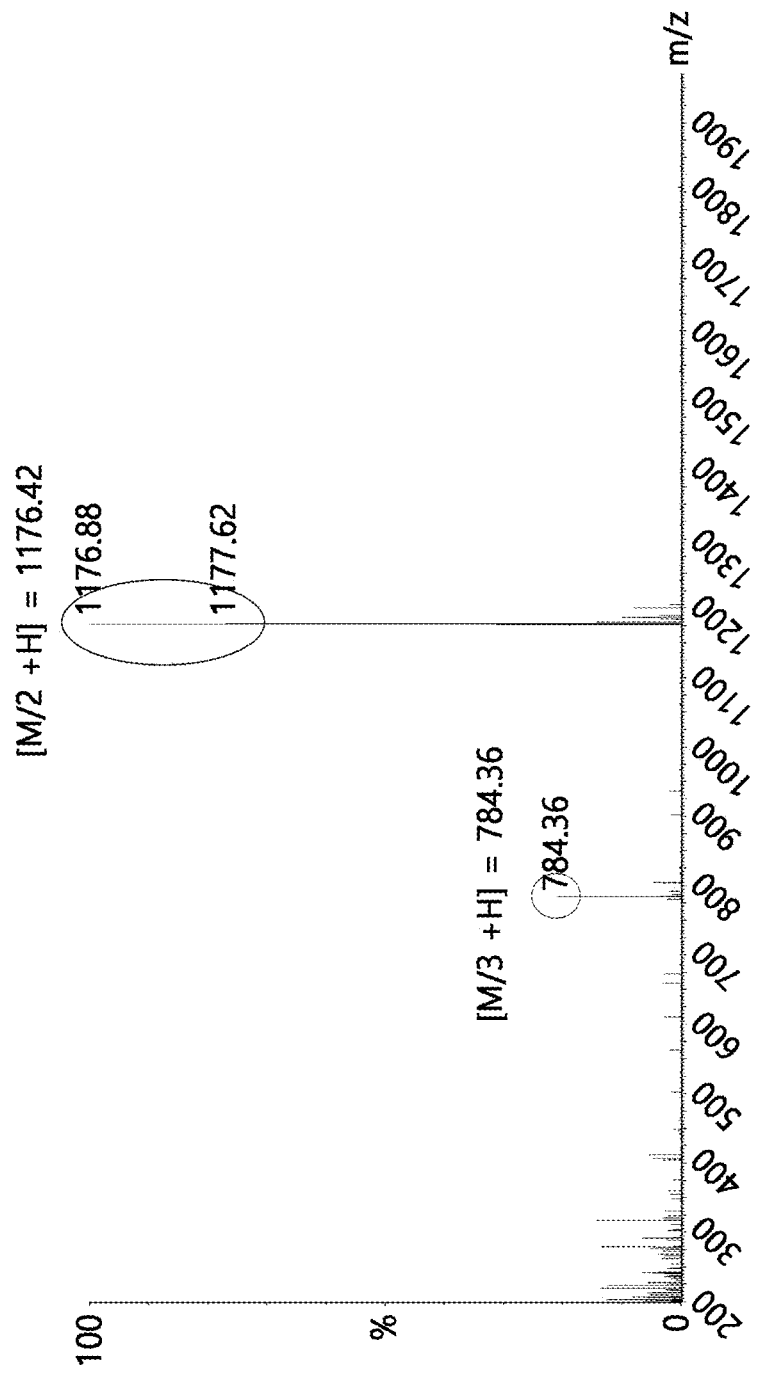
FIG. 13 illustrates the mass spectrometer results of Compound II-FcBP(6Lys)-norbornene.

Measurement apparatus: Waters Quattro Premier XE
Calculated molecular weight: 2351.69 g/mol
Measured molecular weight $(M/2+H)^{2+}$: 1176.42 g/mol
The results are illustrated in FIG. 13.

[Example 5] Synthesis method and Confirmation of structure of antibody-click chemistry chemical Example 5-1: Antibody-Norbornene Example 5-1-1: Synthesis method (1) of trastuzumab-norbornene Introduction reaction using Compound I-FcBP (6Lys)-norbornene Ab(Lys 246/248)-norbornene was synthesized using Compound I-FcBP (6Lys)-norbornene in a phosphate buffered saline (PBS) buffer with pH 7.4. In order to introduce norbornene into two specific sites of the antibody, 6 eq of Compound I-FcBP(6Lys)-norbornene per antibody was put into a reaction solution, and then the reaction was performed. The reaction took 1 week or more at room temperature, and reaction monitoring and termination were confirmed by HIC-HPLC. For purification, purification was performed via three times of dialysis (pH 5.5, 20 mM histidine acetate buffer) and a size exclusion chromatography (molecular weight cut-off 40 kDa).

Figure 14:
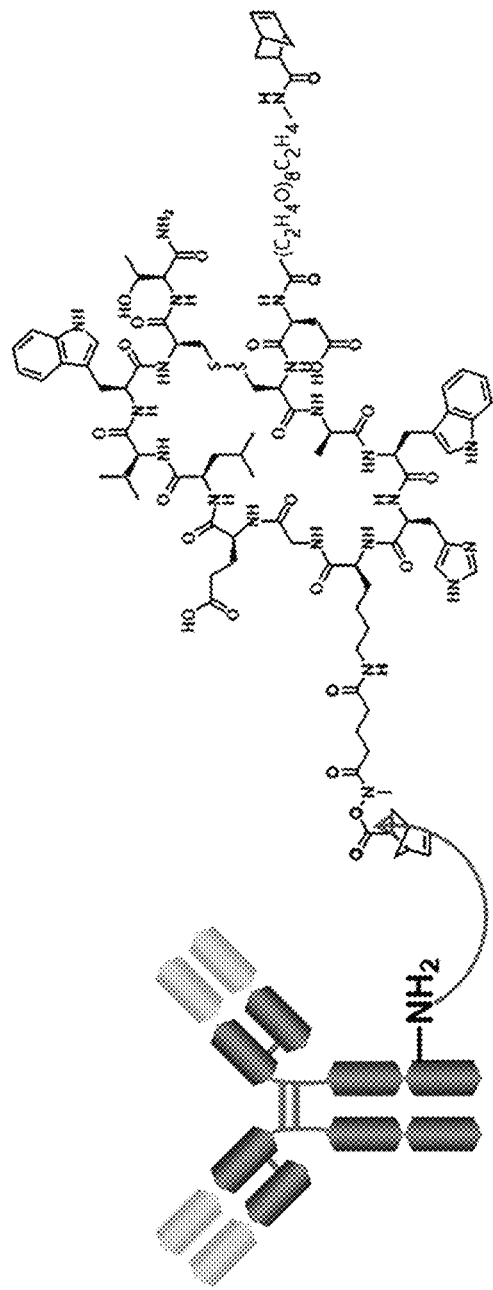
FIG. 14 illustrates a reaction of Compound I-FcBP(6Lys)-norbornene with an antibody.
Figure 15:
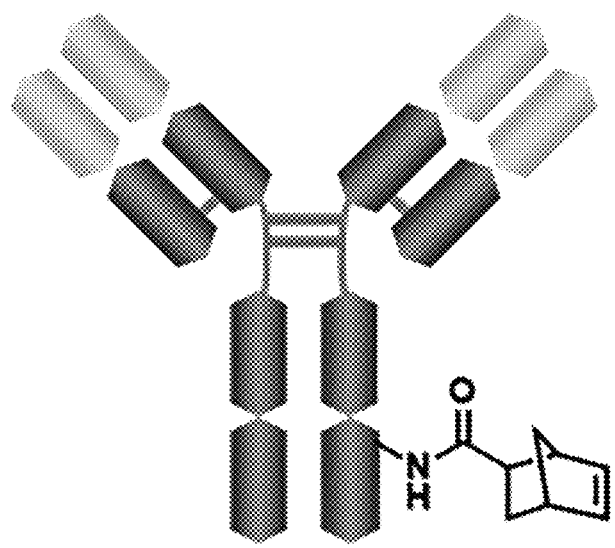
FIG. 15 illustrates a structure of Ab (Lys 246/248)-norbornene produced by a reaction of Compound I-FcBP (6Lys)-norbornene with an antibody.
Figure 16:
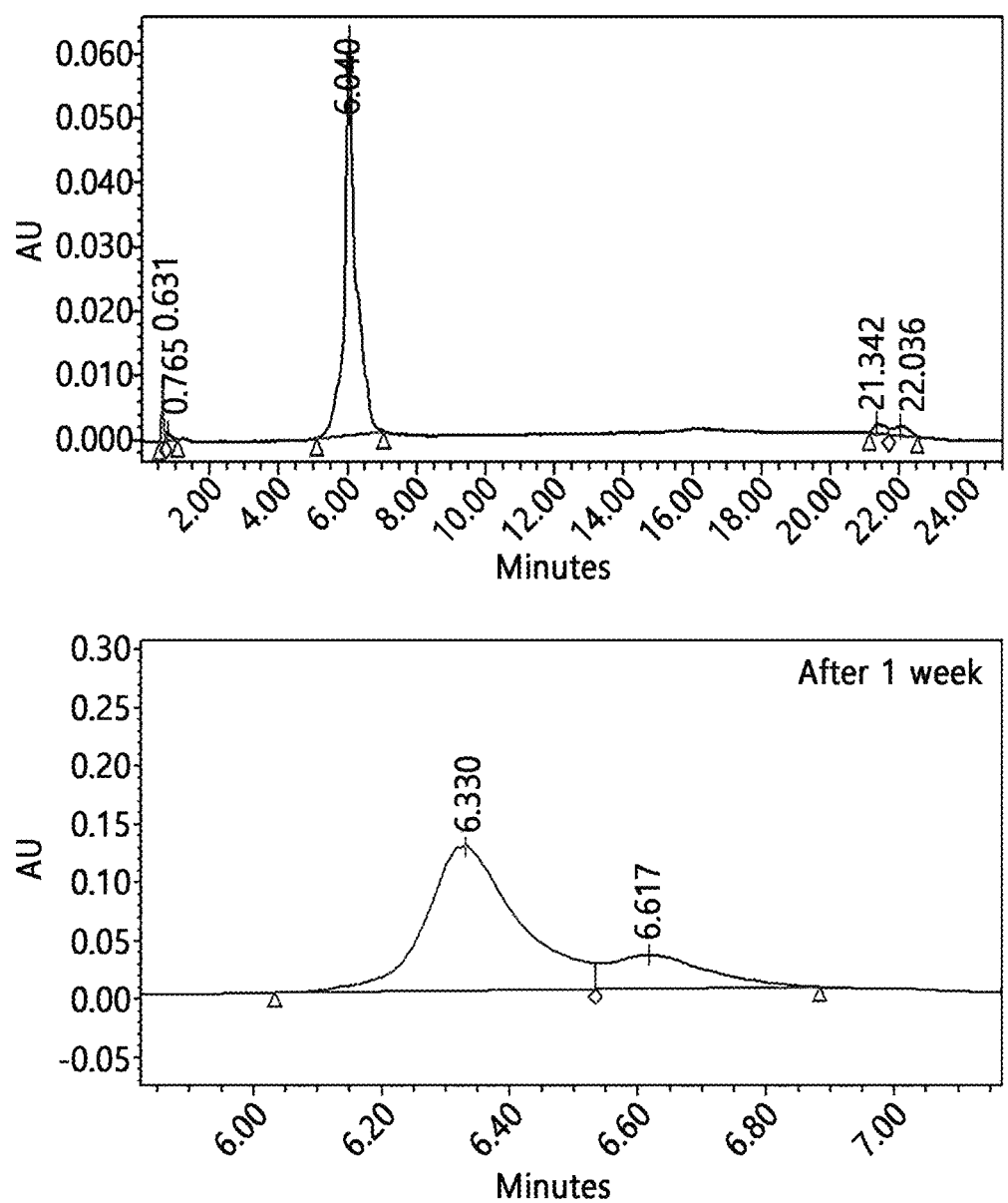
FIG. 16 illustrates the results of reaction monitoring of a reaction of Compound I-FcBP(6Lys)-norbornene with an antibody through HIC-HPLC.

The reaction of Compound I-FcBP(6Lys)-norbornene with the antibody is illustrated in FIG. 14, the structure of a final product Ab(Lys 246/248)-norbornene is illustrated in FIG. 15, and the reaction monitoring by HIC-HPLC is illustrated in FIG. 16.

Example 5-1-2: Synthesis method (2) of trastuzumab-norbornene

Introduction reaction using Compound I -FcBP(6Lys)-norbornene

Ab(Lys 246/248)-norbornene was synthesized using Compound II-FcBP (6Lys)-norbornene in a phosphate buffered saline (PBS) buffer with pH 7.4. In order to introduce norbornene into two specific sites of the antibody, 6 eq of Compound II-FcBP (6Lys)-norbornene per antibody was put into a reaction solution, and then the reaction was performed. The reaction was performed for 12 hours at room temperature, and reaction monitoring and termination were confirmed by HIC-HPLC. Purification was performed via three times dialysis (pH 5.5, a 20 mM histidine acetate buffer) and a size exclusion chromatography (molecular weight cut-off 40 kDa) to obtain 135 mg results from 150 mg of trastuzumab. (yield=90%)

Figure 17:
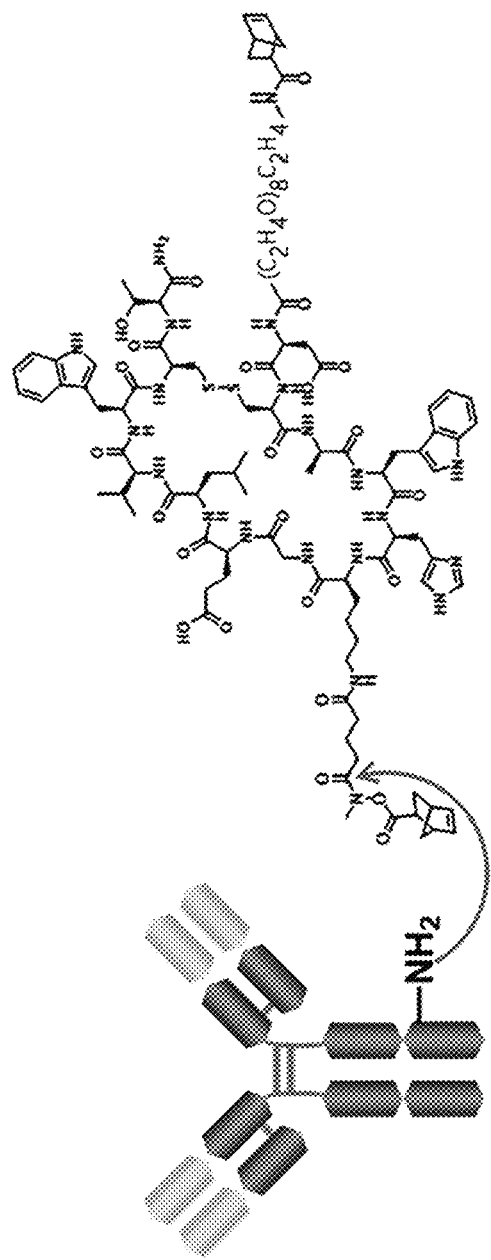
FIG. 17 illustrates a reaction of Compound II-FcBP (6Lys)-norbornene with an antibody.
Figure 18:
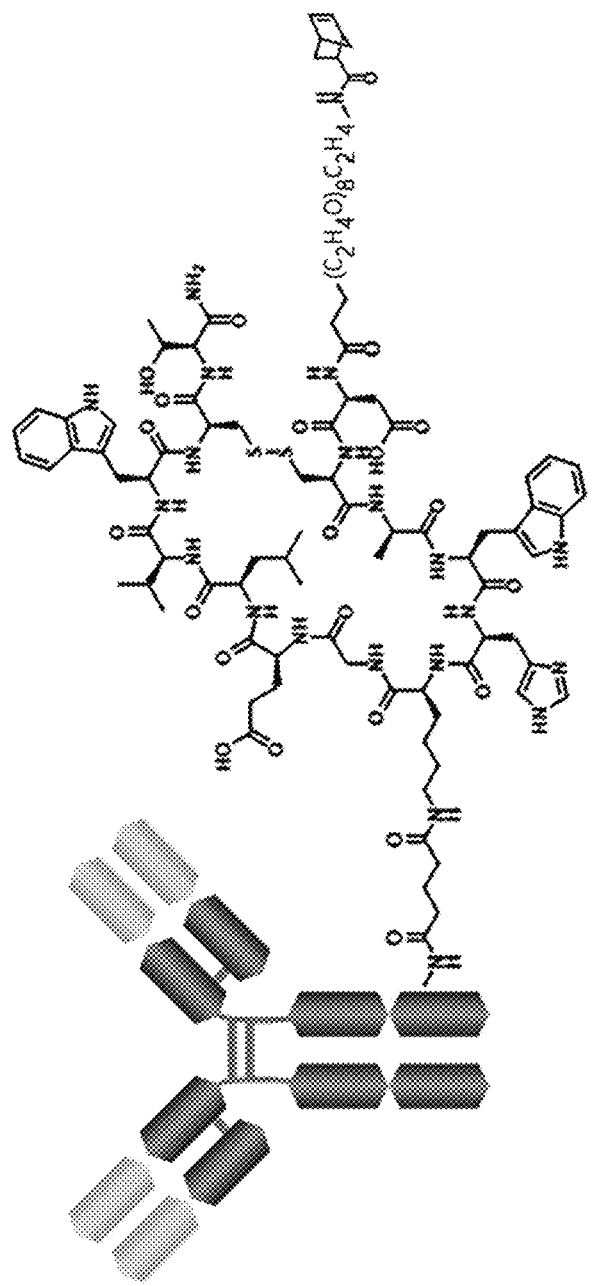
FIG. 18 illustrates a structure of Ab(Lys 246/248)-norbornene produced by a reaction of Compound I-FcBP (6Lys)-norbornene with an antibody.
Figure 19:
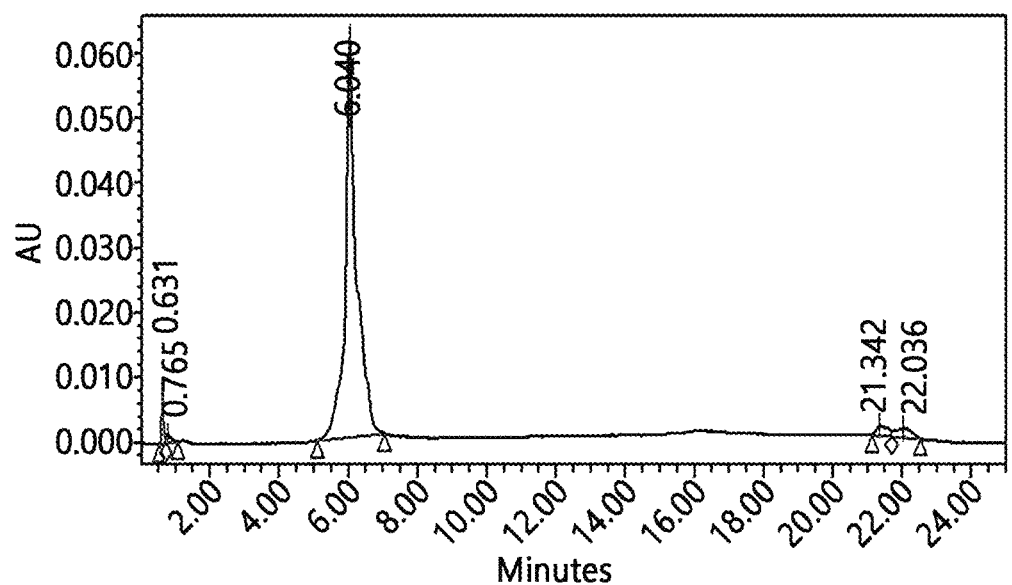
FIG. 19 illustrates the results of reaction monitoring of a reaction of Compound II-FcBP(6Lys)-norbornene with an antibody through HIC-HPLC.
Figure 19:
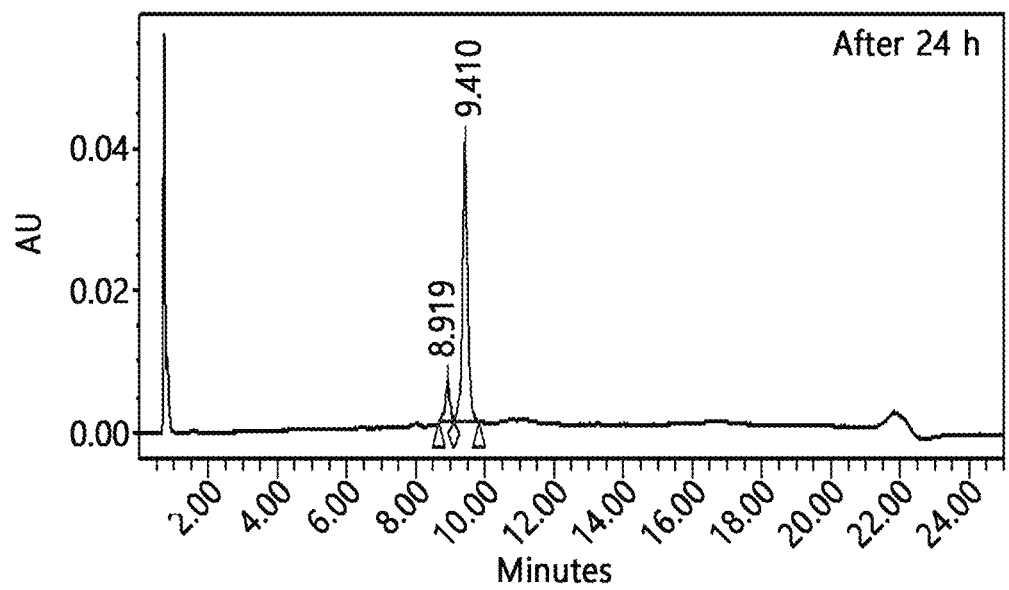

The reaction of Compound II-FcBP(6Lys)-norbornene with the antibody is illustrated in FIG. 17, and the structure of the product Ab(Lys246/248)-norbornene is illustrated in FIG. 18. Reaction monitoring by HIC-HPLC is illustrated in FIG. 19.

Example 5-2-1: Confirmation of Herceptin-norbornene binding

The confirmation of an antibody intermediate (FIG. 18) in which a FcBP norbornene linker was included in the antibody was verified based on mass spectrometry.

Figure 20:
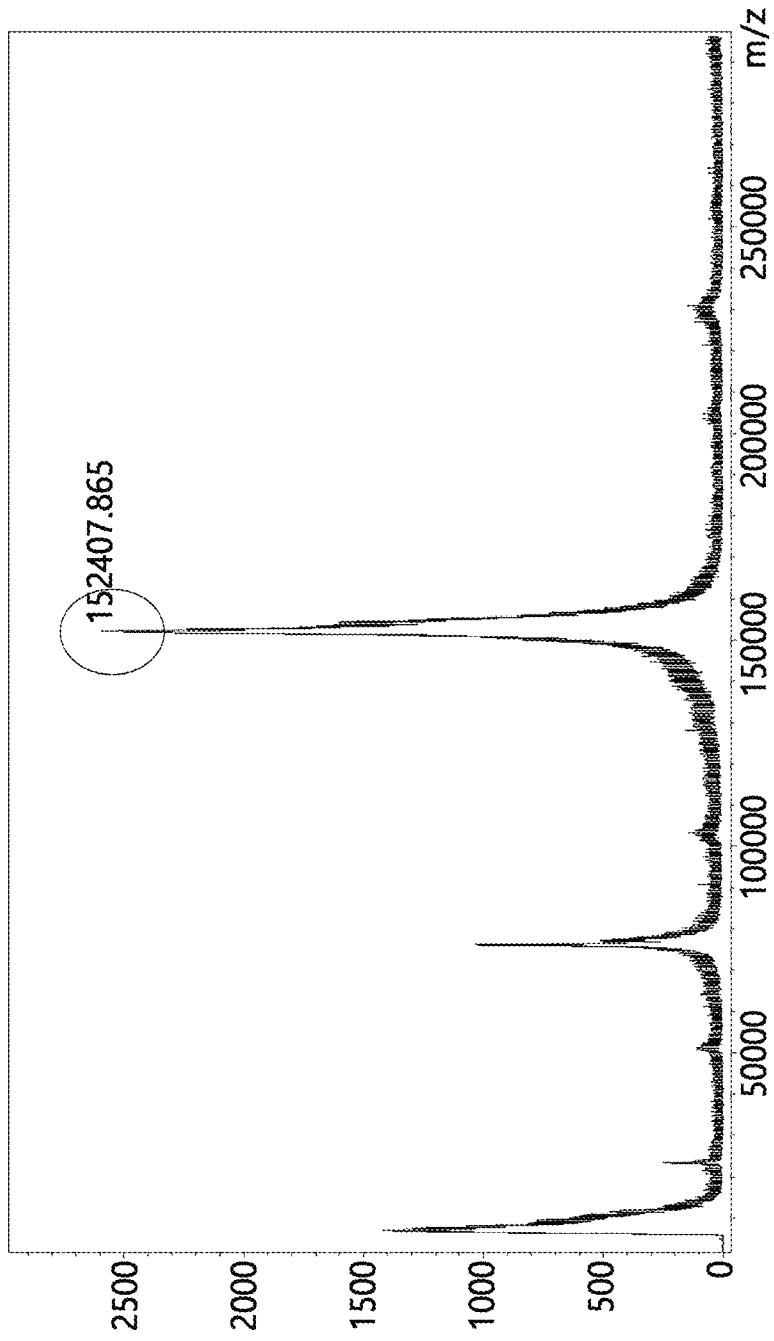
FIG. 20 illustrates the mass analysis results of Herceptin-norbornene.

Measurement apparatus: Ultraflex III (TOF/TOF)
Analysis mode: Linear mode
Polarity: Positive
Detection: m/z 2,000 to 300,000
Laser repetition rate: 100 Hz
Number of shots: 1,000 shots
Deflection: On, 5,000 Da
Voltage: Ion Source I 25.00 kV, Ion Source II 23.00 kV, Lens 9.00 kV
Calculated molecular weight: 152,385 g/mol
Measured molecular weight: 152,407 g/mol (M+Na)
The analysis results are illustrated in FIG. 20.

[Example 6] Synthesis and confirmation of antibody drug conjugate

Example 6-1: Antibody-drug conjugation

Example 6-1-1: Synthesis method of trastuzumab-DM1

The synthesis of an antibody-payload conjugate was performed using trastuzumab in which two molecules of norbornene were introduced by Compound II-FcBP(6Lys)-norbornene (FIG. 18). The reaction was performed at a concentration of 4.5 mg/mL using an amount of 25 mL, and conjugation of the Tetrazine-PEG8-DM1 drug was attempted for biorthogonal chemistry with norbornene conjugated to the antibody. 4 eq of a drug was used compared to the antibody, and the conjugation reaction was performed in a 20 mM histidine acetate solution with pH 5.5 at room temperature for 24 hours. The observation of the conjugation reaction was confirmed by HIC-HPLC, and the production of an antibody-payload conjugate was observed by observing that the peak in the 9.4 minute range, that appeared when only the FcBP linker was bound to trastuzumab, is changed to the 11.2 minute range as the antibody-FcBP linker reacted with the drug.

Figure 21:
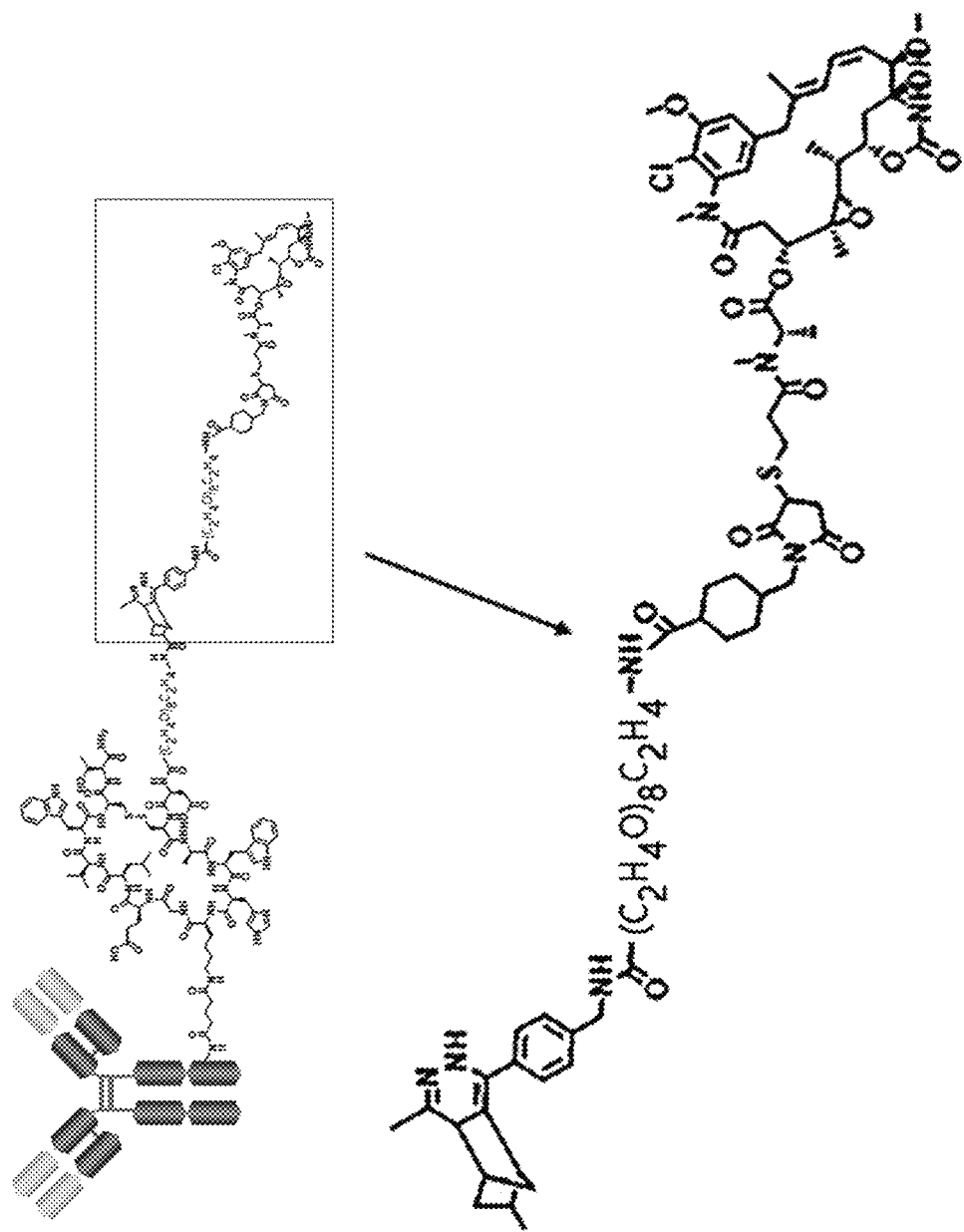
FIG. 21 illustrates the structure of an antibody-payload conjugate produced using an antibody including a first click chemistry functional group in FIG. 18. The enlarged structure is the structure of a payload, and the unenlarged part is the same as the structure illustrated in FIG. 18.
Figure 22:
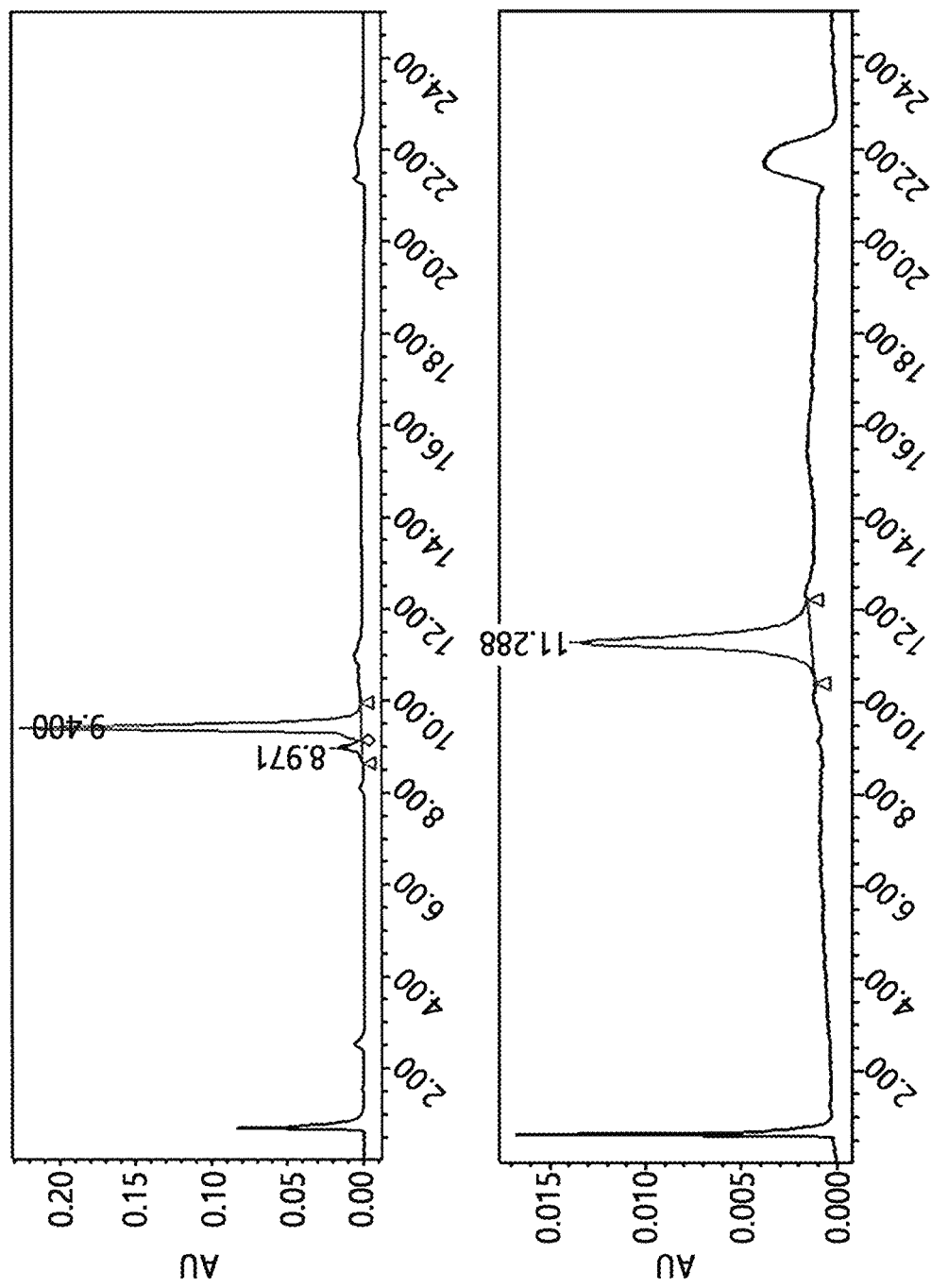
FIG. 22 illustrates the results of reaction monitoring of a reaction of Ab(Lys 246/248)-norbornene in FIG. 18 with tetrazine-PEG8-DM1 through HIC-HPLC.

The structure of the product antibody-payload conjugate is illustrated in FIG. 21, and reaction monitoring by HIC-HPLC is illustrated in FIG. 22. In FIG. 21, the enlarged structure is the structure of a payload, and the unenlarged part is the same as the structure illustrated in FIG. 18.

Example 6-1-2: Trastuzumab-DM1 purification method

In order to obtain a high-purity antibody-payload conjugate, dialysis using a 20 mM histidine acetate solution with pH 5.5 and HIC purification using fast protein liquid chromatography (FPLC) were performed.

HIC purification conditions are as follows.
FPLC Model: AKTA pure
Flow rate: 1 mL/min
Column: HiPrep butyl FF16/10 column
Elution solvent: (A) 1.5 M Ammonium sulfate+50 mM phosphate pH 7.0
(B) 50 mM Phosphate pH 7.0
Elution conditions
0:00-10:00 A:40%, B:60%
10:00-20:00 A:65%, B:35%
20:00-102.5:00 A:75%, B:25%
102:5-115:00 A:100%, B:0%
115:00-135:00 A:100%, B:0%

The HIC chromatogram of the purified antibody-payload conjugate is illustrated in FIG. 19.

By the above method, 67 mg of trastuzumab-DM1 in which a drug was conjugated to two sites (Drug Antibody Ratio=2) was obtained. (yield=60%)

Example 6-1-3: Confirmation of trastuzumab-DM1 binding

The confirmation of an antibody-payload conjugate including a FcBP linker and a drug was verified based on mass spectrometry.

Figure 23:
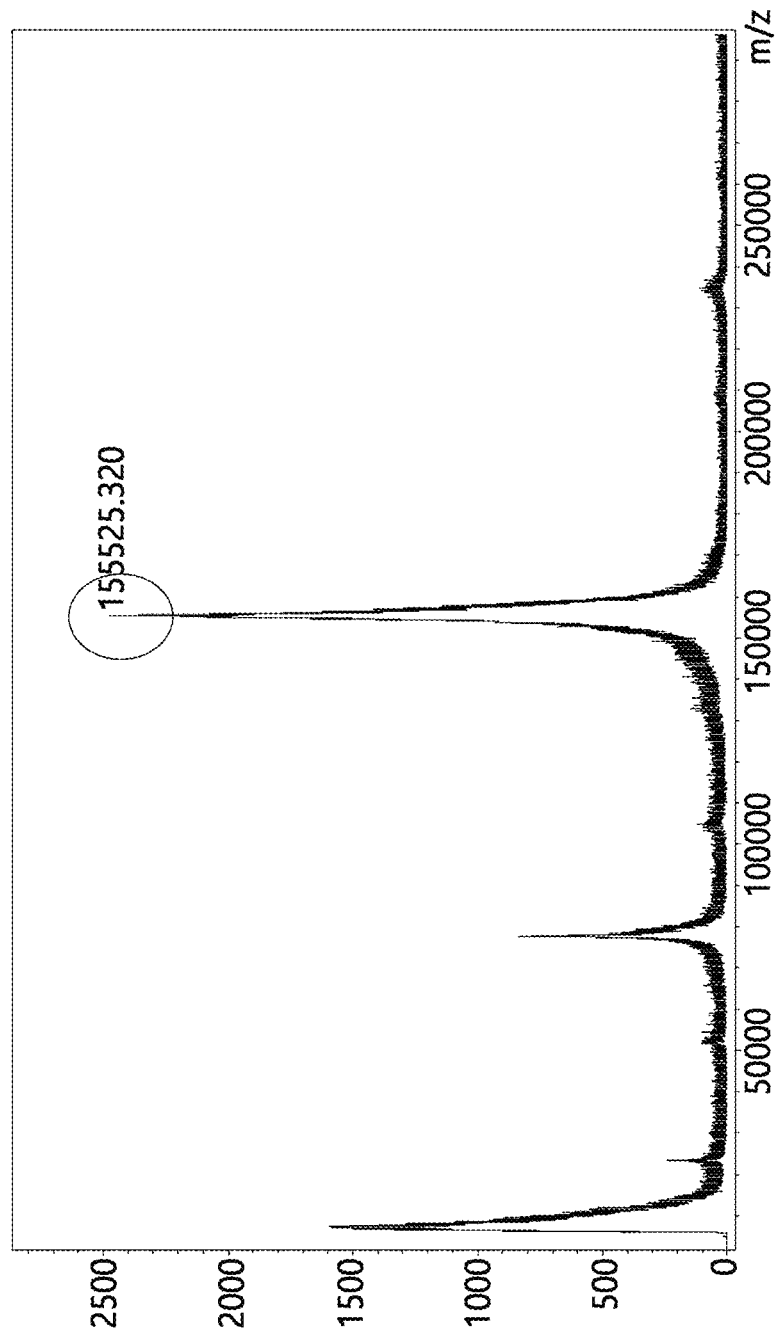
FIG. 23 illustrates the mass analysis results of an antibody-payload conjugate.
Figure 24:
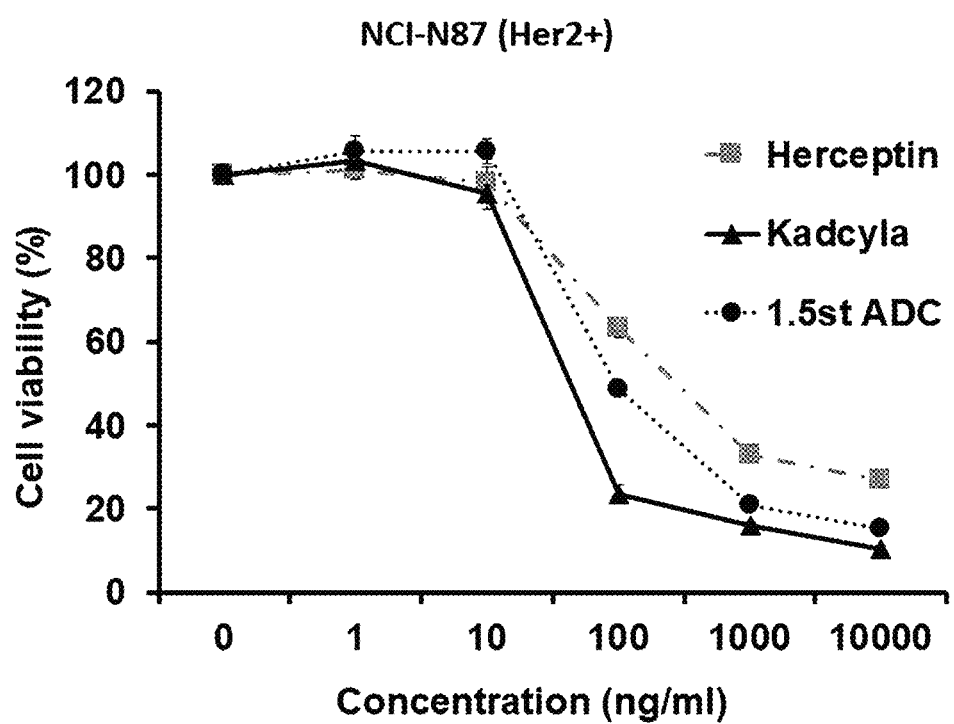
Figure 25:
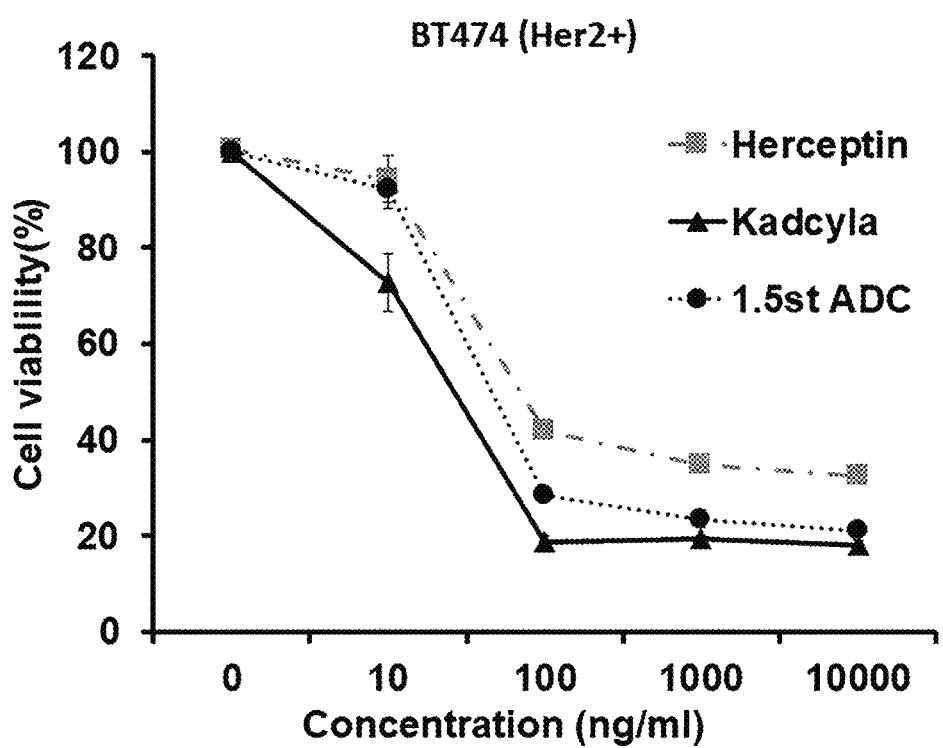
Figure 26:
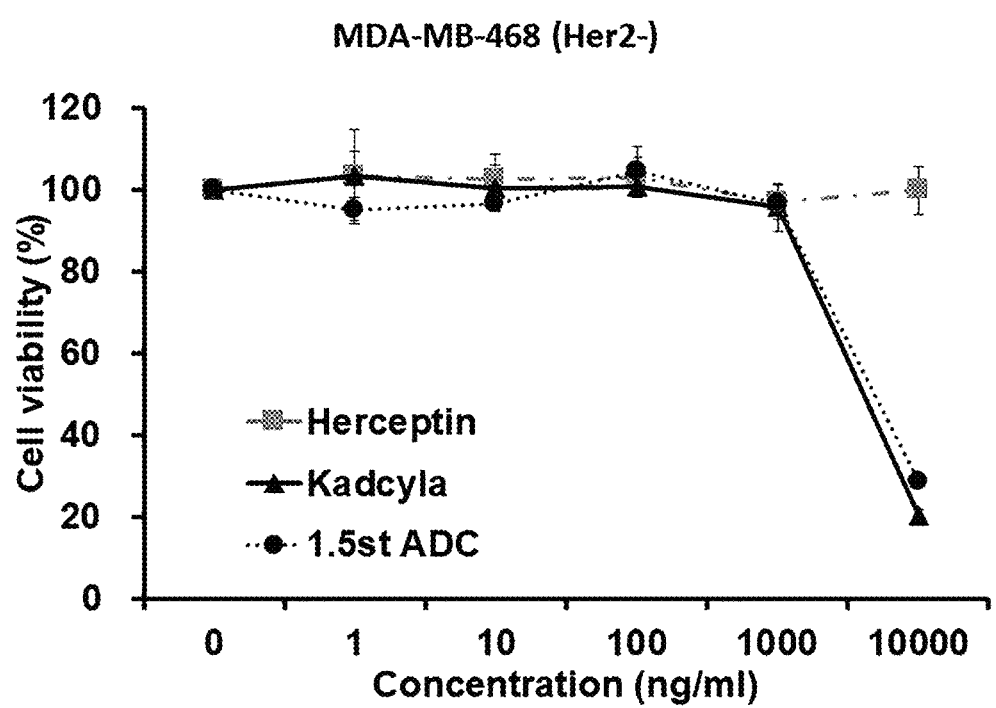

Measurement apparatus: Ultraflex III (TOF/TOF)
Analysis mode: Linear mode
Polarity: Positive
Detection: m/z 2,000 to 300,000
Laser repetition rate: 100 Hz
Number of shots: 1,000 shots
Deflection: On, 5,000 Da
Voltage: Ion Source I 25.00 kV, Ion Source II 23.00 kV, Lens 9.00 kV
Calculated molecular weight: 155,493 g/mol
Measured molecular weight: 155,523 g/mol (approx. M+Na)
The analysis results are illustrated in FIG. 23.

[Example 7] Evaluation of medicinal efficacy at cellular level (in vitro cytotoxicity test) of novel antibody-drug conjugate (ADC, trastzumab-DM1 conjugate)

The efficacy of the antibody-payload conjugate (ADC, trastuzumab-DM1 conjugate) was evaluated based on the target marker level of cancer cells, and cytotoxicity experiments were performed using NCI-N87 and BT474 for the positive expression cell lines of the target antigen Her2 and MDA-MB-468 for the negative cell lines. In Her2-overexpressing cells NCI-N87 and BT474, as a result of observation by treating the cells with a produced antibody drug conjugate at each concentration, excellent anticancer effects with IC50 values of 82.1 ng/mL and 29.6 ng/mL were confirmed. When compared to the commercialized Herceptin ADC, Kadcyla, the effect was confirmed at the equivalent level, so that the utility as a new ADC could be confirmed.

The results for the experiments are illustrated in FIGS. 24 to 27.

[Example 8] Evaluation of medicinal efficacy at animal level (in vivo cytotoxicity test) of novel antibody-payload conjugate (ADC, trastzumab-DM1 conjugate)

A xenograft model was prepared by subcutaneously transplanting an NCI-N87 gastric cancer cell line overexpressing a target antigen, and an anticancer efficacy test was performed on the administered materials, by classifying the xenograft model into four groups. Since the BALB/c nude mouse used in the present experiment is deficient in T cells, cancer cells are easily transplanted into the mouse, so that the mouse was used as model suitable for an anticancer efficacy test using rodents.

(a) Preparation of Cell Line

A RPM11640 medium (Gibco, 22400-089) containing heat-inactivated 10% fetal bovine serum (FBS, Gibco, 10082-742) was put into a cell culture flask, and 1 vial of a human tumor cell line (NCI-N87 cell line) was added thereto and cultured in a 5% CO2 incubator at 37° C. The cultured flask was washed using PBS, and after the cells were isolated by diluting 2.5% trypsin-EDTA (Gibco, 15090) 10-fold, and then adding the diluted trypsin-EDTA thereto, the supernatant was discarded after centrifuging the cells (1,000 rpm, 5 minutes), and then a cell suspension was obtained with a new medium. After viability was confirmed using a microscope, a cell line was prepared by diluting the cell suspension in a solution in which the medium at a concentration of $1.25 \times 10^7$ cells/mL and Matrigel were mixed at 1:1.

(b) Transplantation of Cell Line

A cell line is prepared according to the method described in '4. 3) (4) Preparation of cell line'. When the cell line was prepared, the cell line was re-suspended and homogenized, and the prepared cell line was immediately administered to an animal. When the cell line was transplanted, the back part of the animal was disinfected with 70% alcohol, a space was created between the skin and the muscle by pulling the skin on the back of the neck with the thumb and the index finger, and then an injection needle equipped with a 26 gauge needle was inserted into a subdermal space between the thumb and the index finger from the front of the animal to subcutaneously administer the cell line at a dose of $2.5 \times 10^6$ cells/0.2 mL/head. During the acclimatization period healthy animals were selected, and selected animals are inoculated with the cell line Thus, when the size at the site of transplantation of the cell line reached about 100 to 150 mm$^3$, according to the size of tumor ranked, distribution is made so that the size of the tumor in each group is distributed as evenly as possible.

(c) Determination of Test Group Configuration, Dosage, and Administration Method Cell line=NCI-N87

Mouse type=BALB/c nude (CAnN.Cg-Foxn1 nu/CrljOri)

Number of groups=5

Administration method=Use of intravenous injection (26 gauge needle syringe)

Dosage=5 mg/kg

Number of doses=once/2 days, three-time administration

Observation period=5 weeks

Group 1: PBS, Group 2: Herceptin (Trastuzumab), Group 3: Newly manufactured ADC (Herceptin-DM1 Conjugate, 1.5st ADC)

(d) Observation and Examination Items

General Symptoms

During the administration and observation period, the types of general symptoms including death, the date of onset and the degree of symptoms were observed once a day and recorded for each individual. Individuals experiencing aggravated general symptoms are quarantined.

Body Weight

Body weight is measured on the day of group separation or the start of administration of the test material, and then twice/week after that.

Measurement of Tumor Size

The size of the tumor is measured 2 times/week for 5 weeks from the start date of administration of the test material. The major axis and minor axis of the tumor were measured using calipers, and the tumor size was calculated using the following equation.

Tumor size=$ab^2/2$ (a: major axis length, b: minor axis length)

(e) Results

The group injected with phosphate buffered saline (PBS) and Herceptin (trastuzumab) showed no tendency of suppressing tumor growth during a 5-week observation period. The antibody-payload conjugate (Herceptin-DM1) produced by the present application was confirmed to have an excellent ability of suppressing tumor growth compared to Herceptin, so that it was confirmed that the antibody-payload conjugate functioned successfully as an ADC.

Figure 28:
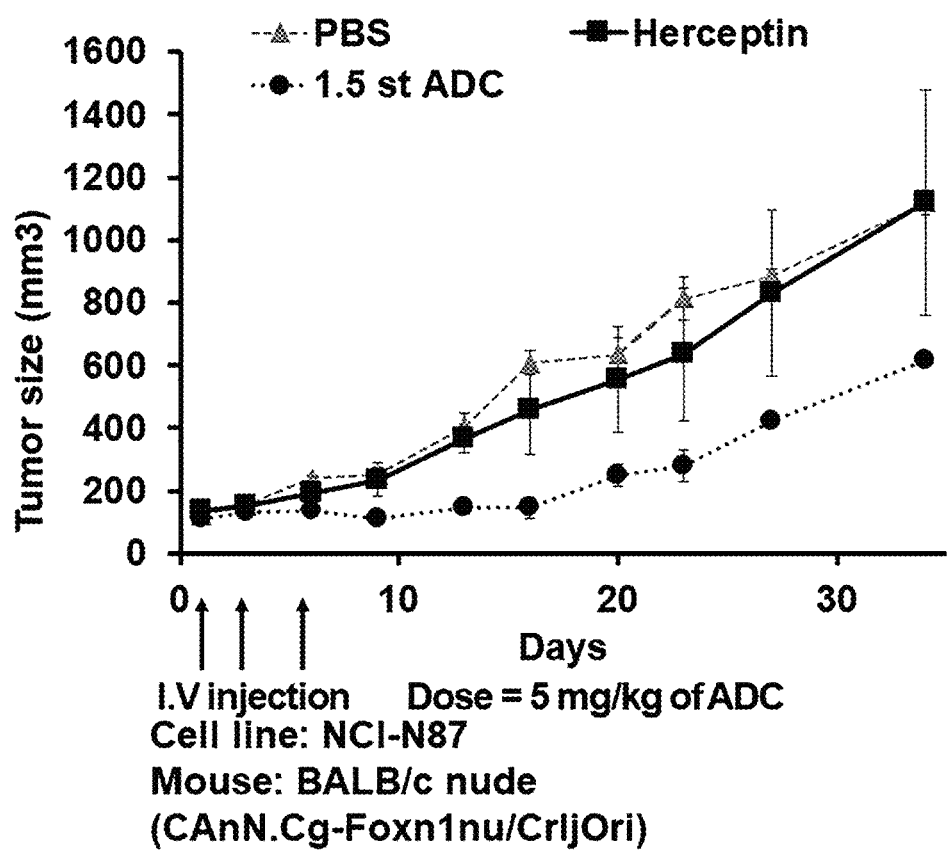
FIGS. 28 and 29 illustrate the results of a tumor growth suppression experiment of Herceptin and an antibody-payload conjugate according to the present application.
Figure 29:
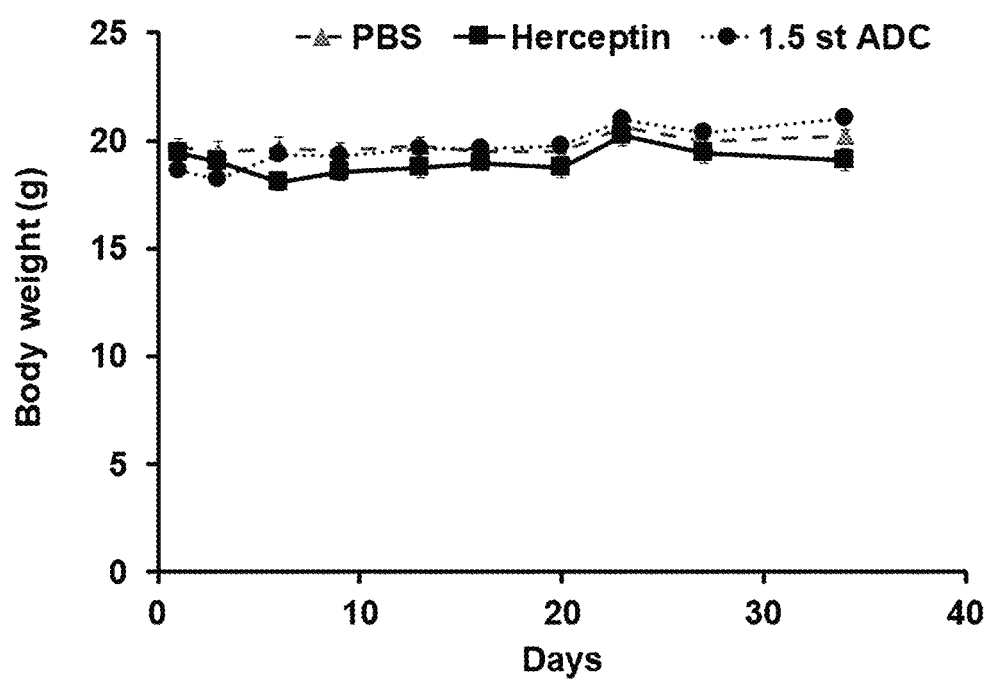

The above related results are illustrated in FIGS. 28 and 29.

[Example 9] Synthesis and confirmation of site-specific interactome according to carbon length Example 9-1. Synthesis and confirmation of structure of Compound II-FcBP(L6Dap, L6Dab, L6Orn, L6Lys)-Norbornene

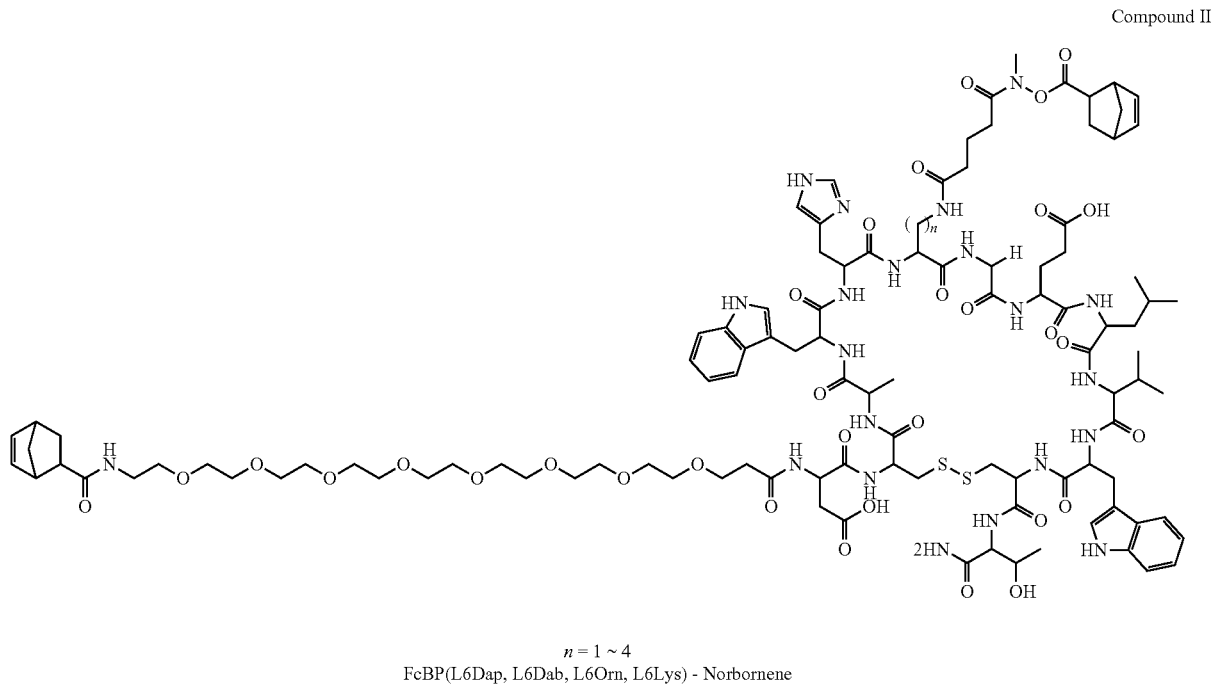

Compound II $n = 1 \sim 4$
FcBP(L6Dap, L6Dab, L6Orn, L6Lys) - Norbornene

Example 9-1-1: Synthesis of FcBP (L6Dap, L6Dab, L6Orn, L6Lsy)-Norbornene

FcBP(LDab): Lsthesissed FcBminoad. andab reron ntodutioo used Fmoc amino acids (n=21)

Fmoc-L-Thr(tBu)-OH, Fmoc-Cys(Trt)-OH, Fmoc-L-Trp(Boc)-OH, Fmoc-L-Val-OH, Fmoc-L-Leu-OH, Fmoc-L-Glu(OtBu)-OH, Fmoc-Gly-OH, Fmoc-Dab(Boc)-OH, Fmoc-L-His(Trt)-OH, Fmoc-L-Trp(Boc)-OH, Fmoc-Ala-OH, Fmoc-Cys(Trt)-OH, Fmoc-Asp(tBu)-OH.

FcBP(L6Orn):List of used Fmoc amino acids and order of introduction of used Fmoc amino acids (n=2)

Fmoc-L-Thr(tBu)-OH, Fmoc-Cys(Trt)-OH, Fmoc-L-Trp(Boc)-OH, Fmoc-L-Val-OH, Fmoc-L-Leu-OH, Fmoc-L-Leu-OH, Fmoc-L-Glue(OtBu)-OH, Fmoc-Gly-OH, Fmoc-Dab(Boc-OH, Fmoc-L-His(Trt)-OH, Fmoc-L-Trp(Boc)-OH, Fmoc-Ala-OH, Fmoc-Cys(Trt)-OH, Fmoc-Asp(tBu)-OH.

FcBP(L6O): List of used Fmoc amino acids and order of introduction of used Fmoc amino acids (n=3)

Fmoc-L-Thr(tBu)-OH, Fmoc-Cys(Trt)-OH, Fmoc-L-Trp(Boc)-OH, Fmoc-L-Val-OH, Fmoc-L-Leu-OH, Fmoc-L-Glu(OtBu)-OH, Fmoc-Gly-OH, Fmoc-Orn(Boc)-OH, Fmoc-L-His(Trt)-OH, Fmoc-L-Trp(Boc)-OH, Fmoc-Ala-OH, Fmoc-Cys(Trt)-OH, Fmoc-Asp(tBu)-OH.

FcBP(L6Lys): List of used Fmoc amino acids and order of introduction of used Fmoc amino acids (n=4)

Fmoc-L-Thr(tBu)-OH, Fmoc-Cys(Trt)-OH, Fmoc-L-Trp(Boc)-OH, Fmoc-L-Val-OH, Fmoc-L-Leu-OH, Fmoc-L-Glu(OtBu)-OH, Fmoc-Gly-OH, Fmoc-Lys(Boc)-OH, Fmoc-L-His(Trt)-OH, Fmoc-L-Trp(Boc)-OH, Fmoc-Ala-OH, Fmoc-Cys(Trt)-OH, Fmoc-Asp(tBu)-OH.

Production Method (a) Introduction of Amino Acids

The amount of reagent used in the following process was based on 0.25 mmole. 0.5 g of a clear amide resin (0.48 mmole/g, Peptides International, USA) was put into a synthesis reactor, and 1 mmole of each Fmoc-amino acid block weighed and prepared in the order of the peptide amino acid sequence from the C-terminal to the N-terminal.

A reaction of attaching the activated residue to the clear amide resin by activating the Fmoc-amino acid was performed, and the reaction is performed sequentially from the C-terminal amino acid.

The removal of Fmoc was performed in 20% piperidine-containing DMF. And in order to the activation and introduction of the residue, amino acids prepared according to the sequences were mixed with 2 mL of a 0.5 M HOBt-containing DMF solution, 2 mL of a 0.5 M HBTU-containing DMF solution, and 174 µL of DIPEA for 5 minutes, and then the resulting mixture was poured into a reactor containing a resin and was mixed for 2 hours.

The confirmation of the introduction reaction was performed by the Kaiser test method, and when it was confirmed that there was no reaction, the introduction reaction was repeated once more, or capping was performed with a 20% Ac$_2$O-containing DMF solution. The resin was sufficiently washed with DMF and DCM before moving on to the next step in each introduction reaction and Fmoc removal process. Such the process was performed repeatedly until a target peptide sequence was completed.

(b) Introduction of H-PEG8—OH

To introduce H-PEG$_8$-OH at the N-terminal after all amino acid introductions had been completed, 1 mL of 0.5 M Fmoc-N-amido-dPEG8-acid in a DMF solution, 1 mL of 0.5 M HBTU-containing DMF solution, 1 mL of 0.5 M HOBt-containing DMF solution, and 87 μL of DIPEA were mixed for 5 minutes, and then the resulting mixture was poured into a reactor containing a resin and was mixed for 2 hours.

The progress of the reaction was confirmed by the Kaiser test method, and when it was determined that unreacted amines remained, the reaction time was further extended by 1 to 3 hours, or the reaction solution was emptied and the aforementioned reaction process was repeated again. Removal of an N-terminal Fmoc protecting group was performed using 20% piperidine-containing DMF, and then the peptide attached resin was dried and weighed.

(c) Introduction of Norbornene

For the removal of the N-terminal Fmoc protecting group, 4 eq. of norbornene carboxylic acid, 2 mL of 0.5 M HOBt-containing DMF solution, 2 mL of 0.5 M HBTU-containing DMF solution, and 174 μL of DIPEA were mixed with a resin for 5 minutes, and then the resulting mixture was poured into a reactor containing a resin and was mixed for 2 hours. The confirmation of the introduction reaction was performed by the Kaiser test method, and when it was confirmed that there was no reaction, the introduction reaction was repeated once more.

(d) The peptide was cleaved from the resin by stirring 250 mg of peptide attached resin prepared in step (c) with 2 mL of a mixed solution of TFA, TIS, water and EDT (94:1.0:2.5:2.5) at room temperature for 120 minutes. The cleavage mixture was filtered, the filtrate was concentrated by about half with nitrogen gas, and then ether was poured to precipitate the peptide. The precipitated peptide was further washed three times with ether and dried with nitrogen gas. After the dried precipitate was dissolved in 0.1% TFA-30% ACN-containing water, the resulting solution was stirred for 6 hours, and then concentrated.

After the concentrate was dissolved in a 0.01 M ammonium acetate buffer (pH 6.5) solution containing 5%-DMSO-20%-ACN at a concentration of 0.1 mg/mL, the resulting solution was stirred in an air-exposed state for 3 days. The progress of a disulfide bond formation reaction was observed by HPLC, and when it was determined that the reaction did not proceed any further, the reaction solution was freeze-dried to obtain a peptide precipitate.

(e) Purification

The peptide precipitate obtained by lyophilization in step (d) was purified under the prep-LC conditions shown in the following Table 6 and lyophilized. It was confirmed that each of the obtained peptides had a purity of 90% or more.

(f) Sequence
    FcBP(L6Dap)-Norbornene    Norbornene-PEG8-Asp-Cys*-Ala-Trp-His-Dap-Gly-Glu-Leu-Val-Trp-Cys*-Thr-NH$_2$ (Cys*: disulfide binding site)
    FcBP(L6Dab)-Norbornene:    Norbornene-PEG8-Asp-Cys*-Ala-Trp-His-Dab-Gly-Glu-Leu-Val-Trp-Cys*-Thr-NH$_2$ (Cys*: disulfide binding site)
    FcBP(L6Orn)-Norbornene:    Norbornene-PEG8-Asp-Cys*-Ala-Trp-His-Orn-Gly-Glu-Leu-Val-Trp-Cys*-Thr-NH$_2$ (Cys*: disulfide binding site)
    FcBP(L6Lys)-Norbornene:    Norbornene-PEG8-Asp-Cys*-Ala-Trp-His-Lys-Gly-Glu-Leu-Val-Trp-Cys*-Thr-NH$_2$ (Cys*: disulfide binding site)

TABLE 6

| Prep-LC purification conditions | |
|---|---|
| Device name | Waters 2525 pump, Waters 2487 UV detector |
| Column | Waters, XBridge Prep C18 5 μm OBD 19 × 250 mm |
| Mobile phase A/B | 0.1% TFA in H$_2$0/0.1% TFA in Acetonitrile |
| Gradient | 0 min → 30 min: B 20% → B 100% |
| Flow rate | 10 mL/min   Detected wavelength   UV 280 nm |

Example 9-1-2: Synthesis of Compound H -FcBP (L6Dap)-norbornene

Compound II (cis-norbornene Weinreb amide)-FcBP was synthesized in DMF, and in order to introduce Compound II into FcBP (L6Dap)-norbornene, 3 eq of DIPEA and 8.4 μmol of Compound II were dissolved in 7.3 μmol of FcBP (6Dap)-norbornene dissolved in DMF, and the resulting solution was stirred.

After the termination of the reaction was confirmed the reaction solution was concentrated, and Compound II-FcBP (6Dap)-norbornene was purified by Preparative-HPLC. 14.1 mg was obtained by lyophilization after purification, and the purity was also confirmed using HPLC (Purity; >99% (HPLC), yield: 83%).

Figure 30:
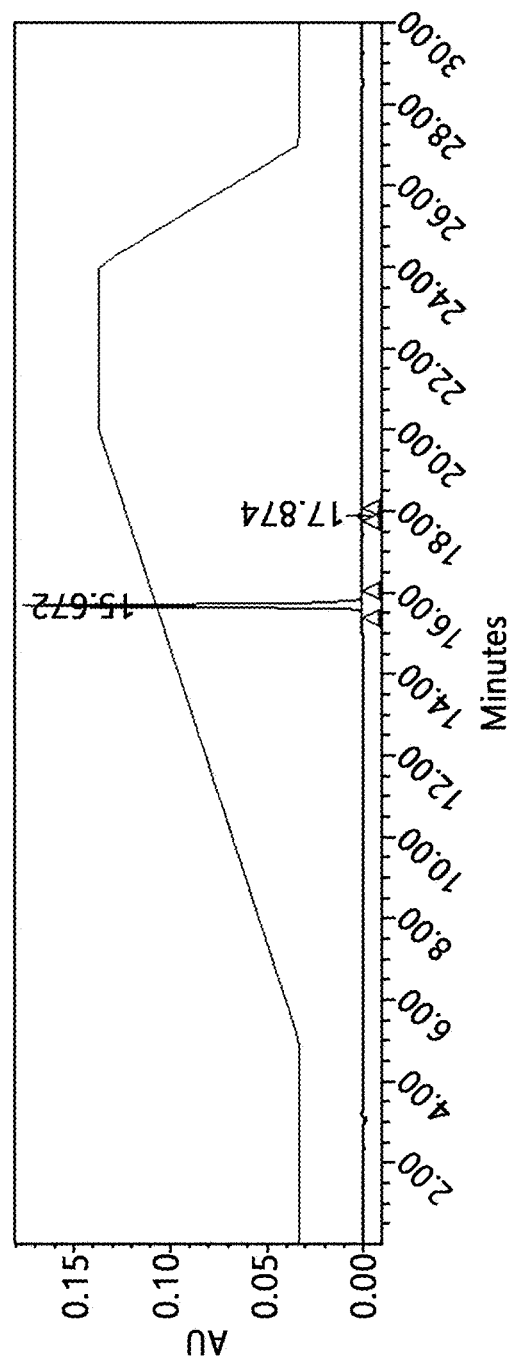
FIG. 30 illustrates the HPLC results of Compound II-FcBP(L6Dap)-norbornene.

The results are illustrated in FIG. 30.

Example 9-1-3: Confirmation of structure of Compound H -FcBP (L6Dap)-norbornene

Figure 31:
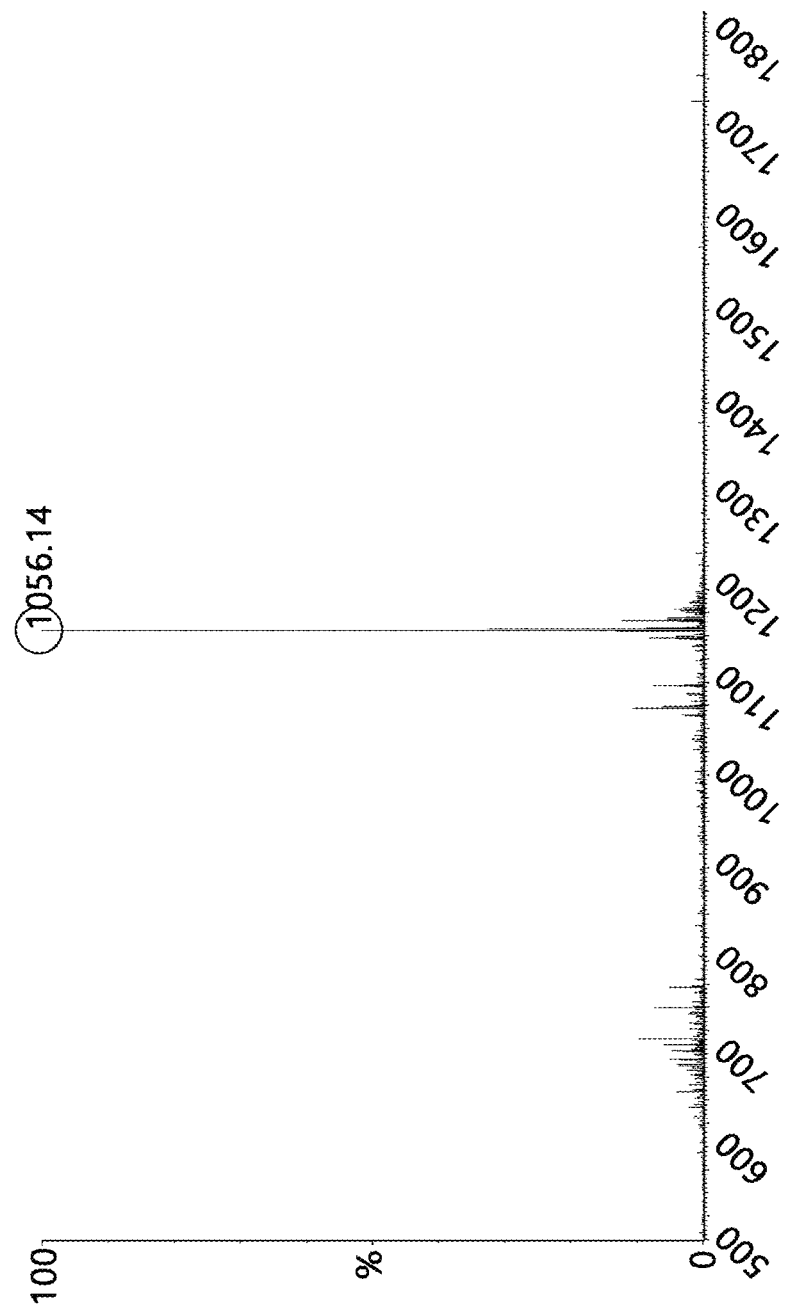
FIG. 31 illustrates the mass spectrometer results of Compound II-FcBP(L6Dap)-norbornene.

Measurement apparatus: Waters Quattro Premier XE
Calculated molecular weight: 2309.61 g/mol
Measured molecular weight (M/2+H)$^2$+: 1155.08 g/mol
The results are illustrated in FIG. 31.

Example 9-1-4: Synthesis of Compound H -FcBP (L6Dab)-norbornene

Compound H (cis-norbornene Weinreb amide)-FcBP was synthesized in DMF, and in order to introduce Compound II into FcBP (L6Dab)-norbornene, 3 eq of DIPEA and 8.4 μmol of Compound II were dissolved in 7.3 μmol of FcBP (6Dab)-norbornene dissolved in DMF, and the resulting solution was stirred.

After the termination of the reaction was confirmed, the reaction solution was concentrated and Compound II-FcBP (6Dab)-norbornene is purified by Preparative-HPLC. 13.8 mg was obtained by lyophilization after purification, and the purity was also confirmed using HPLC (Purity; >99% (HPLC), yield: 82%).

Figure 32:
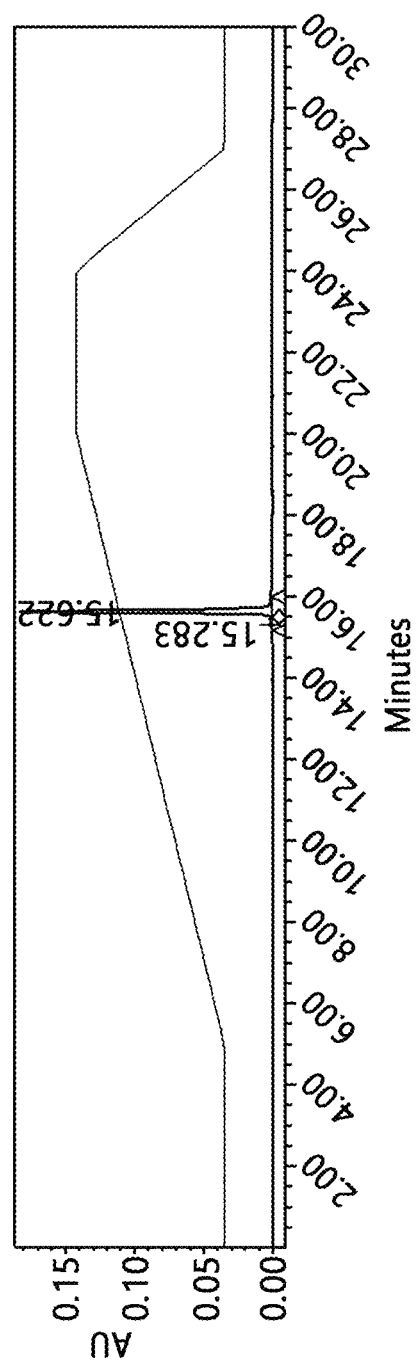
FIG. 32 illustrates the HPLC results of Compound II-FcBP(L6Dab)-norbornene.

The results are illustrated in FIG. 32.

Figure 33:
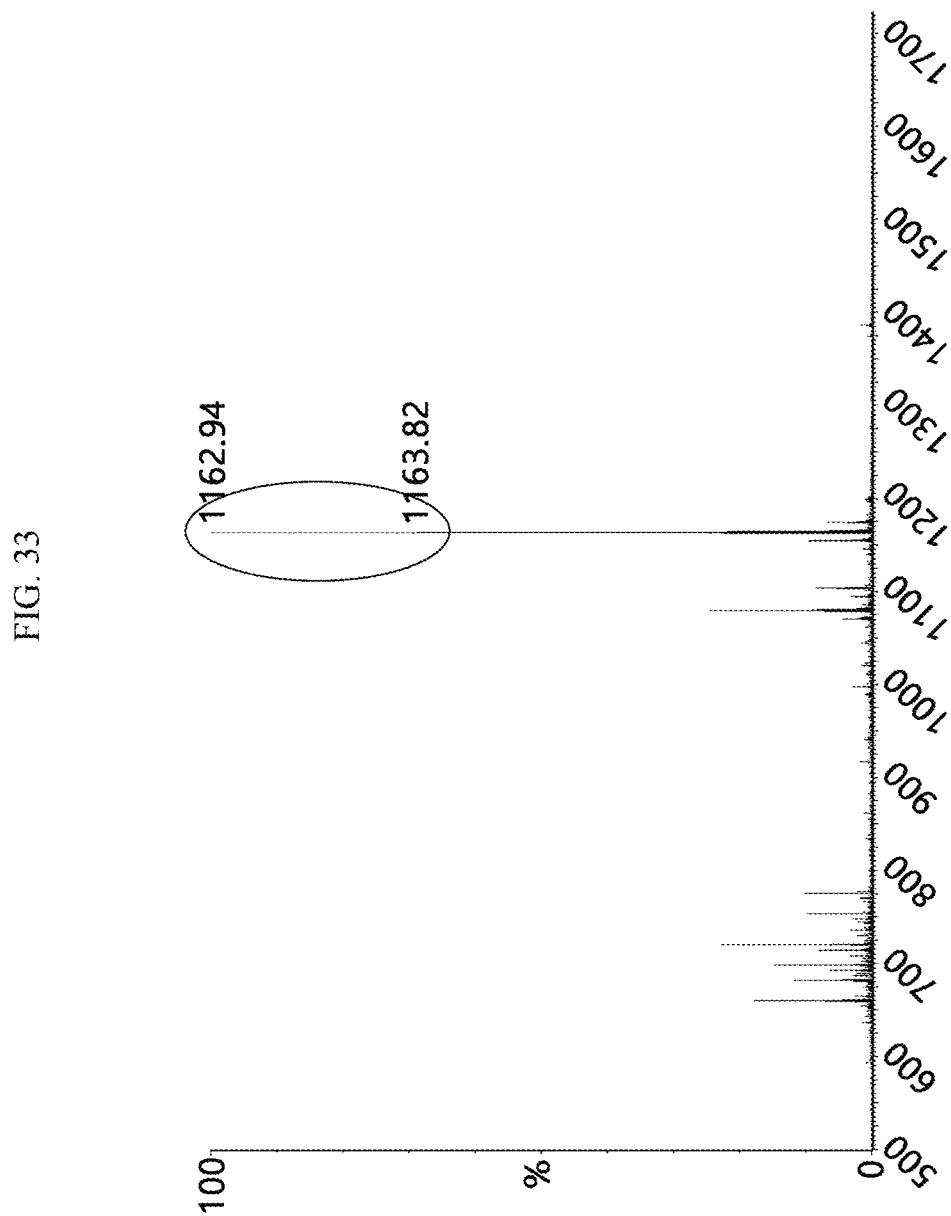
FIG. 33 illustrates the mass spectrometer results of Compound II-FcBP(L6Dab)-norbornene.

Example 9-1-5: Confirmation of structure of Compound H -FcBP (L6Dab)-norbornene Measurement apparatus: Waters Quattro Premier XE Calculated molecular weight: 2323.64 g/mol Measured molecular weight $(M/2+H)^{2+}$: 1162.02 g/mol The results are illustrated in FIG. 33.

Example 9-1-6: Synthesis of Compound H -FcBP (L6Orn)-norbornene

Compound H (cis-norbornene Weinreb amide)-FcBP was synthesized in DMF, and in order to introduce Compound II into FcBP (L6Orn)-norbornene, 3 eq of DIPEA and 8.3 µmol of Compound II were dissolved in 7.2 µmol of FcBP (L6Orn)-norbornene dissolved in DMF, and the resulting solution was stirred.

After the termination of the reaction was confirmed, the reaction solution was concentrated and Compound II-FcBP (L6Orn)-norbornene was purified by Preparative-HPLC. 14.8 mg was obtained by lyophilization after purification, and the purity was also confirmed using HPLC (Purity; >99% (HPLC), yield: 88%).

Figure 34:
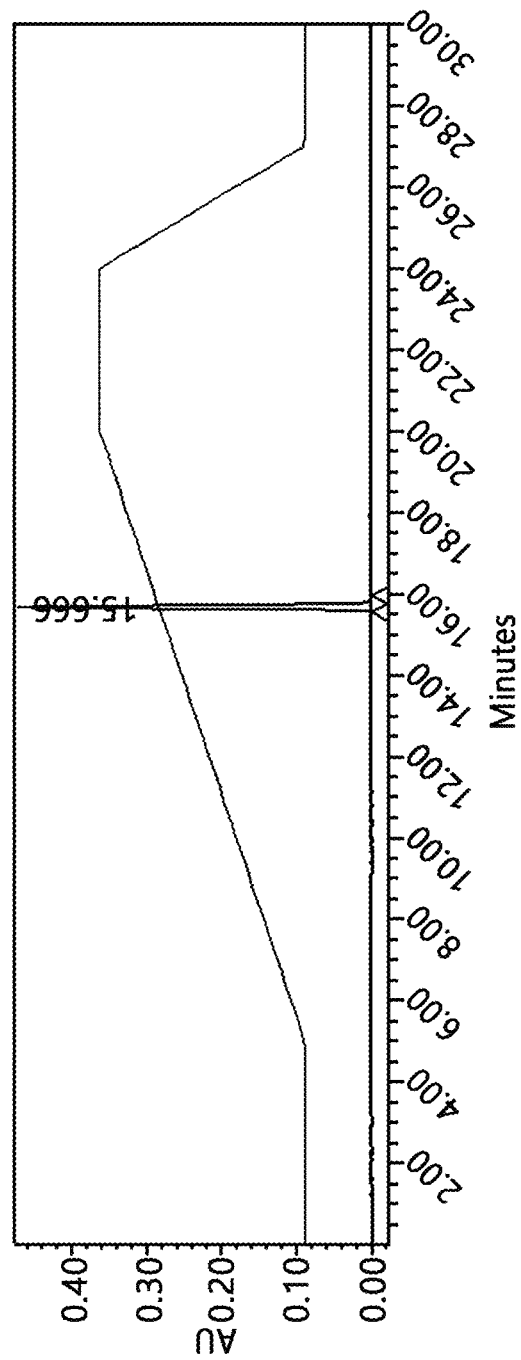
FIG. 34 illustrates the HPLC results of Compound II-FcBP(L6Orn)-norbornene.

The results are illustrated in FIG. 34.

Figure 35:
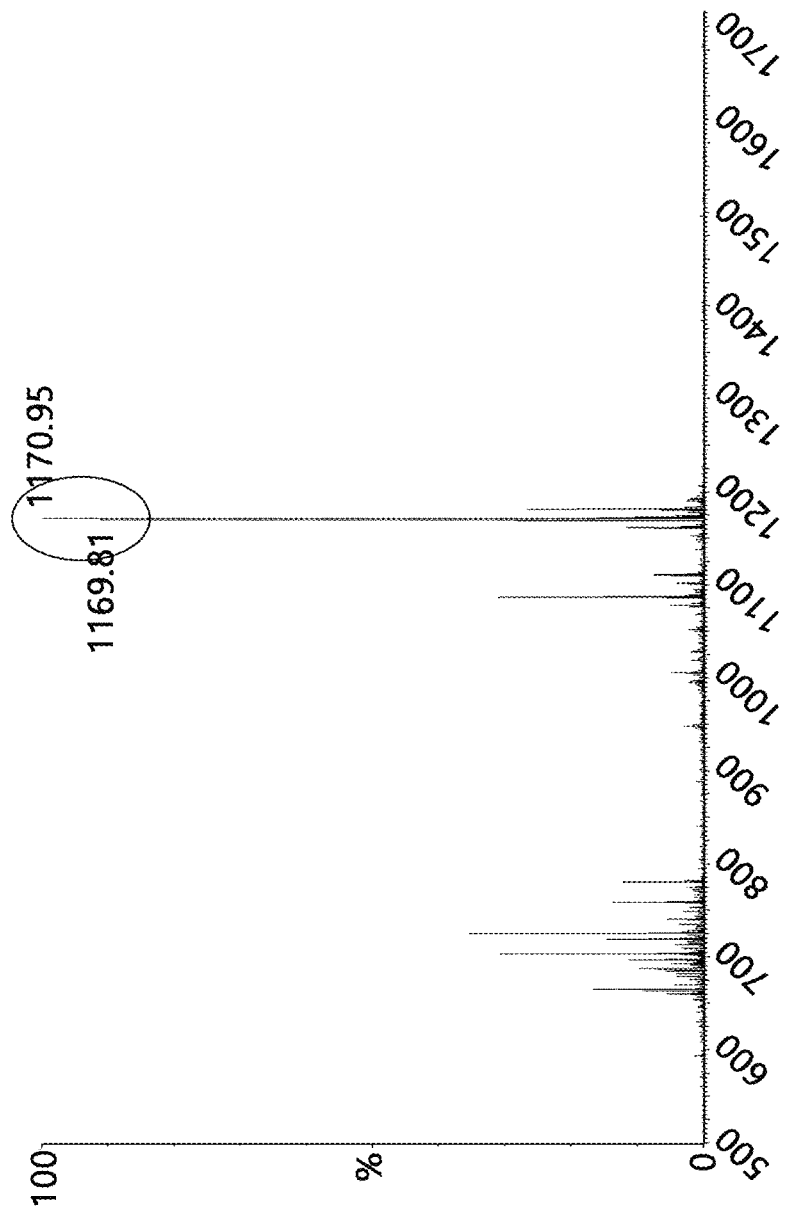
FIG. 35 illustrates the mass spectrometer results of Compound II-FcBP(L6Orn)-norbornene.

Example 9-1-7: Confirmation of structure of Compound H -FcBP (L6Orn)-norbornene Measurement apparatus: Waters Quattro Premier XE Calculated molecular weight: 2337.66 g/mol Measured molecular weight $(M/2+H)^{2+}$: 1169.03 g/mol The results are illustrated in FIG. 35.

Example 9-1-8: Synthesis of Compound H -FcBP (L6Lys)-norbornene

Compound H (cis-norbornene Weinreb amide)-FcBP was synthesized in DMF, and in order to introduce Compound II into FcBP (L6Lys)-norbornene, 3 eq of DIPEA and 8.3 µmol of Compound II were dissolved in 7.2 µmol of FcBP (L6Lys)-norbornene dissolved in DMF, and the resulting solution was stirred.

After the termination of the reaction was confirmed, the reaction solution was concentrated and Compound II-FcBP (6Lys)-norbornene was purified by Preparative-HPLC. 15.4 mg was obtained by lyophilization after purification, and the purity was also confirmed using HPLC (Purity; >99% (HPLC), yield: 91%).

Figure 36:
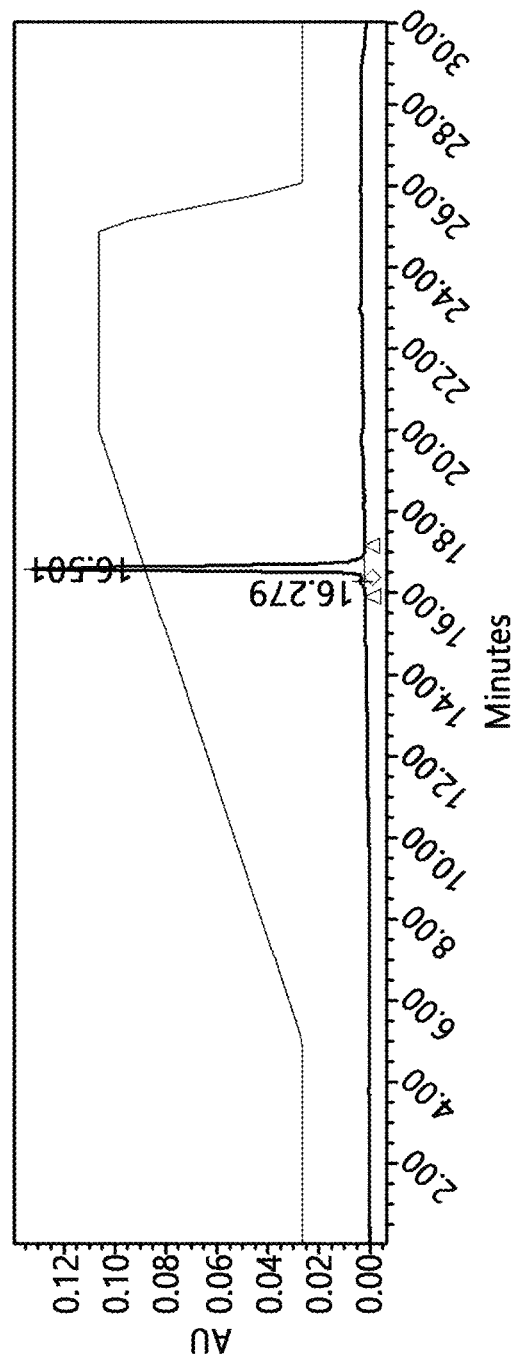
FIG. 36 illustrates the HPLC results of Compound II-FcBP(L6Lys)-norbornene.

The results are illustrated in FIG. 36.

Figure 37:
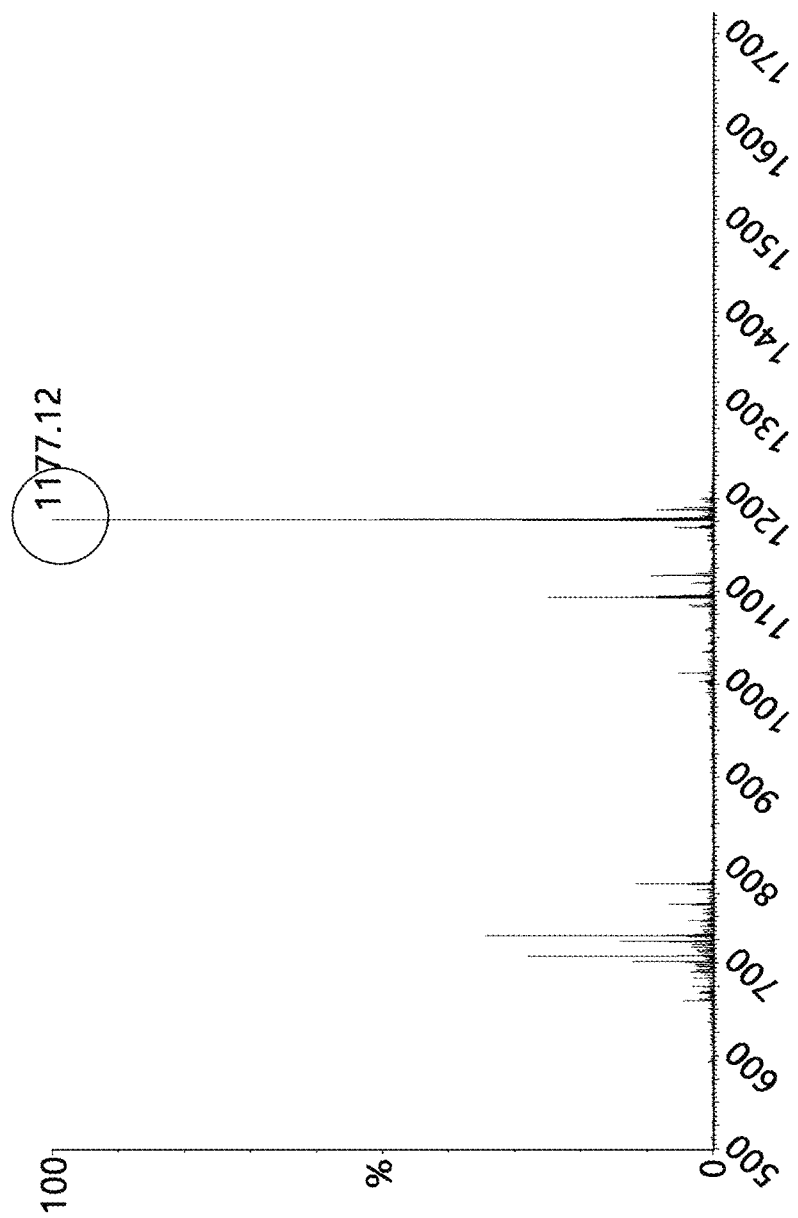
FIG. 37 illustrates the mass spectrometer results of Compound II-FcBP(L6Lys)-norbornene.

Example 9-1-9: Confirmation of structure of Compound H -FcBP (L6Lys)-norbornene Measurement apparatus: Waters Quattro Premier XE Calculated molecular weight: 2351.69 g/mol Measured molecular weight $(M/2+H)^{2+}$: 1176.04 g/mol The results are illustrated in FIG. 37.

[Example 10] Verification of antibody binding efficiency of site-specific interactome according to carbon length

Example 10-1. Production of site-specific antibody-norbornene conjugate by Compound Hf-FcBP (L6Dap, L6Dab, L6Orn, L6Lys)-norbornene

Figure 38:
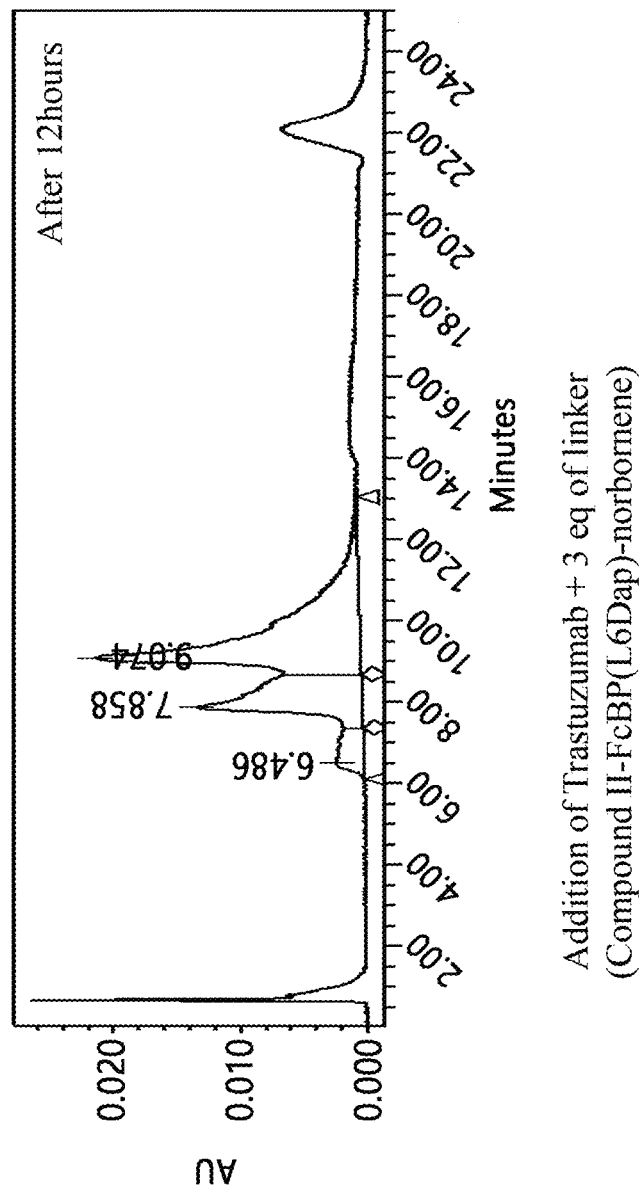
FIG. 38 illustrates the HIC-HPLC results for monitoring a binding reaction with Compound II-FcBP(L6Dap)-norbornene-based antibody.

Example 10-1-1: Synthesis of trastuzumab-norbornene based on Compound H -FcBP (L6Dap)-Norbornene Ab (Lys 246/248)-norbornene was synthesized using Compound H -FcBP (L6Dap)-norbornene in a phosphate buffered saline (PBS) buffer with pH 7.4. In order to introduce norbornene into two specific sites of an antibody (trastuzumab 4 mg/mL, 1 mL), 6 eq of Compound II-FcBP (L6Dap)-norbornene per antibody was put into a reaction solution, and then the reaction was performed. For the reaction temperature and time, it took 12 hours to perform the reaction at room temperature, and reaction monitoring and termination were confirmed by HIC-HPLC. Trastuzumab exhibits peaks at 6.3 to 6.4 minutes on HIC-HPLC. When a FcBP (L6Dap)-norbornene molecule binds to only one of both binding sites of trastuzumab, a peak is observed at 8 minutes on HIC-HPLC. When FcBP (L6Dap)-norbornene molecules bind to both sites of trastuzumab, a peak is observed at 9 minutes on HIC-HPLC. Monitoring of the binding reaction with antibody based on Compound II-FcBP (L6Dap)-norbornene is illustrated in FIG. 38. By observing the peak at 9.074 minutes, it was confirmed that an antibody-payload conjugate with DAR=2 was synthesized.

Figure 39:
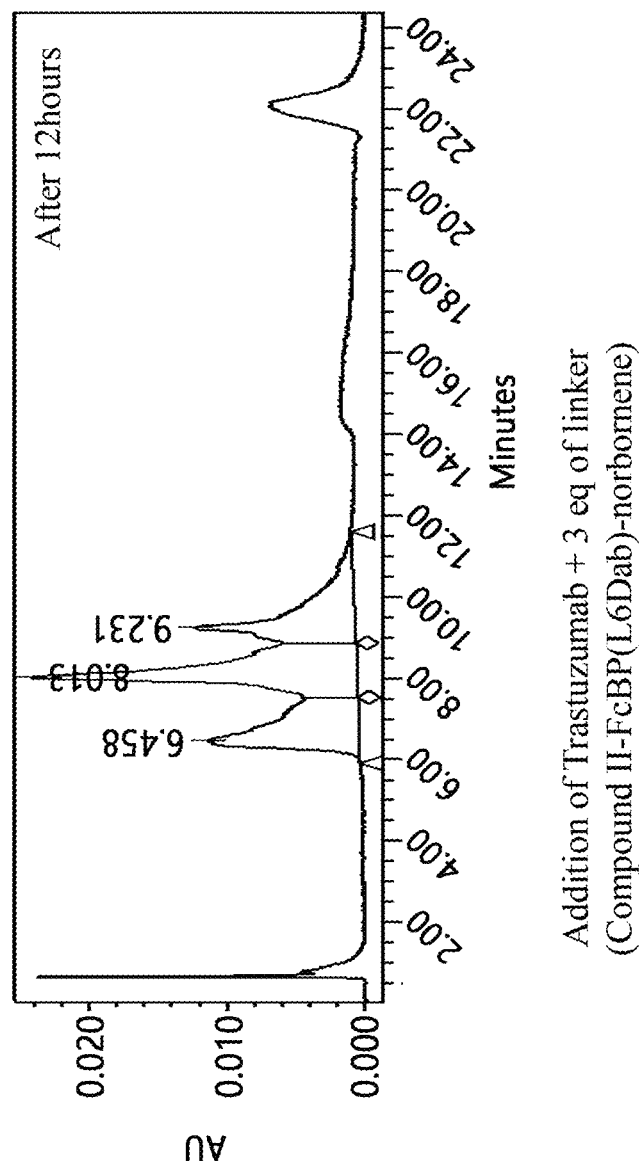
FIG. 39 illustrates the HIC-HPLC results for monitoring a binding reaction with Compound II-FcBP(L6Dab)-norbornene-based antibody.

Example 10-1-2: Synthesis of trastuzumab-norbornene based on Compound H -FcBP(L6Dab)-norbornene Ab (Lys 246/248)-norbornene was synthesized using Compound H -FcBP (L6Dab)-norbornene in a phosphate buffered saline (PBS) buffer with pH 7.4. In order to introduce norbornene into two specific sites of an antibody (trastuzumab 4 mg/mL, 1 mL), 6 eq of Compound II-FcBP (L6Dab)-norbornene per antibody was put into a reaction solution, and then the reaction was performed. For the reaction temperature and time, it took 12 hours to perform the reaction at room temperature, and reaction monitoring and termination were confirmed by HIC-HPLC. Trastuzumab exhibits peaks at 6.3 to 6.4 minutes on HIC-HPLC. When a FcBP (L6Dab)-norbornene molecule binds to only one of both binding sites of trastuzumab, a peak is observed at 8 minutes on HIC-HPLC. When FcBP (L6Dab)-norbornene molecules bind to both sites of trastuzumab, a peak is observed at 9 minutes on HIC-HPLC. Monitoring of the binding reaction with antibody based on Compound II-FcBP (L6Dab)-norbornene is illustrated in FIG. 39. By observing the peak at 9.231 minutes, it was confirmed that an antibody-payload conjugate with DAR=2 was synthesized.

Figure 40:
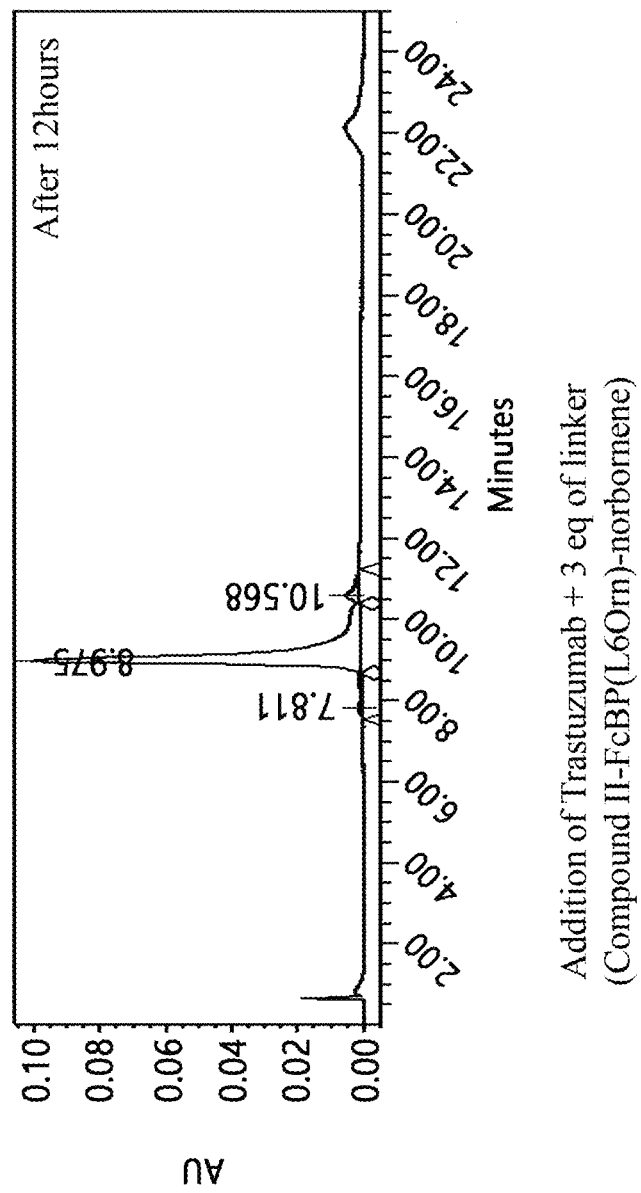
FIG. 40 illustrates the HIC-HPLC results for monitoring a binding reaction with Compound II-FcBP(L6Orn)-norbornene-based antibody.

Example 10-1-3: Synthesis of trastuzumab-norbornene based on Compound H -FcBP(L6Orn)-Norbornene Ab (Lys 246/248)-norbornene was synthesized using Compound H -FcBP (L6Orn)-norbornene in a phosphate buffered saline (PBS) buffer with pH 7.4. In order to introduce norbornene into two specific sites of an antibody (trastuzumab 4 mg/mL, 1 mL), 6 eq of Compound II-FcBP (L6Orn)-norbornene per antibody was put into a reaction solution, and then the reaction was performed. For the reaction temperature and time, it took 12 hours to perform the reaction at room temperature, and reaction monitoring and termination were confirmed by HIC-HPLC. Trastuzumab exhibits peaks at 6.3 to 6.4 minutes on HIC-HPLC. When a FcBP (L6Orn)-norbornene molecule binds to only one of both binding sites of trastuzumab, a peak is observed at 8 minutes on HIC-HPLC. When FcBP (L6Orn)-norbornene molecules bind to both binding sites of trastuzumab, a peak is observed at 9 minutes on HIC-HPLC. Monitoring of the binding reaction with antibody based on Compound II-FcBP (L6Orn)-norbornene is illustrated in FIG. 40. By observing the peak at 8.975 minutes, it was confirmed that an antibody-payload conjugate with DAR=2 was synthesized.

Figure 41:
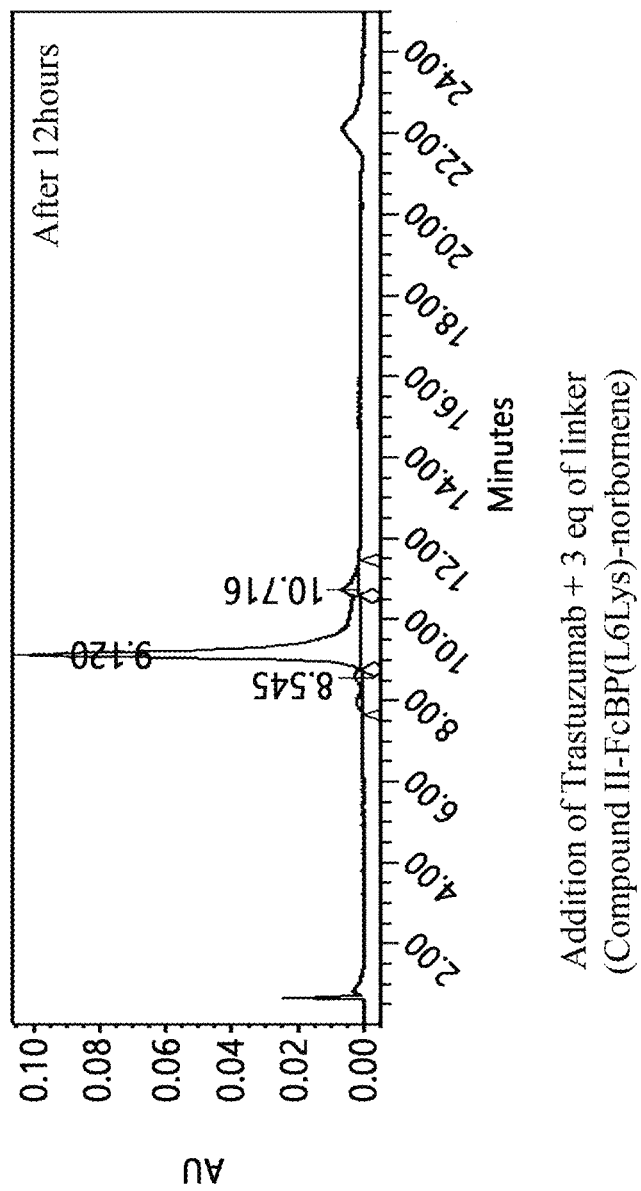
FIG. 41 illustrates the HIC-HPLC results for monitoring a binding reaction with Compound II-FcBP(L6Lys)-norbornene-based antibody.

Example 10-1-4: Synthesis of trastuzumab-norbornene based on Compound H -FcBP (L6Lys)-norbornene Ab (Lys 246/248)-norbornene was synthesized using Compound H -FcBP (L6Lys)-norbornene in a phosphate buffered saline (PBS) buffer with pH 7.4. In order to introduce norbornene into two specific sites of an antibody (trastuzumab 4 mg/mL, 1 mL), 6 eq of Compound II-FcBP (L6Lys)-norbornene per antibody was put into a reaction solution, and then the reaction was performed. For the reaction temperature and time, it took 12 hours to perform the reaction at room temperature, and reaction monitoring and termination were confirmed by HIC-HPLC. Trastuzumab exhibits peaks at 6.3 to 6.4 minutes on HIC-HPLC. When a FcBP (L6Lys)-norbornene molecule binds to only one of both binding sites of trastuzumab, a peak is observed at 8 minutes on HIC-HPLC. When the FcBP (L6Lys)-norbornene molecules bind to both sites, a peak is observed at 9 minutes on HIC-HPLC. Monitoring of the binding reaction with antibody based on Compound II-FcBP (L6Lys)-norbornene is illustrated in FIG. 41. By observing the peak at 9.120 minutes, it was confirmed that an antibody-payload conjugate with DAR=2 was synthesized.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. An antibody-payload conjugate:

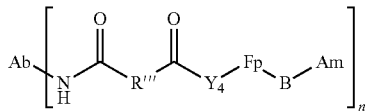 (Formula 8)

wherein, Ab is an antibody,
wherein n is an integer of 1 to 2,
wherein R''' is $C_{1-6}$ alkylene, $C_{2-6}$ alkenylene, $C_{2-6}$ alkynylene, or $C_{1-6}$ heteroalkylene, wherein the heteroalkylene includes at least one selected from a group consisting of N, O, and S,
wherein B is one of a structure formed by a click chemistry reaction of a first click chemistry functional group and a second click chemistry functional group,
wherein the first click chemistry functional group and the second click chemistry functional group are independently selected from a group consisting of acetylene, transcyclooctene, cyclooctyne, dyarylcyclooctyne, methyl ester phosphine, norbornene, tetrazine, methylcyclopropene, azetine, cyanide, azide, and dibenzocyclooctyne, which can be reacted with each other,
wherein Am is an active moiety or a structure including the active moiety, wherein the active moiety comprises a drug molecule,
wherein Fp comprises a Fc binding peptide represented by DCAWHXGELVWCT (SEQ ID NO: 1)
  wherein, D is aspartic acid, C is cysteine, A is alanine, W is tryptophan, H is histidine,
  wherein X is 2,3-Diaminopropionic Acid (Dap) residue, 2,4-diaminobutyric acid (Dab) residue, ornithine (Orn) residue, or lysine (Lys) residue
  wherein G is glycine, E is glutamate, L is leucine, V is valine, and T is threonine,
  wherein, the cysteine at N-terminal and the cysteine at C-terminal are optionally linked to each other by a disulfide bond,
  wherein the Fc binding peptide is linked to the antibody through an amino acid residue 6 of the Fc binding peptide,
wherein, $Y_4$ is NH, wherein $Y_4$ is derived from the amino acid residue 6 of the Fc binding peptide, wherein the amino acid residue 6 of the Fc binding peptide is X, and
wherein, the nitrogen atom linked to the Ab is derived from a lysine 246 of Fc region of the antibody or a lysine 248 of Fc region of the antibody.

2. The antibody-payload conjugate of claim 1, wherein the Fc binding peptide is a peptide represented by DCAWHKGELVWCT (SEQ ID NO: 2).

3. The antibody-payload conjugate of claim 1, wherein R''' is $C_{1-5}$ alkylene, or $C_{1-5}$ heteroalkylene.

4. The antibody-payload conjugate of claim 1, wherein R''' is $C_3$ alkylene.

5. The antibody-payload conjugate of claim 1, wherein the first click chemistry functional group is any one selected from norbornene, tetrazine, dibenzocyclooctyne, and azide, wherein B is

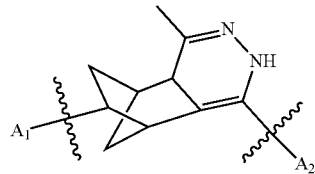

or

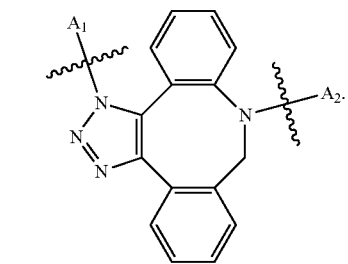

and
wherein $A_1$ is linked to Fp and $A_2$ is linked to Am, or $A_1$ is linked to Am and $A_2$ is linked to Fp.

6. The antibody-payload conjugate of claim 1,
wherein n is 2, and
wherein, the nitrogen atom linked to the Ab is derived from the lysine 246 of Fc region of the antibody or the lysine 248 of Fc region of the antibody.

7. The antibody-payload conjugate of claim 1,
wherein n is 2,
wherein R''' is $C_3$ alkylene,
wherein the Fc binding peptide is represented by DCAWHKGELVWCT (SEQ ID NO: 2),
wherein the first click chemistry functional group is norbornene, tetrazine, dibenzocyclooctyne, or azide,
wherein B is

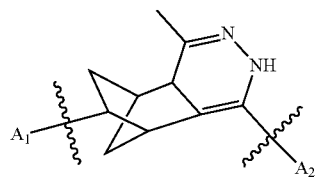

or

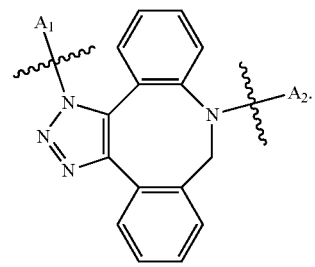

wherein, the nitrogen atom linked to the Ab is derived from the lysine 246 of Fc region of the antibody or the lysine 248 of Fc region of the antibody, and wherein $A_1$ is linked to Fp and $A_2$ is linked to Am, or $A_1$ is linked to Am and $A_2$ is linked to Fp.

8. The antibody-payload conjugate of claim 1, wherein the drug molecule is one or more anticancer drug molecule.

9. The antibody-payload conjugate of claim 8, wherein the anticancer drug molecule is a mertansine (DM 1).

10. The antibody-payload conjugate of claim 1, wherein the drug molecules are two anticancer drug molecules.

11. A composition for treating a cancer, comprising an antibody-payload conjugate of claim 8.

12. The composition of claim 11, wherein the antibody is a trastuzumab, and wherein the cancer is a breast cancer.

* * * * *

```
                         SEQUENCE LISTING

<160> NUMBER OF SEQ ID NOS: 2

<210> SEQ ID NO 1
    <211> LENGTH: 13
    <212> TYPE: PRT
    <213> ORGANISM: Artificial Sequence
    <220> FEATURE:
    <223> OTHER INFORMATION: Fc binding peptide
    <220> FEATURE:
    <221> NAME/KEY: misc_feature
    <222> LOCATION: (6)..(6)
    <223> OTHER INFORMATION: Xaa can be any naturally occurring amino acid

<400> SEQUENCE: 1

Asp Cys Ala Trp His Xaa Gly Glu Leu Val Trp Cys Thr
    1               5                   10

<210> SEQ ID NO 2
    <211> LENGTH: 13
    <212> TYPE: PRT
    <213> ORGANISM: Artificial Sequence
    <220> FEATURE:
    <223> OTHER INFORMATION: Fc binding peptide (L6K)

<400> SEQUENCE: 2

Asp Cys Ala Trp His Lys Gly Glu Leu Val Trp Cys Thr
    1               5                   10
```